(12) United States Patent
Christianson et al.

(10) Patent No.: US 10,463,489 B2
(45) Date of Patent: Nov. 5, 2019

(54) PROSTHETIC HEART VALVE AND SYSTEMS AND METHODS FOR DELIVERING THE SAME

(71) Applicant: Tendyne Holdings, Inc., Roseville, MN (US)

(72) Inventors: Mark Christianson, Plymouth, MN (US); Zachary J. Tegels, Minneapolis, MN (US); Craig A. Ekvall, East Bethel, MN (US); Robert M. Vidlund, Forest Lake, MN (US)

(73) Assignee: Tendyne Holdings, Inc., St. Paul, MN (US)

( * ) Notice: Subject to any disclaimer, the term of this patent is extended or adjusted under 35 U.S.C. 154(b) by 294 days.

(21) Appl. No.: 15/416,353

(22) Filed: Jan. 26, 2017

(65) Prior Publication Data

US 2017/0128208 A1 May 11, 2017

Related U.S. Application Data

(63) Continuation-in-part of application No. 14/864,035, filed on Sep. 24, 2015, which is a continuation of (Continued)

(51) Int. Cl.
*A61F 2/24* (2006.01)
*A61B 17/122* (2006.01)
(Continued)

(52) U.S. Cl.
CPC ...... *A61F 2/2439* (2013.01); *A61B 17/00234* (2013.01); *A61B 17/1227* (2013.01);
(Continued)

(58) Field of Classification Search
CPC .......... A61B 17/00234; A61B 17/0644; A61B 17/068; A61B 17/1227; A61B 17/1285;
(Continued)

(56) References Cited

U.S. PATENT DOCUMENTS 2,697,008 A 12/1954 Rowley
3,409,013 A 11/1968 Berry
(Continued)

FOREIGN PATENT DOCUMENTS

CN 1486161 3/2004
CN 1961845 A 5/2007
(Continued)

OTHER PUBLICATIONS

US 9,155,620 B2, 10/2015, Gross et al. (withdrawn)
(Continued)

*Primary Examiner* — Ryan J. Severson
*Assistant Examiner* — Mohamed G Gabr
(74) *Attorney, Agent, or Firm* — Lerner, David, Littenberg, Krumholz & Mentlik, LLP

(57) ABSTRACT

A prosthetic heart valve includes a self-expanding wire frame body, a valve disposed in the body, a leaflet clip coupled to the body, and a control element operably coupled to the leaflet clip. The body has a proximal end and a distal end. The leaflet clip is configured to be transitioned between a first configuration in which the prosthetic valve can be inserted into a heart, and a second configuration in which the leaflet clip is disposed to capture a native valve leaflet between the leaflet clip and the wire frame body when the body is disposed in a native annulus of an atrioventricular valve of a heart. The control element extends from the leaflet clip through a ventricle of the heart and out a wall of the ventricle to allow a user to transition the leaflet clip from its first configuration to its second configuration.

19 Claims, 41 Drawing Sheets

Related U.S. Application Data application No. PCT/US2014/058826, filed on Oct. 2, 2014, said application No. 14/864,035 is a continuation-in-part of application No. 14/154,546, filed on Jan. 14, 2014, now abandoned.

(60) Provisional application No. 61/807,695, filed on Apr. 2, 2013, provisional application No. 62/291,860, filed on Feb. 5, 2016, provisional application No. 61/896,574, filed on Oct. 28, 2013, provisional application No. 62/049,662, filed on Sep. 12, 2014.

(51) Int. Cl.
  *A61B 17/00* (2006.01)
  *A61B 17/128* (2006.01)
  *A61B 17/064* (2006.01)
  *A61B 17/068* (2006.01)

(52) U.S. Cl.
  CPC .......... *A61F 2/2418* (2013.01); *A61F 2/2457* (2013.01); *A61B 17/068* (2013.01); *A61B 17/0644* (2013.01); *A61B 17/1285* (2013.01); *A61B 2017/00243* (2013.01); *A61B 2017/00867* (2013.01); *A61F 2/2487* (2013.01); *A61F 2210/0014* (2013.01); *A61F 2220/0016* (2013.01); *A61F 2230/005* (2013.01)

(58) Field of Classification Search
  CPC . A61B 2017/00243; A61B 2017/00867; A61F 2210/0014; A61F 2220/0016; A61F 2230/005; A61F 2/2418; A61F 2/2439; A61F 2/2457; A61F 2/2487
  See application file for complete search history.

(56) References Cited

U.S. PATENT DOCUMENTS

| | | |
|---|---|---|
| 3,472,230 A | 10/1969 | Fogarty et al. |
| 3,476,101 A | 11/1969 | Ross |
| 3,548,417 A | 12/1970 | Kisher |
| 3,587,115 A | 6/1971 | Shiley |
| 3,657,744 A | 4/1972 | Ersek |
| 3,671,979 A | 6/1972 | Moulopoulos |
| 3,714,671 A | 2/1973 | Edwards et al. |
| 3,755,823 A | 9/1973 | Hancock |
| 3,976,079 A | 8/1976 | Samuels et al. |
| 4,003,382 A | 1/1977 | Dyke |
| 4,035,849 A | 7/1977 | Angell et al. |
| 4,056,854 A | 11/1977 | Boretos et al. |
| 4,073,438 A | 2/1978 | Meyer |
| 4,106,129 A | 8/1978 | Carpentier et al. |
| 4,222,126 A | 9/1980 | Boretos et al. |
| 4,265,694 A | 5/1981 | Boretos et al. |
| 4,297,749 A | 11/1981 | Davis et al. |
| 4,339,831 A | 7/1982 | Johnson |
| 4,343,048 A | 8/1982 | Ross et al. |
| 4,345,340 A | 8/1982 | Rosen |
| 4,373,216 A | 2/1983 | Klawitter |
| 4,406,022 A | 9/1983 | Roy |
| 4,470,157 A | 9/1984 | Love |
| 4,490,859 A | 1/1985 | Black et al. |
| 4,535,483 A | 8/1985 | Klawitter et al. |
| 4,574,803 A | 3/1986 | Storz |
| 4,585,705 A | 4/1986 | Broderick et al. |
| 4,592,340 A | 6/1986 | Boyles |
| 4,605,407 A | 8/1986 | Black et al. |
| 4,612,011 A | 9/1986 | Kautzky |
| 4,626,255 A | 12/1986 | Reichart et al. |
| 4,638,886 A | 1/1987 | Marietta |
| 4,643,732 A | 2/1987 | Pietsch et al. |
| 4,655,771 A | 4/1987 | Wallsten |
| 4,692,164 A | 9/1987 | Dzemeshkevich et al. |
| 4,733,665 A | 3/1988 | Palmaz |
| 4,759,758 A | 7/1988 | Gabbay |
| 4,762,128 A | 8/1988 | Rosenbluth |
| 4,777,951 A | 10/1988 | Cribier et al. |
| 4,787,899 A | 11/1988 | Lazarus |
| 4,787,901 A | 11/1988 | Baykut |
| 4,796,629 A | 1/1989 | Grayzel |
| 4,824,180 A | 4/1989 | Levrai |
| 4,829,990 A | 5/1989 | Thuroff et al. |
| 4,830,117 A | 5/1989 | Capasso |
| 4,851,001 A | 7/1989 | Taheri |
| 4,856,516 A | 8/1989 | Hillstead |
| 4,878,495 A | 11/1989 | Grayzel |
| 4,878,906 A | 11/1989 | Lindemann et al. |
| 4,883,458 A | 11/1989 | Shiber |
| 4,922,905 A | 5/1990 | Strecker |
| 4,923,013 A | 5/1990 | De Gennaro |
| 4,960,424 A | 10/1990 | Grooters |
| 4,966,604 A | 10/1990 | Reiss |
| 4,979,939 A | 12/1990 | Shiber |
| 4,986,830 A | 1/1991 | Owens et al. |
| 4,994,077 A | 2/1991 | Dobben |
| 4,996,873 A | 3/1991 | Takeuchi |
| 5,007,896 A | 4/1991 | Shiber |
| 5,026,366 A | 6/1991 | Leckrone |
| 5,032,128 A | 7/1991 | Alonso |
| 5,035,706 A | 7/1991 | Giantureo et al. |
| 5,037,434 A | 8/1991 | Lane |
| 5,047,041 A | 9/1991 | Sammuels |
| 5,059,177 A | 10/1991 | Towne et al. |
| 5,064,435 A | 11/1991 | Porter |
| 5,080,668 A | 1/1992 | Bolz et al. |
| 5,085,635 A | 2/1992 | Cragg |
| 5,089,015 A | 2/1992 | Ross |
| 5,152,771 A | 10/1992 | Sabbaghian et al. |
| 5,163,953 A | 11/1992 | Vince |
| 5,167,628 A | 12/1992 | Boyles |
| 5,192,297 A | 3/1993 | Hull |
| 5,201,880 A | 4/1993 | Wright et al. |
| 5,266,073 A | 11/1993 | Wall |
| 5,282,847 A | 2/1994 | Trescony et al. |
| 5,295,958 A | 3/1994 | Shturman |
| 5,306,296 A | 4/1994 | Wright et al. |
| 5,332,402 A | 7/1994 | Teitelbaum |
| 5,336,616 A | 8/1994 | Livesey et al. |
| 5,344,442 A | 9/1994 | Deac |
| 5,360,444 A | 11/1994 | Kusuhara |
| 5,364,407 A | 11/1994 | Poll |
| 5,370,685 A | 12/1994 | Stevens |
| 5,397,351 A | 3/1995 | Pavcnik et al. |
| 5,411,055 A | 5/1995 | Kane et al. |
| 5,411,552 A | 5/1995 | Andersen et al. |
| 5,415,667 A | 5/1995 | Frater |
| 5,443,446 A | 8/1995 | Shturman |
| 5,480,424 A | 1/1996 | Cox |
| 5,500,014 A | 3/1996 | Quijano et al. |
| 5,545,209 A | 8/1996 | Roberts et al. |
| 5,545,214 A | 8/1996 | Stevens |
| 5,549,665 A | 8/1996 | Vesely et al. |
| 5,554,184 A | 9/1996 | Machiraju |
| 5,554,185 A | 9/1996 | Block et al. |
| 5,571,175 A | 11/1996 | Vanney et al. |
| 5,591,185 A | 1/1997 | Kilmer et al. |
| 5,607,462 A | 3/1997 | Imran |
| 5,607,464 A | 3/1997 | Trescony et al. |
| 5,609,626 A | 3/1997 | Quijano et al. |
| 5,639,274 A | 6/1997 | Fischell et al. |
| 5,662,704 A | 9/1997 | Gross |
| 5,665,115 A | 9/1997 | Cragg |
| 5,674,279 A | 10/1997 | Wright et al. |
| 5,697,905 A | 12/1997 | Ambrosio |
| 5,702,368 A | 12/1997 | Stevens et al. |
| 5,716,417 A | 2/1998 | Girard et al. |
| 5,728,068 A | 3/1998 | Leone et al. |
| 5,728,151 A | 3/1998 | Garrison et al. |
| 5,735,842 A | 4/1998 | Krueger et al. |
| 5,741,333 A | 4/1998 | Frid |
| 5,749,890 A | 5/1998 | Shaknovich |
| 5,756,476 A | 5/1998 | Epstein |

(56) References Cited

U.S. PATENT DOCUMENTS

| | | |
|---|---|---|
| 5,769,812 A | 6/1998 | Stevens et al. |
| 5,792,179 A | 8/1998 | Sideris |
| 5,800,508 A | 9/1998 | Goicoechea et al. |
| 5,833,673 A | 11/1998 | Ockuly et al. |
| 5,840,081 A | 11/1998 | Andersen et al. |
| 5,855,597 A | 1/1999 | Jayaraman |
| 5,855,601 A | 1/1999 | Bessler |
| 5,855,602 A | 1/1999 | Angell |
| 5,904,697 A | 5/1999 | Gifford, III et al. |
| 5,925,063 A | 7/1999 | Khosravi |
| 5,957,949 A | 9/1999 | Leonhardt et al. |
| 5,968,052 A | 10/1999 | Sullivan, III et al. |
| 5,968,068 A | 10/1999 | Dehdashtian et al. |
| 5,972,030 A | 10/1999 | Garrison et al. |
| 5,993,481 A | 11/1999 | Marcade et al. |
| 6,027,525 A | 2/2000 | Suh et al. |
| 6,042,607 A | 3/2000 | Williamson, IV et al. |
| 6,045,497 A | 4/2000 | Schweich, Jr. et al. |
| 6,063,112 A | 5/2000 | Sgro et al. |
| 6,077,214 A | 6/2000 | Mortier et al. |
| 6,099,508 A | 8/2000 | Bousquet |
| 6,132,473 A | 10/2000 | Williams et al. |
| 6,168,614 B1 | 1/2001 | Andersen et al. |
| 6,171,335 B1 | 1/2001 | Wheatley et al. |
| 6,174,327 B1 | 1/2001 | Mertens et al. |
| 6,183,411 B1 | 2/2001 | Mortier et al. |
| 6,210,408 B1 | 4/2001 | Chandrasakaran et al. |
| 6,217,585 B1 | 4/2001 | Houser et al. |
| 6,221,091 B1 | 4/2001 | Khosravi |
| 6,231,602 B1 | 5/2001 | Carpentier et al. |
| 6,245,102 B1 | 6/2001 | Jayaraman |
| 6,260,552 B1 | 7/2001 | Mortier et al. |
| 6,261,222 B1 | 7/2001 | Schweich, Jr. et al. |
| 6,264,602 B1 | 7/2001 | Mortier et al. |
| 6,287,339 B1 | 9/2001 | Vazquez et al. |
| 6,299,637 B1 | 10/2001 | Shaolian |
| 6,302,906 B1 | 10/2001 | Goecoechea et al. |
| 6,312,465 B1 | 11/2001 | Griffin et al. |
| 6,332,893 B1 | 12/2001 | Mortier et al. |
| 6,350,277 B1 | 2/2002 | Kocur |
| 6,358,277 B1 | 3/2002 | Duran |
| 6,379,372 B1 | 4/2002 | Dehdashtian et al. |
| 6,402,679 B1 | 6/2002 | Mortier et al. |
| 6,402,680 B2 | 6/2002 | Mortier et al. |
| 6,402,781 B1 | 6/2002 | Langberg et al. |
| 6,406,420 B1 | 6/2002 | McCarthy et al. |
| 6,425,916 B1 | 7/2002 | Garrison et al. |
| 6,440,164 B1 | 8/2002 | Di Matteo et al. |
| 6,454,799 B1 | 9/2002 | Schreck |
| 6,458,153 B1 | 10/2002 | Bailey et al. |
| 6,461,382 B1 | 10/2002 | Cao |
| 6,468,660 B2 | 10/2002 | Ogle et al. |
| 6,482,228 B1 | 11/2002 | Norred |
| 6,488,704 B1 | 12/2002 | Connelly et al. |
| 6,537,198 B1 | 3/2003 | Vidlund et al. |
| 6,540,782 B1 | 4/2003 | Snyders |
| 6,569,196 B1 | 5/2003 | Vesely et al. |
| 6,575,252 B2 | 6/2003 | Reed |
| 6,582,462 B1 | 6/2003 | Andersen et al. |
| 6,605,112 B1 | 8/2003 | Moll |
| 6,616,684 B1 | 9/2003 | Vidlund et al. |
| 6,622,730 B2 | 9/2003 | Ekvall et al. |
| 6,629,534 B1 | 10/2003 | St. Goar et al. |
| 6,629,921 B1 | 10/2003 | Schweich, Jr. et al. |
| 6,648,077 B2 | 11/2003 | Hoffman |
| 6,648,921 B2 | 11/2003 | Anderson et al. |
| 6,652,578 B2 | 11/2003 | Bailey et al. |
| 6,669,724 B2 | 12/2003 | Park et al. |
| 6,706,065 B2 | 3/2004 | Langberg et al. |
| 6,709,456 B2 | 3/2004 | Langberg et al. |
| 6,723,038 B1 | 4/2004 | Schroeder et al. |
| 6,726,715 B2 | 4/2004 | Sutherland |
| 6,730,118 B2 | 5/2004 | Spenser et al. |
| 6,733,525 B2 | 5/2004 | Yang et al. |
| 6,740,105 B2 | 5/2004 | Yodfat et al. |
| 6,746,401 B2 | 6/2004 | Panescu |
| 6,746,471 B2 | 6/2004 | Mortier et al. |
| 6,752,813 B2 | 6/2004 | Goldfarb et al. |
| 6,764,510 B2 | 7/2004 | Vidlund et al. |
| 6,797,002 B2 | 9/2004 | Spence et al. |
| 6,810,882 B2 | 11/2004 | Langberg et al. |
| 6,830,584 B1 | 12/2004 | Seguin |
| 6,854,668 B2 | 2/2005 | Wancho et al. |
| 6,855,144 B2 | 2/2005 | Lesh |
| 6,858,001 B1 | 2/2005 | Aboul-Hosn |
| 6,890,353 B2 | 5/2005 | Cohn et al. |
| 6,893,460 B2 | 5/2005 | Spenser et al. |
| 6,896,690 B1 | 5/2005 | Lambrecht et al. |
| 6,908,424 B2 | 6/2005 | Mortier et al. |
| 6,908,481 B2 | 6/2005 | Cribier |
| 6,936,067 B2 | 8/2005 | Buchanan |
| 6,945,996 B2 | 9/2005 | Sedransk |
| 6,955,175 B2 | 10/2005 | Stevens et al. |
| 6,974,476 B2 | 12/2005 | McGuckin et al. |
| 6,976,543 B1 | 12/2005 | Fischer |
| 6,997,950 B2 | 2/2006 | Chawla |
| 7,018,406 B2 | 3/2006 | Seguin et al. |
| 7,018,408 B2 | 3/2006 | Bailey et al. |
| 7,044,905 B2 | 5/2006 | Vidlund et al. |
| 7,060,021 B1 | 6/2006 | Wilk |
| 7,077,862 B2 | 7/2006 | Vidlund et al. |
| 7,087,064 B1 | 8/2006 | Hyde |
| 7,100,614 B2 | 9/2006 | Stevens et al. |
| 7,101,395 B2 | 9/2006 | Tremulis et al. |
| 7,108,717 B2 | 9/2006 | Freidberg |
| 7,112,219 B2 | 9/2006 | Vidlund et al. |
| 7,115,141 B2 | 10/2006 | Menz et al. |
| 7,141,064 B2 | 11/2006 | Scott et al. |
| 7,175,656 B2 | 2/2007 | Khairkhahan |
| 7,198,646 B2 | 4/2007 | Figulla et al. |
| 7,201,772 B2 | 4/2007 | Schwammenthal et al. |
| 7,247,134 B2 | 7/2007 | Vidlund et al. |
| 7,252,682 B2 | 8/2007 | Seguin |
| 7,267,686 B2 | 9/2007 | DiMatteo et al. |
| 7,275,604 B1 | 10/2007 | Wall |
| 7,276,078 B2 | 10/2007 | Spenser et al. |
| 7,276,084 B2 | 10/2007 | Yang et al. |
| 7,316,706 B2 | 1/2008 | Bloom et al. |
| 7,318,278 B2 | 1/2008 | Zhang et al. |
| 7,326,236 B2 | 2/2008 | Andreas et al. |
| 7,329,278 B2 | 2/2008 | Seguin et al. |
| 7,331,991 B2 | 2/2008 | Kheradvar et al. |
| 7,335,213 B1 | 2/2008 | Hyde et al. |
| 7,374,571 B2 | 5/2008 | Pease et al. |
| 7,377,941 B2 | 5/2008 | Rhee et al. |
| 7,381,210 B2 | 6/2008 | Zarbatany et al. |
| 7,381,218 B2 | 6/2008 | Schreck |
| 7,393,360 B2 | 7/2008 | Spenser et al. |
| 7,404,824 B1 | 7/2008 | Webler et al. |
| 7,416,554 B2 | 8/2008 | Lam et al. |
| 7,422,072 B2 | 9/2008 | Dade |
| 7,429,269 B2 | 9/2008 | Schwammenthal et al. |
| 7,442,204 B2 | 10/2008 | Schwammenthal et al. |
| 7,445,631 B2 | 11/2008 | Salahieh et al. |
| 7,462,191 B2 | 12/2008 | Spenser et al. |
| 7,470,285 B2 | 12/2008 | Nugent et al. |
| 7,500,989 B2 | 3/2009 | Solem et al. |
| 7,503,931 B2 | 3/2009 | Kowalsky et al. |
| 7,510,572 B2 | 3/2009 | Gabbay |
| 7,510,575 B2 | 3/2009 | Spenser et al. |
| 7,513,908 B2 | 4/2009 | Lattouf |
| 7,524,330 B2 | 4/2009 | Berreklouw |
| 7,527,647 B2 | 5/2009 | Spence |
| 7,534,260 B2 | 5/2009 | Lattouf |
| 7,556,646 B2 | 7/2009 | Yang et al. |
| 7,579,381 B2 | 8/2009 | Dove |
| 7,585,321 B2 | 9/2009 | Cribier |
| 7,591,847 B2 | 9/2009 | Navia et al. |
| 7,618,446 B2 | 11/2009 | Andersen et al. |
| 7,618,447 B2 | 11/2009 | Case et al. |
| 7,621,948 B2 | 11/2009 | Herrmann et al. |
| 7,632,304 B2 | 12/2009 | Park |
| 7,632,308 B2 | 12/2009 | Loulmet |
| 7,635,386 B1 | 12/2009 | Gammie |

(56) References Cited

U.S. PATENT DOCUMENTS

| | | |
|---|---|---|
| 7,674,222 B2 | 3/2010 | Nikolic et al. |
| 7,674,286 B2 | 3/2010 | Alfieri et al. |
| 7,695,510 B2 | 4/2010 | Bloom et al. |
| 7,708,775 B2 | 5/2010 | Rowe et al. |
| 7,748,389 B2 | 7/2010 | Salahieh et al. |
| 7,766,961 B2 | 8/2010 | Patel et al. |
| 7,789,909 B2 | 9/2010 | Andersen et al. |
| 7,803,168 B2 | 9/2010 | Gifford et al. |
| 7,803,184 B2 | 9/2010 | McGuckin, Jr. et al. |
| 7,803,185 B2 | 9/2010 | Gabbay |
| 7,806,928 B2 | 10/2010 | Rowe et al. |
| 7,837,727 B2 | 11/2010 | Goetz et al. |
| 7,854,762 B2 | 12/2010 | Speziali et al. |
| 7,892,281 B2 | 2/2011 | Seguin et al. |
| 7,896,915 B2 | 3/2011 | Guyenot et al. |
| 7,901,454 B2 | 3/2011 | Kapadia et al. |
| 7,927,370 B2 | 4/2011 | Webler et al. |
| 7,931,630 B2 | 4/2011 | Nishtala et al. |
| 7,942,928 B2 | 5/2011 | Webler et al. |
| 7,955,247 B2 | 6/2011 | Levine et al. |
| 7,955,385 B2 | 6/2011 | Crittenden |
| 7,972,378 B2 | 7/2011 | Tabor et al. |
| 7,988,727 B2 | 8/2011 | Santamore et al. |
| 7,993,394 B2 | 8/2011 | Hariton et al. |
| 8,007,992 B2 | 8/2011 | Tian et al. |
| 8,029,556 B2 | 10/2011 | Rowe |
| 8,043,368 B2 | 10/2011 | Crabtree |
| 8,052,749 B2 | 11/2011 | Salahieh |
| 8,052,750 B2 | 11/2011 | Tuval et al. |
| 8,052,751 B2 | 11/2011 | Aklog et al. |
| 8,062,355 B2 | 11/2011 | Figulla et al. |
| 8,062,359 B2 | 11/2011 | Marquez et al. |
| 8,070,802 B2 | 12/2011 | Lamphere et al. |
| 8,109,996 B2 | 2/2012 | Stacchino et al. |
| 8,142,495 B2 | 3/2012 | Hasenkam et al. |
| 8,152,821 B2 | 4/2012 | Gambale et al. |
| 8,157,810 B2 | 4/2012 | Case et al. |
| 8,167,932 B2 | 5/2012 | Bourang et al. |
| 8,167,934 B2 | 5/2012 | Styrc et al. |
| 8,187,299 B2 | 5/2012 | Goldfarb et al. |
| 8,206,439 B2 | 6/2012 | Gomez Duran |
| 8,216,301 B2 | 7/2012 | Bonhoeffer et al. |
| 8,226,711 B2 | 7/2012 | Mortier et al. |
| 8,236,045 B2 | 8/2012 | Benichou et al. |
| 8,241,274 B2 | 8/2012 | Keogh et al. |
| 8,252,051 B2 | 8/2012 | Chau et al. |
| 8,303,653 B2 | 11/2012 | Bonhoeffer et al. |
| 8,308,796 B2 | 11/2012 | Lashinski et al. |
| 8,323,334 B2 | 12/2012 | Deem et al. |
| 8,353,955 B2 | 1/2013 | Styrc et al. |
| RE44,075 E | 3/2013 | Williamson et al. |
| 8,449,599 B2 | 5/2013 | Chau et al. |
| 8,454,656 B2 | 6/2013 | Tuval |
| 8,470,028 B2 | 6/2013 | Thornton et al. |
| 8,480,730 B2 | 7/2013 | Maurer et al. |
| 8,486,138 B2 | 7/2013 | Vesely |
| 8,506,623 B2 | 8/2013 | Wilson et al. |
| 8,506,624 B2 | 8/2013 | Vidlund et al. |
| 8,578,705 B2 | 11/2013 | Sindano et al. |
| 8,579,913 B2 | 11/2013 | Nielsen |
| 8,591,573 B2 | 11/2013 | Barone |
| 8,591,576 B2 | 11/2013 | Hasenkam et al. |
| 8,597,347 B2 | 12/2013 | Maurer et al. |
| 8,685,086 B2 | 4/2014 | Navia et al. |
| 8,790,394 B2 | 7/2014 | Miller et al. |
| 8,845,717 B2 | 9/2014 | Khairkhahan et al. |
| 8,888,843 B2 | 11/2014 | Khairkhahan et al. |
| 8,900,214 B2 | 12/2014 | Nance et al. |
| 8,900,295 B2 | 12/2014 | Migliazza et al. |
| 8,926,696 B2 | 1/2015 | Cabiri et al. |
| 8,932,342 B2 | 1/2015 | McHugo et al. |
| 8,932,348 B2 | 1/2015 | Solem et al. |
| 8,945,208 B2 | 2/2015 | Jimenez et al. |
| 8,956,407 B2 | 2/2015 | Macoviak et al. |
| 8,979,922 B2 | 3/2015 | Thambar et al. |
| 8,986,376 B2 | 3/2015 | Solem |
| 9,011,522 B2 | 4/2015 | Annest et al. |
| 9,023,099 B2 | 5/2015 | Duffy et al. |
| 9,034,032 B2 | 5/2015 | McLean et al. |
| 9,034,033 B2 | 5/2015 | McLean et al. |
| 9,039,757 B2 | 5/2015 | McLean et al. |
| 9,039,759 B2 | 5/2015 | Alkhatib et al. |
| 9,078,645 B2 | 7/2015 | Conklin et al. |
| 9,078,749 B2 | 7/2015 | Lutter et al. |
| 9,084,676 B2 | 7/2015 | Chau et al. |
| 9,095,433 B2 | 8/2015 | Lutter et al. |
| 9,125,742 B2 | 9/2015 | Yoganathan et al. |
| 9,149,357 B2 | 10/2015 | Sequin |
| 9,161,837 B2 | 10/2015 | Kapadia |
| 9,168,137 B2 | 10/2015 | Subramanian et al. |
| 9,232,995 B2 | 1/2016 | Kovalsky et al. |
| 9,232,998 B2 | 1/2016 | Wilson et al. |
| 9,232,999 B2 | 1/2016 | Maurer et al. |
| 9,241,702 B2 | 1/2016 | Maisano et al. |
| 9,254,192 B2 | 2/2016 | Lutter et al. |
| 9,265,608 B2 | 2/2016 | Miller et al. |
| 9,289,295 B2 | 3/2016 | Aklog et al. |
| 9,289,297 B2 | 3/2016 | Wilson et al. |
| 9,345,573 B2 | 5/2016 | Nyuli et al. |
| 9,480,557 B2 | 11/2016 | Pellegrini et al. |
| 9,480,559 B2 | 11/2016 | Vidlund et al. |
| 9,526,611 B2 | 12/2016 | Tegels et al. |
| 9,597,181 B2 | 3/2017 | Christianson et al. |
| 9,610,159 B2 | 4/2017 | Christianson et al. |
| 9,675,454 B2 | 6/2017 | Vidlund et al. |
| 9,730,792 B2 | 8/2017 | Lutter et al. |
| 9,827,092 B2 | 11/2017 | Vidlund et al. |
| 9,833,315 B2 | 12/2017 | Vidlund et al. |
| 9,867,700 B2 | 1/2018 | Bakis et al. |
| 9,883,941 B2 | 2/2018 | Hastings et al. |
| 9,895,221 B2 | 2/2018 | Vidlund |
| 9,986,993 B2 | 6/2018 | Vidlund et al. |
| 2001/0018611 A1 | 8/2001 | Solem et al. |
| 2001/0021872 A1 | 9/2001 | Bailey et al. |
| 2001/0025171 A1 | 9/2001 | Mortier et al. |
| 2002/0010427 A1 | 1/2002 | Scarfone et al. |
| 2002/0116054 A1 | 8/2002 | Lundell et al. |
| 2002/0139056 A1 | 10/2002 | Finnell |
| 2002/0151961 A1 | 10/2002 | Lashinski et al. |
| 2002/0161377 A1 | 10/2002 | Rabkin |
| 2002/0173842 A1 | 11/2002 | Buchanan |
| 2002/0183827 A1 | 12/2002 | Derus et al. |
| 2003/0010509 A1 | 1/2003 | Hoffman |
| 2003/0036698 A1 | 2/2003 | Kohler et al. |
| 2003/0050694 A1 | 3/2003 | Yang et al. |
| 2003/0078652 A1 | 4/2003 | Sutherland |
| 2003/0100939 A1 | 5/2003 | Yodfat et al. |
| 2003/0105519 A1 | 6/2003 | Fasol et al. |
| 2003/0105520 A1 | 6/2003 | Alferness et al. |
| 2003/0120340 A1 | 6/2003 | Liska et al. |
| 2003/0130731 A1 | 7/2003 | Vidlund et al. |
| 2003/0149476 A1 | 8/2003 | Damm et al. |
| 2003/0212454 A1 | 11/2003 | Scott et al. |
| 2004/0039436 A1 | 2/2004 | Spenser et al. |
| 2004/0049266 A1 | 3/2004 | Anduiza et al. |
| 2004/0064014 A1 | 4/2004 | Melvin et al. |
| 2004/0092858 A1 | 5/2004 | Wilson et al. |
| 2004/0093075 A1 | 5/2004 | Kuehne |
| 2004/0097865 A1 | 5/2004 | Anderson et al. |
| 2004/0127983 A1 | 7/2004 | Mortier et al. |
| 2004/0133263 A1 | 7/2004 | Dusbabek et al. |
| 2004/0147958 A1 | 7/2004 | Lam et al. |
| 2004/0152947 A1 | 8/2004 | Schroeder et al. |
| 2004/0162610 A1 | 8/2004 | Liska et al. |
| 2004/0163828 A1 | 8/2004 | Silverstein et al. |
| 2004/0181239 A1 | 9/2004 | Dorn et al. |
| 2004/0186565 A1 | 9/2004 | Schreck |
| 2004/0186566 A1 | 9/2004 | Hindrichs et al. |
| 2004/0260317 A1 | 12/2004 | Bloom et al. |
| 2004/0260389 A1 | 12/2004 | Case et al. |
| 2005/0004652 A1 | 1/2005 | Van der Burg et al. |
| 2005/0004666 A1 | 1/2005 | Alfieri et al. |
| 2005/0075727 A1 | 4/2005 | Wheatley |
| 2005/0080402 A1 | 4/2005 | Santamore et al. |

(56) References Cited

U.S. PATENT DOCUMENTS

| | | |
|---|---|---|
| 2005/0085900 A1 | 4/2005 | Case et al. |
| 2005/0096498 A1 | 5/2005 | Houser et al. |
| 2005/0107661 A1 | 5/2005 | Lau et al. |
| 2005/0113798 A1 | 5/2005 | Slater et al. |
| 2005/0113810 A1 | 5/2005 | Houser et al. |
| 2005/0113811 A1 | 5/2005 | Houser et al. |
| 2005/0119519 A9 | 6/2005 | Girard et al. |
| 2005/0121206 A1 | 6/2005 | Dolan |
| 2005/0125012 A1 | 6/2005 | Houser et al. |
| 2005/0137686 A1 | 6/2005 | Salahieh et al. |
| 2005/0137688 A1 | 6/2005 | Salahieh et al. |
| 2005/0137695 A1 | 6/2005 | Salahieh et al. |
| 2005/0137698 A1 | 6/2005 | Salahieh et al. |
| 2005/0148815 A1 | 7/2005 | Mortier et al. |
| 2005/0177180 A1 | 8/2005 | Kaganov et al. |
| 2005/0197695 A1 | 9/2005 | Stacchino |
| 2005/0203614 A1 | 9/2005 | Forster et al. |
| 2005/0203615 A1 | 9/2005 | Forster et al. |
| 2005/0203617 A1 | 9/2005 | Forster et al. |
| 2005/0234546 A1 | 10/2005 | Nugent et al. |
| 2005/0240200 A1 | 10/2005 | Bergheim |
| 2005/0251209 A1 | 11/2005 | Saadat et al. |
| 2005/0256567 A1 | 11/2005 | Lim et al. |
| 2005/0283231 A1 | 12/2005 | Haug et al. |
| 2005/0288766 A1 | 12/2005 | Plain et al. |
| 2006/0004442 A1 | 1/2006 | Spenser et al. |
| 2006/0025784 A1 | 2/2006 | Starksen et al. |
| 2006/0025857 A1 | 2/2006 | Bergheim et al. |
| 2006/0030885 A1 | 2/2006 | Hyde |
| 2006/0042803 A1 | 3/2006 | Gallaher |
| 2006/0047338 A1 | 3/2006 | Jenson et al. |
| 2006/0052868 A1 | 3/2006 | Mortier et al. |
| 2006/0058872 A1 | 3/2006 | Salahieh et al. |
| 2006/0094983 A1 | 5/2006 | Burbank et al. |
| 2006/0129025 A1 | 6/2006 | Levine et al. |
| 2006/0142784 A1 | 6/2006 | Kontos |
| 2006/0161040 A1 | 7/2006 | McCarthy et al. |
| 2006/0161249 A1 | 7/2006 | Realyvasquez et al. |
| 2006/0167541 A1 | 7/2006 | Lattouf |
| 2006/0195134 A1 | 8/2006 | Crittenden |
| 2006/0195183 A1 | 8/2006 | Navia et al. |
| 2006/0229708 A1 | 10/2006 | Powell et al. |
| 2006/0229719 A1 | 10/2006 | Marquez et al. |
| 2006/0241745 A1 | 10/2006 | Solem |
| 2006/0247491 A1 | 11/2006 | Vidlund et al. |
| 2006/0252984 A1 | 11/2006 | Rahdert et al. |
| 2006/0259135 A1 | 11/2006 | Navia et al. |
| 2006/0259136 A1 | 11/2006 | Nguyen et al. |
| 2006/0259137 A1 | 11/2006 | Artof et al. |
| 2006/0271172 A1 | 11/2006 | Tehrani |
| 2006/0276874 A1 | 12/2006 | Wilson et al. |
| 2006/0282161 A1 | 12/2006 | Huynh et al. |
| 2006/0287716 A1 | 12/2006 | Banbury et al. |
| 2006/0287717 A1 | 12/2006 | Rowe et al. |
| 2007/0005131 A1 | 1/2007 | Taylor |
| 2007/0005231 A1 | 1/2007 | Seguchi |
| 2007/0010877 A1 | 1/2007 | Salahieh et al. |
| 2007/0016286 A1 | 1/2007 | Herrmann et al. |
| 2007/0016288 A1 | 1/2007 | Gurskis et al. |
| 2007/0027535 A1 | 2/2007 | Purdy et al. |
| 2007/0038291 A1 | 2/2007 | Case et al. |
| 2007/0050020 A1 | 3/2007 | Spence |
| 2007/0061010 A1 | 3/2007 | Hauser et al. |
| 2007/0066863 A1 | 3/2007 | Rafiee et al. |
| 2007/0073387 A1 | 3/2007 | Forster et al. |
| 2007/0078297 A1 | 4/2007 | Rafiee et al. |
| 2007/0083076 A1 | 4/2007 | Lichtenstein |
| 2007/0083259 A1 | 4/2007 | Bloom et al. |
| 2007/0093890 A1 | 4/2007 | Eliasen et al. |
| 2007/0100439 A1 | 5/2007 | Cangialosi et al. |
| 2007/0112422 A1 | 5/2007 | Dehdashtian |
| 2007/0112425 A1 | 5/2007 | Schaller et al. |
| 2007/0118151 A1 | 5/2007 | Davidson |
| 2007/0118154 A1 | 5/2007 | Crabtree |
| 2007/0118210 A1 | 5/2007 | Pinchuk |
| 2007/0118213 A1 | 5/2007 | Loulmet |
| 2007/0142906 A1 | 6/2007 | Figulla et al. |
| 2007/0161846 A1 | 7/2007 | Nikolic et al. |
| 2007/0162048 A1 | 7/2007 | Quinn et al. |
| 2007/0162103 A1 | 7/2007 | Case et al. |
| 2007/0168024 A1 | 7/2007 | Khairkhahan |
| 2007/0185565 A1 | 8/2007 | Schwammenthal et al. |
| 2007/0185571 A1 | 8/2007 | Kapadia et al. |
| 2007/0203575 A1 | 8/2007 | Forster et al. |
| 2007/0213813 A1 | 9/2007 | Von Segesser et al. |
| 2007/0215362 A1 | 9/2007 | Rodgers |
| 2007/0221388 A1 | 9/2007 | Johnson |
| 2007/0233239 A1 | 10/2007 | Navia et al. |
| 2007/0239265 A1 | 10/2007 | Birdsall |
| 2007/0255394 A1 | 11/2007 | Ryan |
| 2007/0256843 A1 | 11/2007 | Pahila |
| 2007/0265658 A1 | 11/2007 | Nelson et al. |
| 2007/0267202 A1 | 11/2007 | Mariller |
| 2007/0270932 A1 | 11/2007 | Headley et al. |
| 2007/0270943 A1 | 11/2007 | Solem |
| 2007/0293944 A1 | 12/2007 | Spenser et al. |
| 2008/0009940 A1 | 1/2008 | Cribier |
| 2008/0033543 A1 | 2/2008 | Gurskis et al. |
| 2008/0039934 A1 | 2/2008 | Styrc |
| 2008/0065011 A1 | 3/2008 | Marchand et al. |
| 2008/0071361 A1 | 3/2008 | Tuval et al. |
| 2008/0071362 A1 | 3/2008 | Tuval et al. |
| 2008/0071363 A1 | 3/2008 | Tuval et al. |
| 2008/0071366 A1 | 3/2008 | Tuval et al. |
| 2008/0071368 A1 | 3/2008 | Tuval et al. |
| 2008/0071369 A1 | 3/2008 | Tuval et al. |
| 2008/0082163 A1 | 4/2008 | Woo |
| 2008/0082166 A1 | 4/2008 | Styrc et al. |
| 2008/0091264 A1 | 4/2008 | Machold et al. |
| 2008/0114442 A1 | 5/2008 | Mitchell et al. |
| 2008/0125861 A1 | 5/2008 | Webler et al. |
| 2008/0147179 A1 | 6/2008 | Cai et al. |
| 2008/0154355 A1 | 6/2008 | Benichou et al. |
| 2008/0154356 A1 | 6/2008 | Obermiller et al. |
| 2008/0161911 A1 | 7/2008 | Revuelta et al. |
| 2008/0172035 A1 | 7/2008 | Starksen et al. |
| 2008/0177381 A1 | 7/2008 | Navia et al. |
| 2008/0183203 A1 | 7/2008 | Fitzgerald et al. |
| 2008/0183273 A1 | 7/2008 | Mesana et al. |
| 2008/0188928 A1 | 8/2008 | Salahieh et al. |
| 2008/0208328 A1 | 8/2008 | Antocci et al. |
| 2008/0208332 A1 | 8/2008 | Lamphere et al. |
| 2008/0221672 A1 | 9/2008 | Lamphere et al. |
| 2008/0243150 A1 | 10/2008 | Starksen et al. |
| 2008/0243245 A1 | 10/2008 | Thambar et al. |
| 2008/0255660 A1 | 10/2008 | Guyenot et al. |
| 2008/0255661 A1 | 10/2008 | Straubinger et al. |
| 2008/0281411 A1 | 11/2008 | Berreklouw |
| 2008/0288060 A1 | 11/2008 | Kaye et al. |
| 2008/0293996 A1 | 11/2008 | Evans et al. |
| 2009/0005863 A1 | 1/2009 | Goetz et al. |
| 2009/0048668 A1 | 2/2009 | Wilson et al. |
| 2009/0054968 A1 | 2/2009 | Bonhoeffer et al. |
| 2009/0054974 A1 | 2/2009 | McGuckin, Jr. et al. |
| 2009/0062908 A1 | 3/2009 | Bonhoeffer et al. |
| 2009/0076598 A1 | 3/2009 | Salahieh et al. |
| 2009/0082619 A1 | 3/2009 | De Marchena |
| 2009/0088836 A1 | 4/2009 | Bishop et al. |
| 2009/0099410 A1 | 4/2009 | De Marchena |
| 2009/0112309 A1 | 4/2009 | Jaramillo |
| 2009/0131849 A1 | 5/2009 | Maurer et al. |
| 2009/0132035 A1 | 5/2009 | Roth et al. |
| 2009/0137861 A1 | 5/2009 | Goldberg et al. |
| 2009/0138079 A1 | 5/2009 | Tuval et al. |
| 2009/0157175 A1 | 6/2009 | Benichou |
| 2009/0164005 A1 | 6/2009 | Dove et al. |
| 2009/0171432 A1 | 7/2009 | Von Segesser et al. |
| 2009/0171447 A1 | 7/2009 | Von Segesser et al. |
| 2009/0171456 A1 | 7/2009 | Kveen et al. |
| 2009/0177266 A1 | 7/2009 | Powell et al. |
| 2009/0192601 A1 | 7/2009 | Rafiee et al. |
| 2009/0210052 A1 | 8/2009 | Forster et al. |
| 2009/0216322 A1 | 8/2009 | Le et al. |
| 2009/0222076 A1 | 9/2009 | Figulla et al. |

(56) References Cited

U.S. PATENT DOCUMENTS

| | | |
|---|---|---|
| 2009/0224529 A1 | 9/2009 | Gill |
| 2009/0234318 A1 | 9/2009 | Loulmet et al. |
| 2009/0234435 A1 | 9/2009 | Johnson et al. |
| 2009/0234443 A1 | 9/2009 | Ottma et al. |
| 2009/0240320 A1 | 9/2009 | Tuval et al. |
| 2009/0248149 A1 | 10/2009 | Gabbay |
| 2009/0276040 A1 | 11/2009 | Rowe et al. |
| 2009/0281619 A1 | 11/2009 | Le et al. |
| 2009/0287299 A1 | 11/2009 | Tabor et al. |
| 2009/0292262 A1 | 11/2009 | Adams et al. |
| 2009/0319037 A1 | 12/2009 | Rowe et al. |
| 2009/0326575 A1 | 12/2009 | Galdonik et al. |
| 2010/0016958 A1 | 1/2010 | St. Goar et al. |
| 2010/0021382 A1 | 1/2010 | Dorshow et al. |
| 2010/0023117 A1 | 1/2010 | Yoganathan et al. |
| 2010/0036479 A1 | 2/2010 | Hill et al. |
| 2010/0049313 A1 | 2/2010 | Alon et al. |
| 2010/0082094 A1 | 4/2010 | Quadri et al. |
| 2010/0161041 A1 | 6/2010 | Maisano et al. |
| 2010/0168839 A1 | 7/2010 | Braido et al. |
| 2010/0179641 A1 | 7/2010 | Ryan et al. |
| 2010/0185277 A1 | 7/2010 | Braido et al. |
| 2010/0185278 A1 | 7/2010 | Schankereli |
| 2010/0191326 A1 | 7/2010 | Alkhatib |
| 2010/0192402 A1 | 8/2010 | Yamaguchi et al. |
| 2010/0204781 A1 | 8/2010 | Alkhatib |
| 2010/0210899 A1 | 8/2010 | Schankereli |
| 2010/0217382 A1 | 8/2010 | Chau et al. |
| 2010/0249489 A1 | 9/2010 | Jarvik |
| 2010/0249923 A1 | 9/2010 | Alkhatib et al. |
| 2010/0280604 A1 | 11/2010 | Zipory et al. |
| 2010/0286768 A1 | 11/2010 | Alkhatib |
| 2010/0298755 A1 | 11/2010 | McNamara et al. |
| 2010/0298931 A1 | 11/2010 | Quadri et al. |
| 2011/0004296 A1 | 1/2011 | Lutter et al. |
| 2011/0015616 A1 | 1/2011 | Straubinger et al. |
| 2011/0015728 A1 | 1/2011 | Jimenez et al. |
| 2011/0015729 A1 | 1/2011 | Jimenez et al. |
| 2011/0029072 A1 | 2/2011 | Gabbay |
| 2011/0066231 A1 | 3/2011 | Cartledge et al. |
| 2011/0066233 A1 | 3/2011 | Thornton et al. |
| 2011/0112632 A1 | 5/2011 | Chau et al. |
| 2011/0137397 A1 | 6/2011 | Chau et al. |
| 2011/0137408 A1 | 6/2011 | Bergheim |
| 2011/0208297 A1 | 8/2011 | Tuval et al. |
| 2011/0224655 A1 | 9/2011 | Asirvatham et al. |
| 2011/0224678 A1 | 9/2011 | Gabbay |
| 2011/0224728 A1 | 9/2011 | Martin et al. |
| 2011/0224784 A1 | 9/2011 | Quinn |
| 2011/0245911 A1 | 10/2011 | Quill et al. |
| 2011/0251682 A1 | 10/2011 | Murray, III et al. |
| 2011/0264191 A1 | 10/2011 | Rothstein |
| 2011/0264206 A1 | 10/2011 | Tabor |
| 2011/0288637 A1 | 11/2011 | De Marchena |
| 2011/0319988 A1 | 12/2011 | Schankereli et al. |
| 2011/0319989 A1 | 12/2011 | Lane et al. |
| 2012/0010694 A1 | 1/2012 | Lutter et al. |
| 2012/0016464 A1 | 1/2012 | Seguin |
| 2012/0016468 A1 | 1/2012 | Robin et al. |
| 2012/0022633 A1 | 1/2012 | Olson et al. |
| 2012/0022640 A1 | 1/2012 | Gross et al. |
| 2012/0035703 A1 | 2/2012 | Lutter et al. |
| 2012/0035713 A1 | 2/2012 | Lutter et al. |
| 2012/0035722 A1 | 2/2012 | Tuval |
| 2012/0053686 A1 | 3/2012 | McNamara et al. |
| 2012/0059458 A1 | 3/2012 | Buchbinder et al. |
| 2012/0059487 A1 | 3/2012 | Cunanan et al. |
| 2012/0089171 A1 | 4/2012 | Hastings et al. |
| 2012/0101571 A1 | 4/2012 | Thambar et al. |
| 2012/0101572 A1 | 4/2012 | Kovalsky et al. |
| 2012/0116351 A1 | 5/2012 | Chomas et al. |
| 2012/0123529 A1 | 5/2012 | Levi et al. |
| 2012/0158129 A1 | 6/2012 | Duffy et al. |
| 2012/0165930 A1 | 6/2012 | Gifford et al. |
| 2012/0179244 A1* | 7/2012 | Schankereli .......... A61F 2/2418 623/2.11 |
| 2012/0203336 A1 | 8/2012 | Annest |
| 2012/0215303 A1 | 8/2012 | Quadri et al. |
| 2012/0226348 A1 | 9/2012 | Lane et al. |
| 2012/0283824 A1 | 11/2012 | Lutter et al. |
| 2012/0289945 A1 | 11/2012 | Segermark |
| 2013/0030522 A1 | 1/2013 | Rowe et al. |
| 2013/0053950 A1 | 2/2013 | Rowe et al. |
| 2013/0066341 A1 | 3/2013 | Ketai et al. |
| 2013/0079873 A1 | 3/2013 | Migliazza et al. |
| 2013/0131788 A1 | 5/2013 | Quadri et al. |
| 2013/0172978 A1 | 7/2013 | Vidlund et al. |
| 2013/0184811 A1 | 7/2013 | Rowe et al. |
| 2013/0190860 A1 | 7/2013 | Sundt, III |
| 2013/0190861 A1 | 7/2013 | Chau et al. |
| 2013/0197622 A1 | 8/2013 | Mitra et al. |
| 2013/0226288 A1 | 8/2013 | Goldwasser et al. |
| 2013/0231735 A1 | 9/2013 | Deem et al. |
| 2013/0274874 A1 | 10/2013 | Hammer |
| 2013/0282101 A1 | 10/2013 | Eidenschink et al. |
| 2013/0310928 A1 | 11/2013 | Morriss et al. |
| 2013/0317603 A1 | 11/2013 | McLean et al. |
| 2013/0325041 A1 | 12/2013 | Annest et al. |
| 2013/0325110 A1 | 12/2013 | Khalil et al. |
| 2013/0338752 A1 | 12/2013 | Geusen et al. |
| 2014/0046433 A1 | 2/2014 | Kovalsky |
| 2014/0081323 A1 | 3/2014 | Hawkins |
| 2014/0094918 A1 | 4/2014 | Vishnubholta et al. |
| 2014/0142691 A1 | 5/2014 | Pouletty |
| 2014/0163668 A1 | 6/2014 | Rafiee |
| 2014/0194981 A1 | 7/2014 | Menk et al. |
| 2014/0194983 A1 | 7/2014 | Kovalsky et al. |
| 2014/0214159 A1 | 7/2014 | Vidlund et al. |
| 2014/0222142 A1 | 8/2014 | Kovalsky et al. |
| 2014/0243966 A1 | 8/2014 | Garde et al. |
| 2014/0277419 A1 | 9/2014 | Garde et al. |
| 2014/0296969 A1 | 10/2014 | Tegels et al. |
| 2014/0296970 A1 | 10/2014 | Ekvall et al. |
| 2014/0296971 A1 | 10/2014 | Tegels et al. |
| 2014/0296972 A1 | 10/2014 | Tegels et al. |
| 2014/0296975 A1 | 10/2014 | Tegels et al. |
| 2014/0303718 A1 | 10/2014 | Tegels et al. |
| 2014/0309732 A1 | 10/2014 | Solem |
| 2014/0316516 A1 | 10/2014 | Vidlund et al. |
| 2014/0324160 A1 | 10/2014 | Benichou et al. |
| 2014/0324161 A1 | 10/2014 | Tegels et al. |
| 2014/0324164 A1 | 10/2014 | Gross et al. |
| 2014/0331475 A1 | 11/2014 | Duffy et al. |
| 2014/0358224 A1 | 12/2014 | Tegels et al. |
| 2014/0364942 A1 | 12/2014 | Straubinger et al. |
| 2014/0364944 A1 | 12/2014 | Lutter et al. |
| 2014/0379076 A1 | 12/2014 | Vidlund et al. |
| 2015/0005874 A1 | 1/2015 | Vidlund et al. |
| 2015/0011821 A1 | 1/2015 | Gorman et al. |
| 2015/0025553 A1 | 1/2015 | Del Nido et al. |
| 2015/0057705 A1 | 2/2015 | Vidlund et al. |
| 2015/0073542 A1 | 3/2015 | Heldman |
| 2015/0073545 A1 | 3/2015 | Braido |
| 2015/0094802 A1 | 4/2015 | Buchbinder et al. |
| 2015/0105856 A1 | 4/2015 | Rowe et al. |
| 2015/0119936 A1 | 4/2015 | Gilmore et al. |
| 2015/0119978 A1 | 4/2015 | Tegels et al. |
| 2015/0127093 A1 | 5/2015 | Hosmer et al. |
| 2015/0127096 A1 | 5/2015 | Rowe et al. |
| 2015/0134050 A1 | 5/2015 | Solem et al. |
| 2015/0142100 A1 | 5/2015 | Morriss et al. |
| 2015/0142101 A1 | 5/2015 | Coleman et al. |
| 2015/0142103 A1 | 5/2015 | Vidlund |
| 2015/0142104 A1 | 5/2015 | Braido |
| 2015/0173897 A1 | 6/2015 | Raanani et al. |
| 2015/0196393 A1 | 7/2015 | Vidlund et al. |
| 2015/0196688 A1 | 7/2015 | James et al. |
| 2015/0202044 A1 | 7/2015 | Chau et al. |
| 2015/0216653 A1 | 8/2015 | Freudenthal |
| 2015/0216660 A1 | 8/2015 | Pintor et al. |
| 2015/0223820 A1 | 8/2015 | Olson et al. |
| 2015/0223934 A1 | 8/2015 | Vidlund et al. |
| 2015/0238312 A1 | 8/2015 | Lashinski |

(56) References Cited

U.S. PATENT DOCUMENTS

| | | |
|---|---|---|
| 2015/0238729 A1 | 8/2015 | Jenson et al. |
| 2015/0265401 A1 | 9/2015 | Braido |
| 2015/0272731 A1 | 10/2015 | Racchini et al. |
| 2015/0305860 A1 | 10/2015 | Wang et al. |
| 2015/0305864 A1 | 10/2015 | Quadri et al. |
| 2015/0305868 A1 | 10/2015 | Lutter et al. |
| 2015/0327995 A1 | 11/2015 | Morin et al. |
| 2015/0328001 A1 | 11/2015 | McLean et al. |
| 2015/0335424 A1 | 11/2015 | McLean et al. |
| 2015/0335429 A1 | 11/2015 | Morriss et al. |
| 2015/0342717 A1 | 12/2015 | O'Donnell et al. |
| 2015/0351903 A1 | 12/2015 | Morriss et al. |
| 2015/0351906 A1 | 12/2015 | Hammer et al. |
| 2016/0000562 A1 | 1/2016 | Siegel |
| 2016/0008131 A1 | 1/2016 | Christianson et al. |
| 2016/0038280 A1 | 2/2016 | Morriss et al. |
| 2016/0067042 A1 | 3/2016 | Murad et al. |
| 2016/0074160 A1 | 3/2016 | Christianson et al. |
| 2016/0106537 A1 | 4/2016 | Christianson et al. |
| 2016/0113764 A1 | 4/2016 | Sheahan et al. |
| 2016/0143736 A1 | 5/2016 | Vidlund et al. |
| 2016/0151155 A1 | 6/2016 | Lutter et al. |
| 2016/0206280 A1 | 7/2016 | Vidlund et al. |
| 2016/0242902 A1 | 8/2016 | Morriss et al. |
| 2016/0262879 A1 | 9/2016 | Meiri et al. |
| 2016/0262881 A1 | 9/2016 | Schankereli et al. |
| 2016/0278955 A1 | 9/2016 | Liu et al. |
| 2016/0317290 A1 | 11/2016 | Chau et al. |
| 2016/0324635 A1 | 11/2016 | Vidlund et al. |
| 2016/0331527 A1 | 11/2016 | Vidlund et al. |
| 2016/0346086 A1 | 12/2016 | Solem |
| 2016/0367365 A1 | 12/2016 | Conklin |
| 2016/0367367 A1 | 12/2016 | Maisano et al. |
| 2016/0367368 A1 | 12/2016 | Vidlund et al. |
| 2017/0079790 A1 | 3/2017 | Vidlund et al. |
| 2017/0100248 A1 | 4/2017 | Tegels et al. |
| 2017/0128208 A1 | 5/2017 | Christianson et al. |
| 2017/0181854 A1 | 6/2017 | Christianson et al. |
| 2017/0196688 A1 | 7/2017 | Christianson et al. |
| 2017/0252153 A1 | 9/2017 | Chau et al. |
| 2017/0266001 A1 | 9/2017 | Vidlund et al. |
| 2017/0281343 A1 | 10/2017 | Christianson et al. |
| 2017/0312076 A1 | 11/2017 | Lutter et al. |
| 2017/0312077 A1 | 11/2017 | Vidlund et al. |
| 2017/0319333 A1 | 11/2017 | Tegels et al. |
| 2018/0028314 A1 | 2/2018 | Ekvall et al. |
| 2018/0078368 A1 | 3/2018 | Vidlund et al. |
| 2018/0078370 A1 | 3/2018 | Kovalsky et al. |
| 2018/0147055 A1 | 5/2018 | Vidlund et al. |
| 2018/0193138 A1 | 7/2018 | Vidlund |
| 2018/0263618 A1 | 9/2018 | Vidlund et al. |
| 2018/0271653 A1 | 9/2018 | Vidlund et al. |

FOREIGN PATENT DOCUMENTS

| | | |
|---|---|---|
| CN | 2902226 | 5/2007 |
| CN | 101146484 | 3/2008 |
| CN | 101180010 | 5/2008 |
| CN | 101984938 | 3/2011 |
| CN | 102869317 | 1/2013 |
| CN | 102869318 | 1/2013 |
| CN | 102869321 | 1/2013 |
| CN | 103220993 | 7/2013 |
| CN | 102639179 B | 10/2014 |
| DE | 2246526 | 3/1973 |
| DE | 19532846 | 3/1997 |
| DE | 19546692 | 6/1997 |
| DE | 19857887 | 7/2000 |
| DE | 19907646 | 8/2000 |
| DE | 10049812 | 4/2002 |
| DE | 10049813 | 4/2002 |
| DE | 10049815 | 4/2002 |
| DE | 102006052564 | 12/2007 |
| DE | 102006052710 | 5/2008 |
| DE | 102007043830 A1 | 4/2009 |
| DE | 102007043831 | 4/2009 |
| EP | 0103546 | 5/1988 |
| EP | 1057460 | 12/2000 |
| EP | 1088529 | 4/2001 |
| EP | 1469797 | 11/2005 |
| EP | 2111800 | 10/2009 |
| EP | 2193762 | 6/2010 |
| EP | 2747707 | 4/2015 |
| EP | 2918248 | 9/2015 |
| EP | 2278944 | 3/2016 |
| FR | 2788217 | 7/2000 |
| FR | 2815844 | 5/2002 |
| JP | 2003-505146 | 2/2003 |
| JP | 2005-515836 | 6/2005 |
| JP | 2009-514628 | 4/2009 |
| JP | 2009-519783 | 5/2009 |
| JP | 2013-512765 | 4/2013 |
| JP | 2013539395 A | 10/2013 |
| NL | 1017275 | 8/2002 |
| SU | 1271508 | 11/1986 |
| WO | WO 92/17118 | 10/1992 |
| WO | WO 93/01768 | 2/1993 |
| WO | WO 98/29057 | 7/1998 |
| WO | WO 99/40964 | 8/1999 |
| WO | WO 99/47075 | 9/1999 |
| WO | WO 2000/018333 | 4/2000 |
| WO | WO 2000/030550 | 6/2000 |
| WO | WO 2000/041652 | 7/2000 |
| WO | WO 2000/047139 | 8/2000 |
| WO | WO 2001/035878 | 5/2001 |
| WO | WO 2001/049213 | 7/2001 |
| WO | WO 2001/054624 | 8/2001 |
| WO | WO 2001/054625 | 8/2001 |
| WO | WO 2001/056512 | 8/2001 |
| WO | WO 2001/061289 | 8/2001 |
| WO | WO 2001/076510 | 10/2001 |
| WO | WO 2001/082840 | 11/2001 |
| WO | WO 2002/004757 | 1/2002 |
| WO | WO 2002/022054 | 3/2002 |
| WO | WO 2002/028321 | 4/2002 |
| WO | WO 2002/036048 | 5/2002 |
| WO | WO 2002/041789 | 5/2002 |
| WO | WO 2002/043620 | 6/2002 |
| WO | WO 2002/049540 | 6/2002 |
| WO | WO 2002/076348 | 10/2002 |
| WO | WO 2003/003943 | 1/2003 |
| WO | WO 2003/030776 | 4/2003 |
| WO | WO 2003/047468 | 6/2003 |
| WO | WO 2003/049619 | 6/2003 |
| WO | WO 2004/019825 | 3/2004 |
| WO | WO 2005/102181 | 11/2005 |
| WO | WO 2006/014233 | 2/2006 |
| WO | WO 2006/034008 | 3/2006 |
| WO | WO 2006/064490 | 6/2006 |
| WO | WO 2006/070372 | 7/2006 |
| WO | WO 2006/105009 | 10/2006 |
| WO | WO 2006/113906 | 10/2006 |
| WO | WO 2006/127756 | 11/2006 |
| WO | WO 2007/081412 | 7/2007 |
| WO | WO 2007/100408 | 9/2007 |
| WO | WO 2008/005405 | 1/2008 |
| WO | WO 2008/035337 | 3/2008 |
| WO | WO 2008/091515 | 7/2008 |
| WO | WO 2008/125906 | 10/2008 |
| WO | WO 2008/147964 | 12/2008 |
| WO | WO 2009/024859 | 2/2009 |
| WO | WO 2009/026563 | 2/2009 |
| WO | WO 2009/045338 | 4/2009 |
| WO | WO 2009/132187 | 10/2009 |
| WO | WO 2010/090878 | 8/2010 |
| WO | WO 2010/098857 | 9/2010 |
| WO | WO 2010/121076 | 10/2010 |
| WO | WO 2011/017440 | 2/2011 |
| WO | WO 2011/022658 | 2/2011 |
| WO | WO 2011/069048 | 6/2011 |
| WO | WO 2011/072084 | 6/2011 |
| WO | WO 2011/106735 | 9/2011 |
| WO | WO 2011/109813 | 9/2011 |
| WO | WO 2011/159342 | 12/2011 |

(56) References Cited

FOREIGN PATENT DOCUMENTS

| | | |
|---|---|---|
| WO | WO 2011/163275 | 12/2011 |
| WO | WO 2012/027487 | 3/2012 |
| WO | WO 2012/036742 | 3/2012 |
| WO | WO 2012/095116 | 7/2012 |
| WO | WO 2012/177942 | 12/2012 |
| WO | WO 2013/021374 | 2/2013 |
| WO | WO 2013/045262 | 4/2013 |
| WO | WO 2013/059747 | 4/2013 |
| WO | WO 2013/096411 | 6/2013 |
| WO | WO 2013/175468 | 11/2013 |
| WO | WO 2014/121280 | 8/2014 |
| WO | WO 2014/144937 | 9/2014 |
| WO | WO 2014/162306 | 10/2014 |
| WO | WO 2014/189974 | 11/2014 |
| WO | 2014210124 A1 | 12/2014 |
| WO | WO 2015/051430 | 4/2015 |
| WO | WO 2015/058039 | 4/2015 |
| WO | WO 2015/063580 | 5/2015 |
| WO | WO 2015/065646 | 5/2015 |
| WO | WO 2015/120122 | 8/2015 |
| WO | WO 2015/138306 | 9/2015 |
| WO | WO 2015/173609 | 11/2015 |
| WO | WO 2016/112085 | 7/2016 |
| WO | WO 2016/126942 | 8/2016 |
| WO | WO 2016/168609 | 10/2016 |
| WO | WO 2016/196933 | 12/2016 |
| WO | WO 2017/096157 | 6/2017 |
| WO | WO 2017/132008 | 8/2017 |
| WO | WO 2017/218375 | 12/2017 |
| WO | WO 2018/005779 | 1/2018 |
| WO | WO 2018/013515 | 1/2018 |

OTHER PUBLICATIONS

International Search Report and Written Opinion for International Application No. PCT/IB2014/060821, dated Oct. 10, 2014, 10 pages.
Office Action for U.S. Appl. No. 14/219,591, dated Mar. 11, 2016, 18 pages.
Office Action for U.S. Appl. No. 14/255,687, dated Nov. 3, 2015, 6 pages.
Notification of the First Office Action for Chinese Application No. 201480058965.4, dated May 3, 2017, 7 pages.
Office Action for European Application No. 14786405.2, dated Mar. 3, 2017, 5 pages.
Office Action for European Application No. 14786405.2, dated Oct. 10, 2017, 5 pages.
International Search Report and Written Opinion for International Application No. PCT/US2014/058826, dated Jan. 20, 2015, 14 pages.
Al Zaibag, M. et al., "Percutaneous Balloon Valvotomy in Tricuspid Stenosis," British Heart Journal, Jan. 1987, 57(1):51-53.
Al-Khaja, N. et al., "Eleven Years' Experience with Carpentier-Edwards Biological Valves in Relation to Survival and Complications," European Journal of Cardiothoracic Surgery, Jun. 30, 1989, 3:305-311.
Almagor, Y. et al., "Balloon Expandable Stent Implantation in Stenotic Right Heart Valved Conduits," Journal of the American College of Cardiology, Nov. 1, 1990, 16(6):1310-1314.
Andersen, H. R. et al., "Transluminal implantation of artificial heart valves. Description of a new expandable aortic valve and initial results with implantation by catheter technique in closed chest pigs," European Heart Journal, 1992, 13(5):704-708.
Andersen, H. R., "History of Percutaneous Aortic Valve Prosthesis," Herz, Aug. 2009, 34(5):343-346.
Andersen, H. R., "Transluminal catheter implanted prosthetic heart valves," International Journal of Angiology, 1998, 7(2):102-106.
Ashton, R. C., Jr. et al., "Development of an Intraluminal Device for the Treatment of Aortic Regurgitation: Prototype and in Vitro Testing System," Journal of Thoracic and Cardiovascular Surgery, 1996, 112:979-983.
Benchimol, A. et al., "Simultaneous Left Ventricular Echocardiography and Aortic Blood Velocity During Rapid Right Ventricular Pacing in Man," The American Journal of the Medical Sciences, Jan.-Feb. 1977, 273(1):55-62.
Bernacca, G. M. et al., "Polyurethane heart valves: Fatigue failure, calcification, and polyurethane structure," Journal of Biomedical Materials Research, Mar. 5, 1997, 34(3):371-379.
Boudjemline, Y. et al., "Steps Toward the Percutaneous Replacement of Atrioventricular Valves: An Experimental Study," Journal of the American College of Cardiology, Jul. 2005, 46(2):360-365.
Buckberg, G. et al., "Restoring Papillary Muscle Dimensions During Restoration In Dilated Hearts," Interactive CardioVascular and Thoracic Surgery, 2005, 4:475-477.
Chamberlain, G., "Ceramics Replace Body Parts," Design News, Jun. 9, 1997, Issue 11, vol. 52, 5 pages.
Choo, S. J. et al., "Aortic Root Geometry: Pattern of Differences Between Leaflets and Sinuses of Valsava," The Journal of Heart Valve Disease, Jul. 1999, 8:407-415.
Declaration of Malcolm J. R. Dalrymple-Hay, Nov. 9, 2012, pp. 1-11; with Curriculum Vitae, Oct. 4, 2012.
Dotter, C. T. et al., "Transluminal Treatment of Arteriosclerotic Obstruction. Description of a New Technic and a Preliminary Report of its Application," Circulation, Nov. 1964, 30:654-670.
Drawbaugh, K., "Feature—Heart Surgeons Explore Minimally Invasive Methods," Reuters Limited, Jul. 16, 1996, 3 pages.
Gray, H., The Aorta, Anatomy of the Human Body, 1918, Retrieved from the Internet <http://www.bartleby.com/107/142.html>, Dec. 10, 2012, 5 pages.
Gray, H., The Heart, Anatomy of the Human Body, 1918, Retrieved from the Internet <http://education.yahoo.com/reference/gray/subjects/subject/138>, Aug. 10, 2012, 9 pages.
Greenhalgh, E. S., "Design and characterization of a biomimetic prosthetic aortic heart valve," 1994, ProQuest Dissertations and Theses, Department of Fiber and Polymer Science, North Carolina State University at Raleigh, 159 pages.
Inoue, K. et al., "Clinical Application of Transvenous Mitral Commissurotomy by a New Balloon Catheter," The Journal of Thoracic and Cardiovascular Surgery, 1984, 87:394-402.
Jin, X. Y. et al., "Aortic Root Geometry and Stentless Porcine Valve Competence," Seminars in Thoracic and Cardiovascular Surgery, Oct. 1999, 11(4):145-150.
Knudsen, L. L. et al., "Catheter-implanted prosthetic heart valves. Transluminal catheter implantation of a new expandable artificial heart valve in the descending thoracic aorta in isolated vessels and closed chest pigs," The International Journal of Artificial Organs, 1993, 16(5):253-262.
Kolata, G., "Device That Opens Clogged Arteries Gets a Failing Grade in a New Study," New York Times [online], <http://www.nytimes.com/1991/01/03/health/device-that-opens-clogged-arteries-gets-a-faili . . . ,>, published Jan. 3, 1991, retrieved from the Internet on Feb. 5, 2016, 3 pages.
Lawrence, D. D., "Percutaneous Endovascular Graft: Experimental Evaluation," Radiology, 1987, 163:357-360.
Lozonschi, L., et al. "Transapical mitral valved stent implantation: A survival series in swine," The Journal of Thoracic and Cardiovascular Surgery, 140(2):422-426 (Aug. 2010) published online Mar. 12, 2010, 1 page.
Lutter, G. et al., "Mitral Valved Stent Implantation," European Journal of Cardio-Thoracic Surgery, 2010, 38:350-355, 2 pages.
Ma, L. et al., "Double-crowned valved stents for off-pump mitral valve replacement," European Journal of Cardio-Thoracic Surgery, Aug. 2005, 28(2):194-198.
Moazami, N. et al., "Transluminal aortic valve placement: A feasibility study with a newly designed collapsible aortic valve," ASAIO Journal, Sep./Oct. 1996, 42(5):M381-M385.
Orton, C., "Mitralseal: Hybrid Transcatheter Mitral Valve Replacement," Symposium: Small Animal Proceedings, 2011, pp. 311-312.
Orton, C., "Mitralseal: Hybrid Transcatheter Mitral Valve Replacement," Retrieved from the Internet: <http:/www.acvs.org/symposium/proceedings2011/data/papers/102.pdf>, pp. 311-312.
Pavcnik, D. et al. "Development and Initial Experimental Evaluation of a Prosthetic Aortic Valve for Transcatheter Placement," Radiology, 1992; 183:151-154.

(56) References Cited

OTHER PUBLICATIONS

Porstmann, W. et al., "Der Verschluβ des Ductus Arteriosus Persistens ohne Thorakotomie," Thoraxchirurgie Vaskuläre Chirurgie, Band 15, Heft 2, Stuttgart, Apr. 1967, pp. 199-203.
Rashkind, W. J., "Creation of an Atrial Septal Defect Without Thoracotomy," The Journal of the American Medical Association, Jun. 13, 1966, 196(11):173-174.
Rashkind, W. J., "Historical Aspects of Interventional Cardiology: Past, Present, Future," Texas Heart Institute Journal, Dec. 1986, 13(4):363-367.
Reul, H. et al., "The Geometry of the Aortic Root in Health, at Valve Disease and After Valve Replacement," J. Biomechanics, 1990, 23(2):181-191.
Rosch, J. et al., "The Birth, Early Years and Future of Interventional Radiology," J Vasc Interv Radiol., Jul. 2003, 4:841-853.
Ross, D. N., "Aortic Valve Surgery," Guy's Hospital, London, 1968, pp. 192-197.
Rousseau, E. P. M. et al., "A mechanical analysis of the closed Hancock heart valve prosthesis," Journal of Biomechanics, 1988, 21(7):545-562.
Sabbah, A. N. et al., "Mechanical Factors in the Degeneration of Porcine Bioprosthetic Valves: An Overview," Dec. 1989, Journal of Cardiac Surgery, 4(4):302-309.
Selby, J. B., "Experience with New Retrieval Forceps for Foreign Body Removal in the Vascular, Urinary, and Biliary Systems," Radiology, 1990, 176:535-538.
Serruys, P. W. et al., "Stenting of Coronary Arteries. Are we the Sorcerer's Apprentice?," European Heart Journal, Sep. 1989, 10(9):774-782.
"Shape Memory Alloys," Retrieved from the Internet: <http://webdocs.cs.ualberta.ca/~database/MEMS/sma.html>, Feb. 5, 2016, 3 pages.
Sigwart, U., "An Overview of Intravascular Stents: Old and New," Chapter 48, Interventional Cardiology, 2nd Edition, W.B. Saunders Company, Philadelphia, PA, © 1994, 1990, pp. 803-815.
Tofeig, M. et al., "Transcatheter Closure of a Mid-Muscular Ventricular Septal Defect with an Amplatzer VSD Occluder Device," Heart, 1999, 81:438-440.
Uchida, B. T. et al., "Modifications of Gianturco Expandable Wire Stents," Am. J. Roentgenol., May 1988, 150(5):1185-1187.
Watt, A. H. et al., "Intravenous Adenosine in the Treatment of the Supraventricular Tachycardia; a Dose-Ranging Study and Interaction with Dipyridamole," British Journal of Clinical Pharmacology, 1986, 21:227-230.
Webb, J. G. et al., "Percutaneous Aortic Valve Implantation Retrograde from the Femoral Artery," Circulation, 2006, 113:842-850.
Wheatley, D. J., "Valve Prostheses," Rob & Smith's Operative Surgery, Fourth Edition, 1986, pp. 415-424, Butterworths.
Yoganathan, A. P. et al., "The Current Status of Prosthetic Heart Valves," In Polymetric Materials and Artificial Organs, American Chemical Society, 1984, pp. 111-150.
Examination Report No. 1 for Australian Application No. 2014342935, dated Jun. 27, 2018, 3 pages.
Notice of Reasons for Rejection for Japanese Application No. 2016-522095, dated Jul. 17, 2018, 5 pages.
Office Action for U.S. Appl. No. 14/864,035, dated Jun. 11, 2018, 17 pages.

* cited by examiner

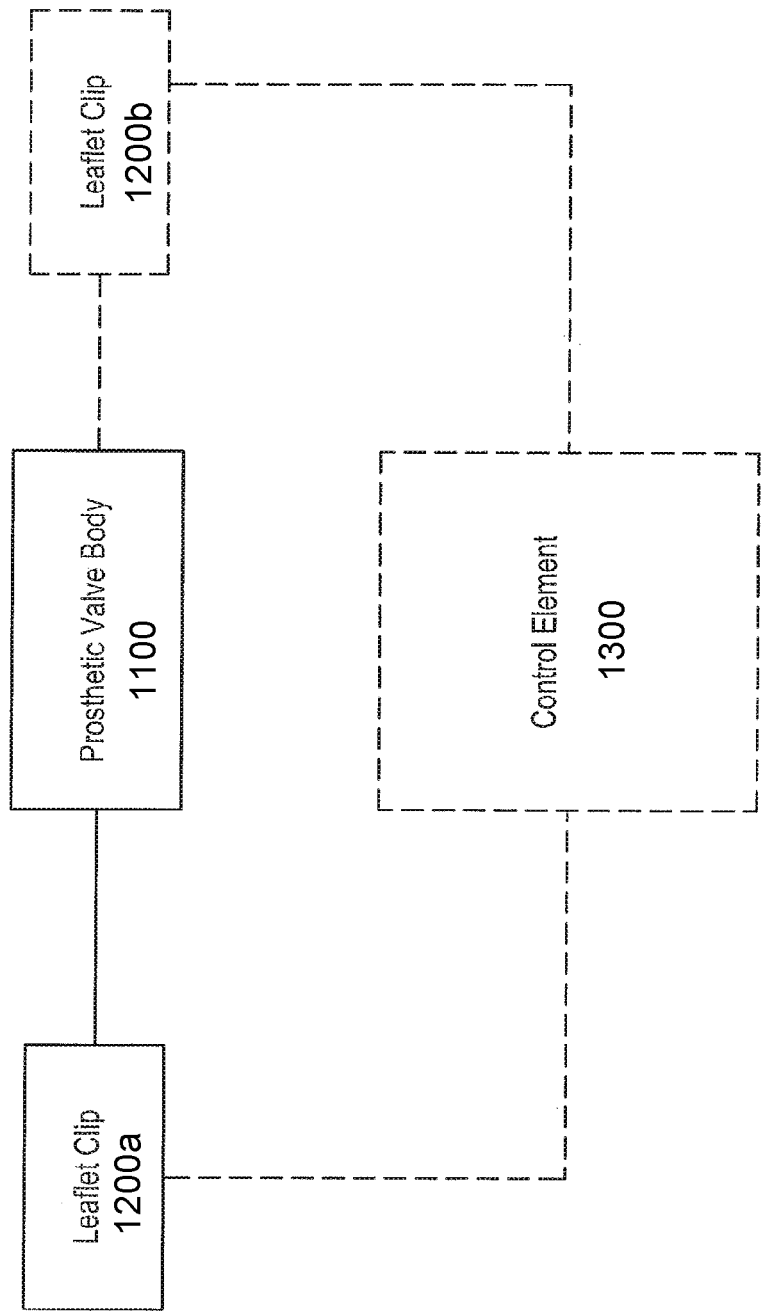

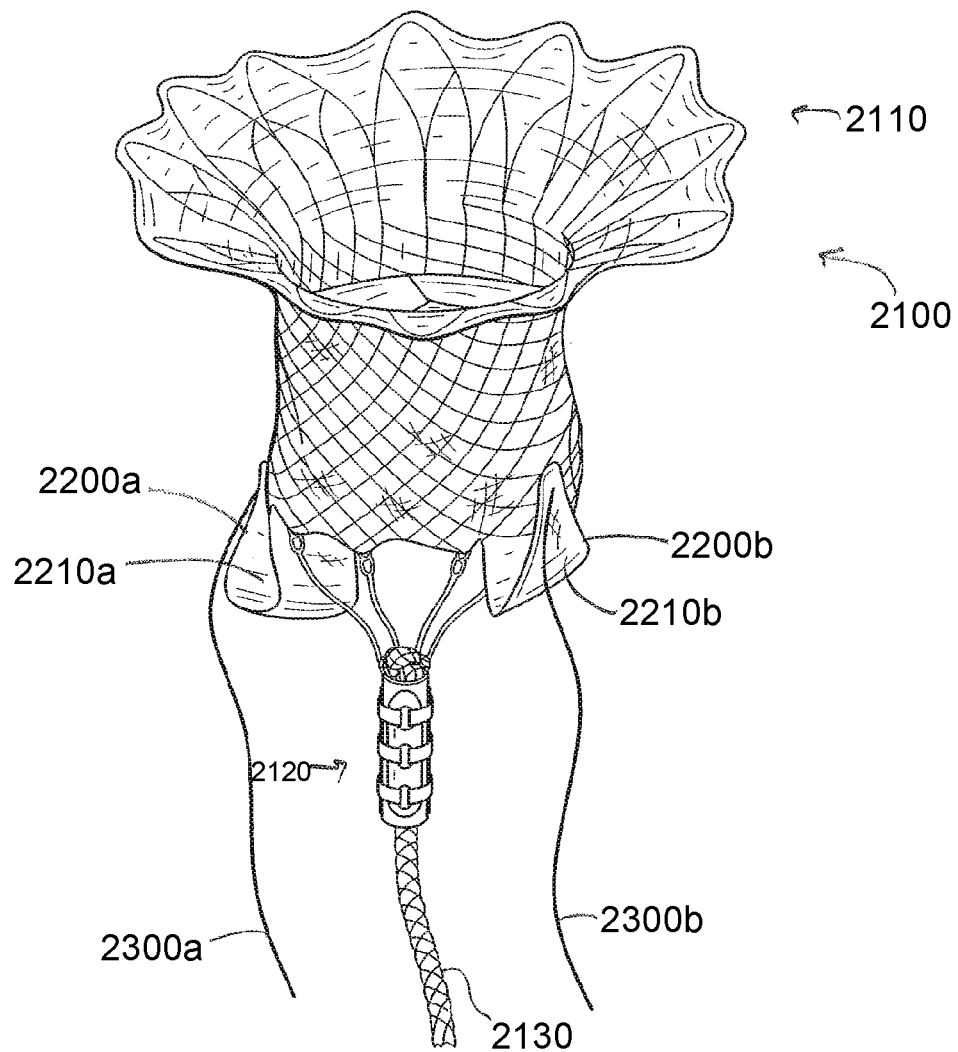

4200

4200

5000

8000

8000

8000

9000

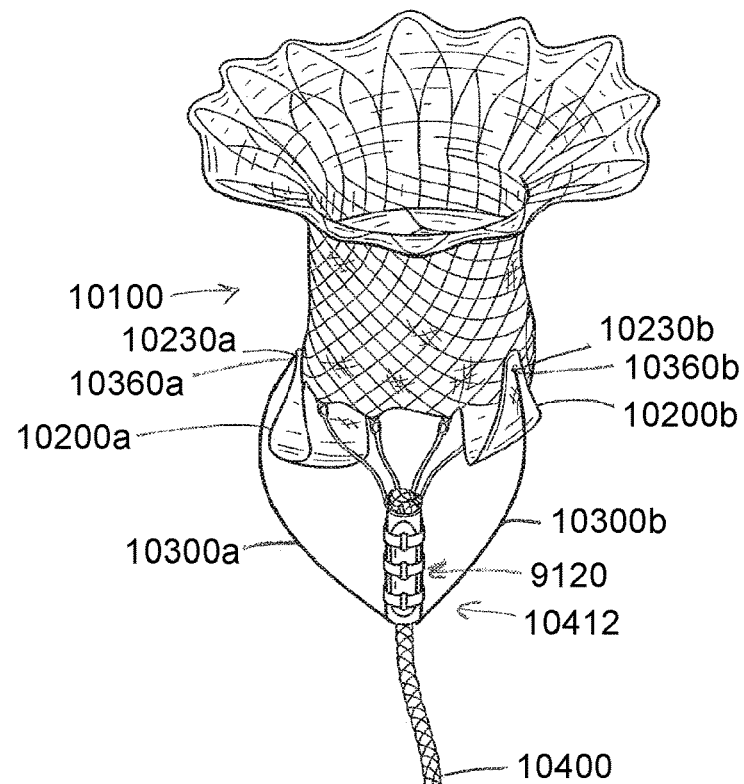
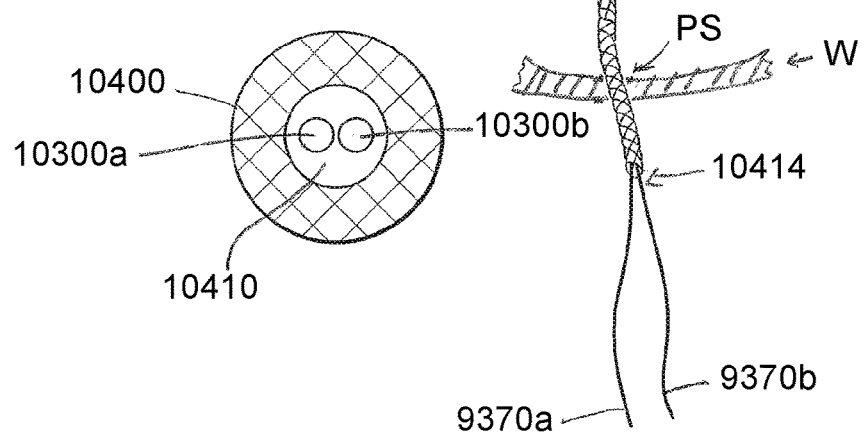

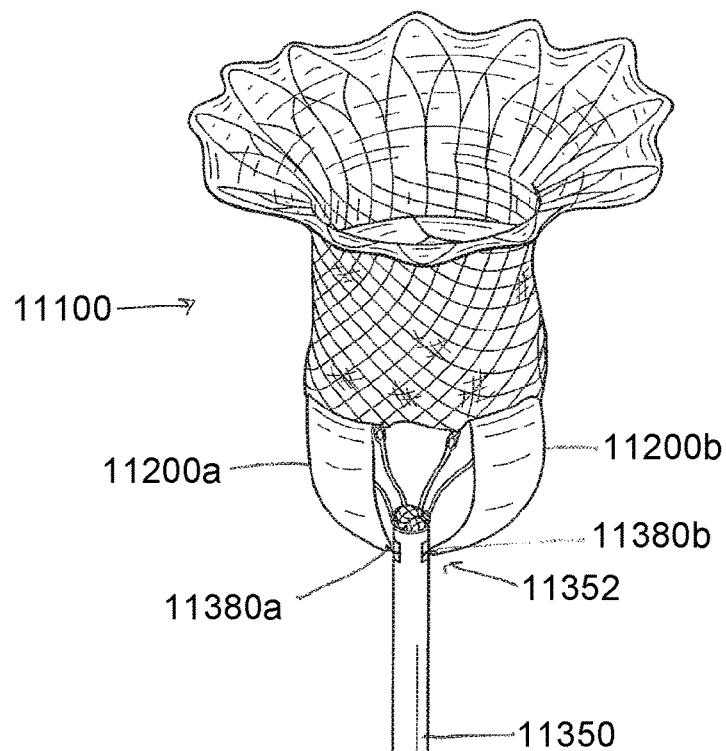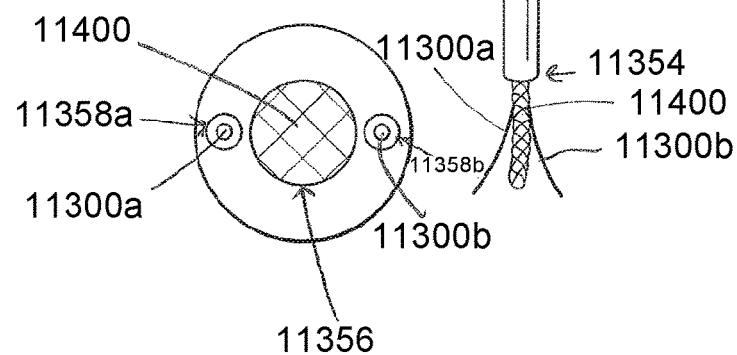

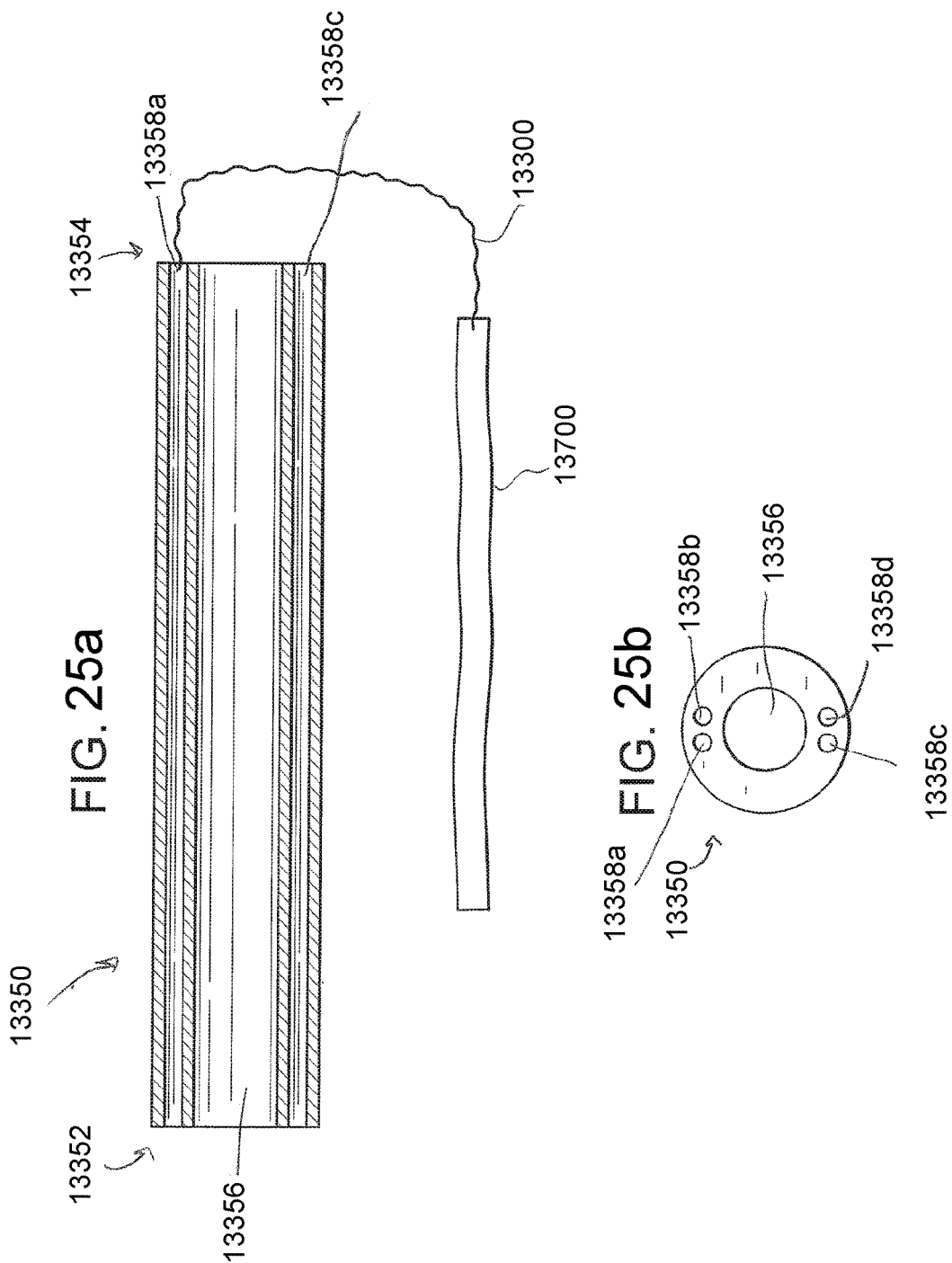

14800

15000

16000

16000

16000

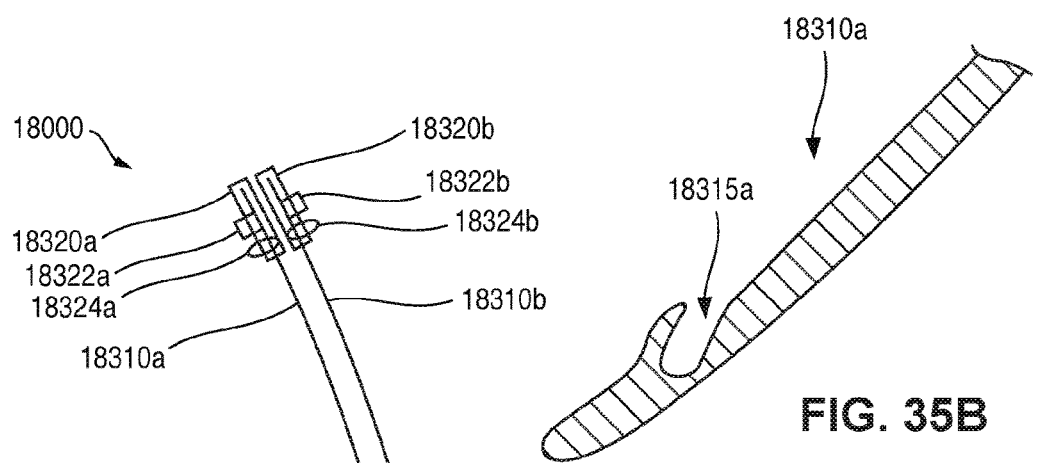
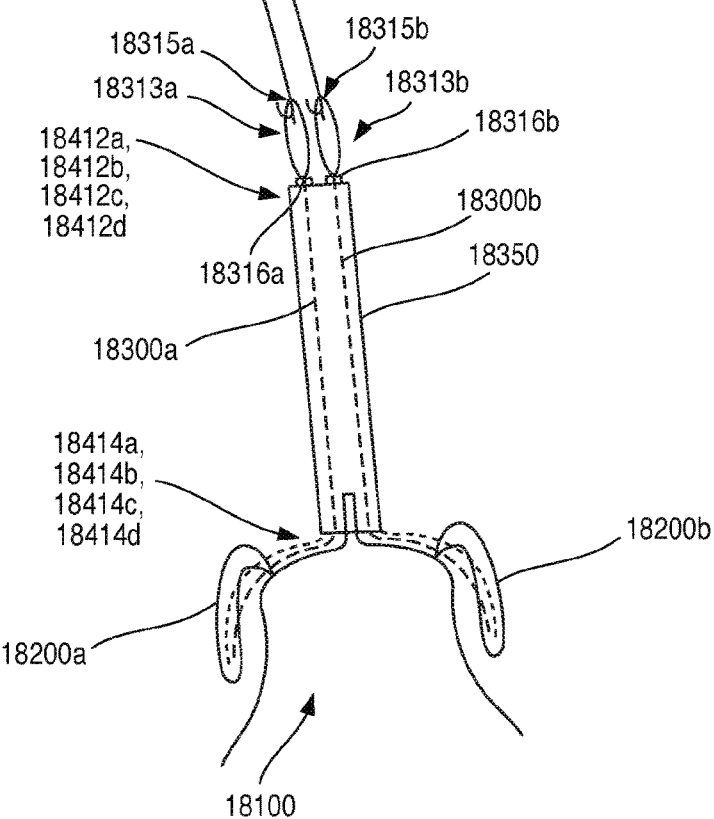
FIG. 35B
FIG. 35A

PROSTHETIC HEART VALVE AND SYSTEMS AND METHODS FOR DELIVERING THE SAME

CROSS-REFERENCE TO RELATED APPLICATIONS

This application claims priority to and the benefit from U.S. Provisional Patent Application No. 62/291,860, filed Feb. 5, 2016, entitled "Prosthetic Heart Valve and Systems and Methods for Delivering the Same," the entire disclosure of which is incorporated herein by reference in its entirety.

This application is also a continuation-in-part of U.S. patent application Ser. No. 14/864,035, filed Sep. 24, 2015, entitled "Prosthetic Heart Valve and Systems and Methods for Delivering the Same," which is a continuation under 35 USC Section 120 of International Application No. PCT/US2014/058826, filed Oct. 2, 2014, entitled "Prosthetic Heart Valve and Systems and Methods for Delivering the Same," which claims priority to and the benefit of U.S. Provisional Patent Application Ser. No. 61/896,574, filed Oct. 28, 2013, entitled "Improved Anterior Leaflet Clip Device for Prosthetic Mitral Valves" and U.S. Provisional Patent Application Ser. No. 62/049,662, filed Sep. 12, 2014, entitled "Improved Anterior Leaflet Clip Device for Prosthetic Mitral Valves," each of the disclosures of which is incorporated herein by reference in its entirety.

U.S. patent application Ser. No. 14/864,035 is also a continuation-in-part of U.S. patent application Ser. No. 14/154,546, filed Jan. 14, 2014, entitled "Anterior Leaflet Clip Device for Prosthetic Mitral Valve," which claims priority to and the benefit of U.S. Provisional Patent Application Ser. No. 61/807,695, filed Apr. 2, 2013, entitled "Anterior Leaflet Clip Device for Prosthetic Mitral Valve," each of the disclosures of which is incorporated by reference herein in its entirety.

BACKGROUND

Embodiments described herein relate generally to prosthetic heart valves, and apparatus, systems, and methods for delivering a prosthetic device into a heart. More particularly, embodiments described herein relate to apparatus, systems, and methods for implanting and manipulating a prosthetic heart valve and associated components into the heart.

The human heart is responsible for pumping blood around the human body. The human heart is separated into four distinct chambers, and is commonly referenced in terms of the right or left side of the heart. The right side of the heart, including the right atrium and the right ventricle, is responsible for receiving de-oxygenated blood from the body, and then pumping the de-oxygenated blood to the lungs in order to oxygenate the blood. The left side of the heart, including the left atrium and left ventricle, is responsible for receiving oxygenated blood from the lungs, and then pumping the oxygenated blood to various parts of the body. The movement of blood within the chambers of the heart is controlled by four valves: aortic, mitral, pulmonic and tricuspid. These valves open and close constantly, and as such, can be subject to wear and tear and other challenges that affect their performance (e.g., mitral valve regurgitation, prolapse, and/or stenosis), and consequently, the entire circulatory system.

Some known devices for repairing the performance of the heart, such as, for example, the performance of a mitral valve of the heart, can include a prosthetic heart valve. The prosthetic heart valve can be implanted and secured to a native annulus of the heart. In such cases, native leaflets of the heart valve can become disposed between the prosthetic heart valve and the myocardium of the heart. Further, when the native valve leaflets are disposed in such a manner, the native valve leaflets can, for example, interfere with blood flow into and out of the left ventricle of the heart (e.g., interfere with left ventricular outflow tract (LVOT), reduction of effective orifice area (EOA) through the prosthetic heart valve). In some cases, this can occur when the native valve leaflets become at least partially disposed in the flow path defined through the orifice area of the prosthetic heart valve and from the atrium to the ventricle of the heart. In addition, over time, the native valve leaflets can stiffen (e.g., change modulus) due to calcification or the like, resulting in undesirable turbulence, eddies, and/or otherwise undesirable flow profiles within the heart. Even more, such degradation and/or stiffening of the native valve leaflets can, in some cases, cause degradation of the prosthetic heart valve leaflets.

Accordingly, there is a need for improved devices, systems and methods for securing, capturing, controlling, or otherwise manipulating native valve leaflets of a heart valve when a prosthetic heart valve is disposed and operating therein.

SUMMARY

Apparatus, systems and methods for securing, capturing, controlling, or otherwise manipulating native heart valve leaflets when a prosthetic heart valve is delivered to, or disposed in, a native annulus of an atrioventricular valve of a heart are described herein. In some embodiments, a prosthetic heart valve includes a self-expanding wire frame body, a valve disposed in the body, a leaflet clip coupled to the body, and a control element operably coupled to the leaflet clip. The body has a proximal end and a distal end. The leaflet clip is configured to be transitioned between a first configuration in which the prosthetic valve can be inserted into a heart, and a second configuration in which the leaflet clip is disposed to capture a native valve leaflet between the leaflet clip and the wire frame body when the body is disposed in a native annulus of an atrioventricular valve of a heart. The control element has a length sufficient to extend from the leaflet clip through a ventricle of the heart and out a wall of the ventricle when the body is disposed in the native annulus of the atrioventricular valve of the heart. The control element is configured to allow a user to transition the leaflet clip from its first configuration to its second configuration when the body is disposed in the native annulus of the atrioventricular valve of the heart.

BRIEF DESCRIPTION OF THE DRAWINGS

FIG. 1 is a schematic illustration of a prosthetic heart valve according to an embodiment.

FIGS. 2a-2c show a prosthetic heart valve in a first position, second position and third position, respectively, according to an embodiment.

FIGS. 20a and 20b show a prosthetic heart valve and sectional top view of the same, according to an embodiment.

FIGS. 21a and 21b show a prosthetic heart valve and a section top view of the same, according to an embodiment.

FIGS. 25a and 25b show an elongate member in cross-section, and a control element and mandrel coupled thereto, and a top view of the elongate member, respectively, of the prosthetic heart valve of FIG. 24, according to an embodiment.

FIG. 35A shows a prosthetic heart valve system, according to an embodiment.

FIG. 35B shows a cross-sectional side view of a manipulator of the prosthetic heart valve system shown in FIG. 35A.

DETAILED DESCRIPTION

Figure 2A:
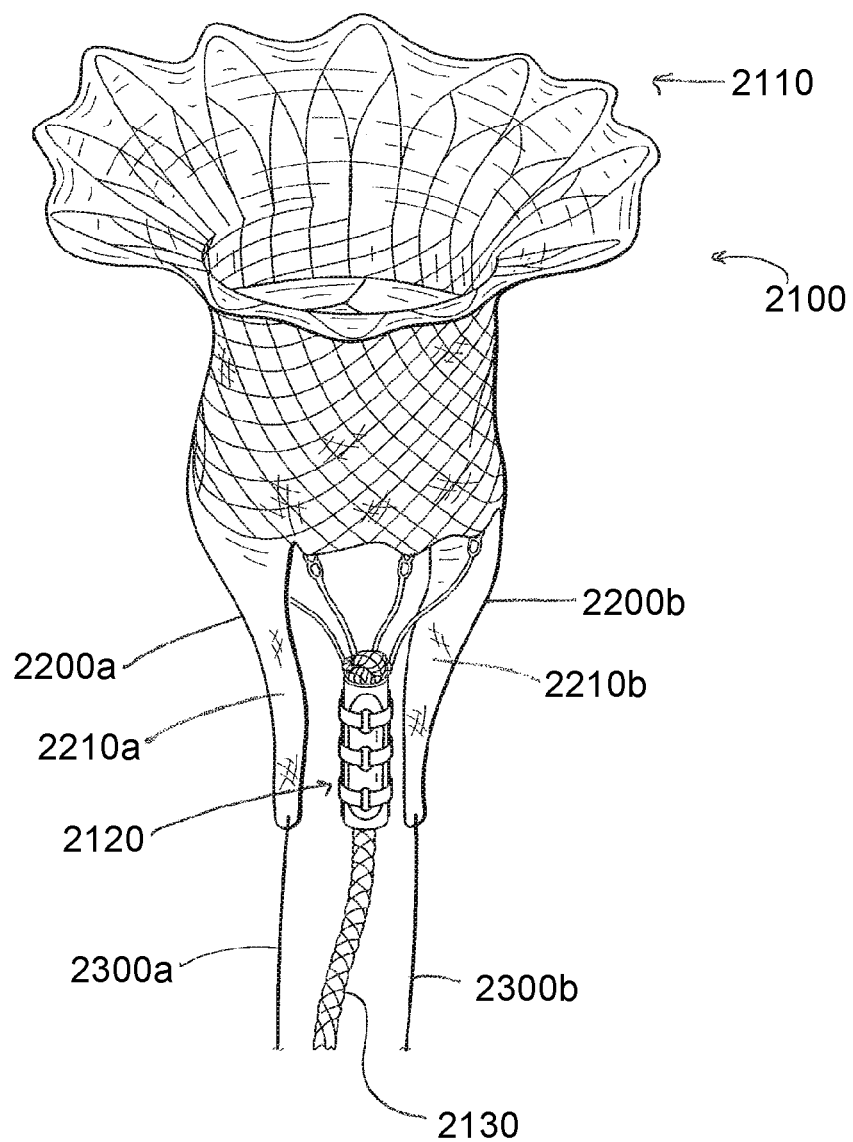

Apparatus, systems, and methods for securing, controlling, capturing, or otherwise manipulating native heart valve leaflets when a prosthetic heart valve is delivered to or disposed in a native annulus of an atrioventricular valve of a heart are described herein.

In some embodiments, a prosthetic heart valve (also referred to herein as a "prosthetic valve") includes a self-expanding wire frame body (also referred to herein as a "body"), a valve disposed in the body, a leaflet clip coupled to the body, and a control element operably coupled to the leaflet clip. The body has a proximal end and a distal end. The leaflet clip is configured to be transitioned between a first configuration in which the prosthetic valve can be inserted into a heart, and a second configuration in which the leaflet clip is disposed to capture a native valve leaflet between the leaflet clip and the wire frame body when the body is disposed in a native annulus of an atrioventricular valve of a heart. The control element has a length sufficient to extend from the leaflet clip through a ventricle of the heart and out a wall of the ventricle when the body is disposed in the native annulus of the atrioventricular valve of the heart. The control element is configured to allow a user to transition the leaflet clip from its first configuration to its second configuration when the body is disposed in the native annulus of the atrioventricular valve of the heart.

In some embodiments, a method includes delivering to a native annulus of an atrioventricular valve of a heart a prosthetic valve having a self-expanding body having a proximal end and a distal end. A valve is disposed in the body and a leaflet clip is coupled to the body. The leaflet clip is movable between a first configuration and a second configuration, and a control element is operably coupled to the leaflet clip. The leaflet clip and the control element are disposed on a ventricular side of the native annulus. The leaflet clip is disposed in the first configuration, and the body is allowed to self-expand into engagement with the native annulus. A portion of the control element is disposed outside the heart, and with the control element, tension is released to allow the leaflet clip to transition between the first configuration and the second configuration to capture a native valve leaflet between the leaflet clip and the body.

In some embodiments, a system includes a prosthetic heart valve body, a leaflet clip, a control element operably coupled to the leaflet clip, and an elongate member. The body has a proximal end and a distal end. The leaflet clip is configured to be transition between a first configuration during deployment of the body, and a second configuration, in which the leaflet clip captures a native valve leaflet between the leaflet clip and the body when the body is disposed in a native annulus of an atrioventricular valve of a heart. The control element has a length sufficient to extend from the leaflet clip through the ventricle of the heart and out a wall of the ventricle when the body is disposed in the native annulus of the atrioventricular valve of the heart. The control element is configured to allow a user to transition the leaflet clip from its first configuration to its second configuration when the body is disposed in the native annulus of the atrioventricular valve of the heart. The elongate member has a first end and a second end. The first end is configured to be disposed in the ventricle of the heart during deployment of the body and the second end is configured to extend outside the heart. The elongate member defines a control element lumen. The control element is disposable in the control element lumen and extendable out the second end of the elongate member.

In some embodiments, a system for delivering a prosthetic heart valve to a native valve annulus includes a self-expanding wire frame body, a leaflet clip, an elongate member, and a control element. The body has a proximal end and a distal end. The elongate member has a first end and a second end. The first end of the elongate member is configured to be disposed in a ventricle of a heart during deployment of the prosthetic heart valve, and the second end of the elongate member is configured to extend outside the heart. The elongate member defines a control element lumen. The control element has a first end and a second end disposed in the control element lumen and operably coupled to the leaflet clip. The control element has a length sufficient to extend from the leaflet clip through the control element lumen and out a wall of the ventricle when the body is disposed in the native annulus of the atrioventricular valve of the heart. The control element is configured to allow a user to maintain the leaflet clip in a first configuration during deployment of the body, and to allow the user to transition the leaflet clip to a second configuration, in which the leaflet clip captures a native valve leaflet between the leaflet clip and the body when the body is disposed in the native annulus of the atrioventricular valve of the heart.

As used herein, the singular forms "a," "an", and "the" include plural referents unless the context clearly dictates otherwise. Thus, for example, the term "a member" is intended to mean a single member or a combination of members, "a material" is intended to mean one or more materials, or a combination thereof.

As used herein, the words "distal" and "proximal" refer to a direction close to and away from, respectively, an operator of, for example, a medical device. Thus, for example, the end of the medical device closest to the patient's body (e.g., contacting the patient's body or disposed within the patient's body) would be the proximal end of the medical device, while the end opposite the proximal end and closest to, for example, the user (or hand of the user) of the medical device, would be the distal end of the medical device.

As used herein, the terms "about" and "approximately" generally mean plus or minus 10% of the value stated. For example, about 0.5 would include 0.45 and 0.55, about 10 would include 9 to 11, about 1000 would include 900 to 1100.

As described herein, when a prosthetic heart valve is implanted and secured to a native heart valve annulus, native valve leaflets can become disposed between the prosthetic heart valve and the myocardium of the heart. When the native valve leaflets are disposed in such a manner, the native valve leaflets can, for example, interfere with operation of the prosthetic heart valve and/or with blood flow through the heart. For example, the native leaflets can obstruct the left ventricular outflow tract (LVOT), thereby reducing the flow of oxygenated blood to the body. The native leaflets can also obstruct the prosthetic heart valve and reduce the effective orifice area (EOA), thereby reducing the flow of blood from the atrium to the ventricle. Furthermore, the native valve leaflets can interfere with proper seating of the prosthetic heart valve in the native valve annulus resulting in improper operation of the prosthetic heart valve. Said another way, if the prosthetic heart valve body does not form a sufficient seal with the native valve annulus, blood can leak around the valve body and the prosthetic heart valve may not function properly.

In some embodiments, a prosthetic heart valve can include a leaflet clip. In use, i.e., during an operation in which the prosthetic heart valve is delivered to a native annulus of an atrioventricular valve of a heart (e.g., mitral valve or a tricuspid valve), the leaflet clip can function to capture (e.g., grab, couple to, connect with, bias, pierce, enclose, etc.) a native valve leaflet. For example, when the prosthetic heart valve is implanted into the native annulus of the heart, the leaflet clip can capture the native valve leaflet such that the native leaflet is disposed between the leaflet clip and a body portion of the prosthetic valve. In this manner, the native leaflet can be selectively positioned, for example, outside of the flow path between the prosthetic heart valve orifice, thereby preserving the EOA of the prosthetic heart valve, limiting and/or reducing LVOT obstruction, blood flow turbulence, eddies, or similar interference by the native leaflet during operation of the prosthetic heart valve. Similarly, over time as the native leaflet stiffens, due to calcification for example, or otherwise changes form, the leaflet clip can retain the native leaflet in a desirable position such that a desirable blood flow profile is maintained. Further, the native leaflet can be selectively positioned and/or enclosed by the leaflet clip to provide sealing between the prosthetic heart valve (e.g., the body of the prosthetic heart valve) and the native annulus of the heart valve, and additionally as a result, between the left ventricle of the heart and the left atrium of the heart.

As described in further detail herein, in some embodiments, the prosthetic heart valve and/or the leaflet clip can be operably coupled to a control element that is configured to allow a user to transition the leaflet clip to capture the native leaflet between the a body portion of the prosthetic heart valve and the leaflet clip.

FIG. 1 is a schematic illustration of a prosthetic heart valve system 1000. The prosthetic heart valve 1000 is designed to be disposed in a damaged or diseased native heart valve such as a mitral valve. The prosthetic heart valve 1000 (also referred to herein as a "prosthetic valve") includes a prosthetic valve body 1100, a first leaflet clip 1200a, and optionally a second leaflet clip 1200b (referred to collectively as "clips 1200"). In some embodiments, additional leaflet clips 1200 can be included in the prosthetic heart valve 1000. The leaflet clips 1200 are coupled to the prosthetic valve body 1100 and are configured to be transitioned between a first configuration in which the prosthetic valve 1000 can be inserted into a heart, and a second configuration in which the leaflet clips 1200 are disposed to capture one or more native valve leaflets between the leaflet clips 1200 and the valve body 1100 when the valve body 1100 is disposed in a native annulus of an atrioventricular valve of a heart. A control element 1300 is operably coupled to the leaflet clips 1200 and has a length sufficient to extend from the leaflet clips 1200 through a ventricle of the heart and out a wall of the ventricle when the valve body 1100 is disposed in the native annulus of the atrioventricular valve of the heart. The control element 1300 is further configured to allow a user to transition the leaflet clips 1200 from their first configuration to their second configuration (either individually or simultaneously) when the valve body 1100 is disposed in the native annulus of the atrioventricular valve of the heart.

The prosthetic valve body 1100 can be formed such that it can be deformed (e.g., compressed and/or expanded) and, when released, return to its original (undeformed) size and shape. To achieve this, the valve body 1100 can be formed of any suitable material, or combination of materials, such as metals or plastics that have shape memory properties. In some embodiments, the valve body 1100 can be formed from Nitinol. Other shape memory alloys, such as, for example, Cu—Zn—Al alloys and/or Cu—Al—Ni alloys can be used. The prosthetic valve body 1100 can be the same as or similar to any of the prosthetic valves described in International Patent Application No. PCT/US14/44047, entitled "Thrombus Management and Structural Compliance Features for Prosthetic Heart Valves," ("the '047 application"), and International Patent Application No. PCT/US14/40188, entitled "Structure Members for Prosthetic Mitral Valves," ("the 188 application"), the disclosures of which are incorporated herein by reference in their entirety.

The valve body 1100 includes a valve (not shown) disposed therein. The valve body 1100 can be any suitable size, shape, or configuration. In some embodiments, the valve body 1100 can include an outer frame, and an inner valve assembly that includes an inner frame and leaflets. Further, in some embodiments, the valve body 1100 can have an upper, proximal end (e.g., at an atrium portion), a lower, distal end (e.g., at a ventricle portion), and a medial portion (e.g., at an annulus portion) therebetween. The medial portion, in such embodiments, can have a perimeter that is configured to fit into an annulus of a native atrioventricular valve (e.g., a mitral valve or a tricuspid valve). The upper end of the outer frame can have a perimeter that is larger than the perimeter of the medial portion. As will be shown in further embodiments, portions of the valve body 1100 can have a D-shaped cross-section (e.g., the upper end and the medial portion of the outer frame). In this manner, the outer frame can promote a suitable fit into the annulus of the native atrioventricular valve.

As described herein, the leaflet clips 1200 are operably coupled to the valve body 1100. The leaflet clips 1200 can be coupled to the valve body 1100 in any suitable manner. In some embodiments, the leaflet clips 1200 and the valve body 1100 can be monolithically constructed. In other embodiments, the leaflet clips 1200 and the valve body 1100 can be formed separately and then joined together (e.g., using a wire, a screw, an interference fit, a weld, or otherwise any suitable fastener or fastening method). In some embodiments, the leaflet clips 1200 can be substantially permanently coupled to the valve body 1100, while in other embodiments, the leaflet clips 1200 can be removably coupled to the valve body 1100.

In some embodiments, the leaflet clips 1200 can be coupled to or a part of an outer frame of the valve body 1100, while in other embodiments, the leaflet clips 1200 can be coupled to or a part of an inner frame of the valve body 1100. Moreover, the leaflet clips 1200 can be coupled to the valve body 1100 at any suitable time. For example, the leaflet clips 1200 can be coupled to the valve body 1100 before delivery of prosthetic heart valve 1000 into a heart, i.e., the leaflet clips 1200 can be coupled to the valve body 1100 when the heart valve 1000 is disposed outside the heart. As another example, the leaflet clips 1200 can be coupled to the valve body 1100 after the prosthetic heart valve 1000 is disposed inside the heart. In this manner, the valve body 1100 and the leaflet clips 1200 can be delivered to the heart separately, and coupled to one another after both the valve body 1000 and the leaflet clips 1200 are disposed in the heart.

In some embodiments, the first leaflet clip 1200a can include a first leaflet covering 1210a disposed on at least a portion of the first leaflet clip 1200a. Similarly, in some embodiments, the second leaflet clip 1200b can include a second leaflet covering 1210b disposed on at least a portion of the second leaflet clip 1200b. The covering 1210a and the covering 1210b (referred to collectively as "coverings 1210") can be constructed from any suitable material, or any combination of materials such as, for example, stabilized tissue derived from 30 day old bovine, ovine, equine or porcine pericardium, or from animal small intestine submucosa. In some embodiments, the coverings 1210 can be constructed from a synthetic material including, for example, polyester, polyurethane, polytetrafluoroethylene, or a combination thereof. In use, the coverings 1210 can enhance the ability to capture, secure, bias, or otherwise contain or manipulate a native valve leaflet. For example, in use, the coverings 1210 can provide an enhanced surface area configured to at least partially enclose a native leaflet, thereby enhancing management and/or selective control of the native leaflet. In this manner, the coverings 1210 can prevent at least a portion of one or more native leaflets from protruding through an area defined by the leaflet clips 1200, thereby limiting and/or reducing the potential undesirable interference of the one or more native valve leaflets with blood flow, LVOT, EOA, or otherwise proper functioning of the heart and/or the prosthetic heart valve 1000. Moreover, in some embodiments the coverings 1210 can be configured to promote or accelerate desirable in-growth between the coverings 1210 and/or the valve body 1100, and the native leaflets.

In some embodiments, the coverings 1210 can substantially cover the leaflet clips 1200 (e.g., substantially the entire area defined by the leaflet clips 1200). In other embodiments, the coverings 1210 can define an aperture, or multiple apertures, to allow blood to flow there-through (e.g., from the atrium to the ventricle during delivery of the prosthetic valve 1000, during deployment of the valve body 1100, and/or during manipulation of the leaflet clips 1200). In this manner, in use, an aperture of the coverings 1210 can be configured to limit and/or reduce blood flow restriction, and enhance movement and manipulation of the leaflet clips 1200 and/or the valve body 1100. Further to this example, in use, the coverings 1210 can be configured to allow blood flow there-through when the leaflet clips 1200 are in a disengaged (i.e., disengaged with respect to a native leaflet; in a "ready state"). Such a configuration can limit and/or prevent undesirable interruption of blood flow (e.g., LVOT obstruction) during delivery and deployment of the prosthetic heart valve 1000 and the leaflet clips 1200. The aperture(s) can be sized and/or shaped in any suitable manner, e.g., to encourage a desirable flow rate therethrough. As described herein, in some embodiments, the coverings 1210 can include multiple materials and/or configurations. In this manner, the coverings 1210 can be configured to promote in-growth between the coverings 1210 and/or the valve body 1100, and the native leaflets. For example, the coverings 1210 can include varying porosities configured to promote in-growth and/or allow blood to flow through the varying porosities at varying flow rates.

The leaflet clips 1200 can be any shape, size or configuration, and can be formed of any suitable material, or combination of materials. In some embodiments, similar to the valve body 1100 in some instances, the leaflet clips 1200 can be formed such that they can be deformed (e.g., compressed, expanded, reconfigured, or otherwise biased in some manner), and when released, return to their original sizes, shapes and/or configurations (undeformed).

In some embodiments, the leaflet clips 1200 can be substantially identical to each other in shape, size, and/or configuration, while in other embodiments, the leaflet clips 1200 can be different than one another in shape, size, and/or configuration. Various configurations of the leaflet clips 1200 will be discussed in further detail herein, and illustrated in more detail in further figures.

The leaflet clips 1200 can function to engage (e.g., capture, bias, couple to, connect with, pierce, enclose, etc.) one or more native leaflets of a heart valve. More specifically, the leaflet clips 1200 can capture a native leaflet between the leaflet clips 1200 and the valve body 1100. Any number of leaflet clips can be configured to capture any number of native valve leaflets, and at any location of the valve body 1100, as discussed in further detail herein. In some embodiments, the leaflet clips 1200 (i.e., the leaflet clip 1200*a* and the leaflet clip 1200*b*) can be configured to capture a single native valve leaflet. In other embodiments, the leaflet clips 1200 can be configured to capture multiple native leaflets. For example, the leaflet clip 1200*a* can be configured to capture a native leaflet at an A2 portion (also referred to as "A2 leaflet") of the heart valve, and the leaflet clip 1200*b* can be configured to capture a native leaflet at a P2 portion (also referred to as "P2 leaflet") of the heart valve. Further to this example, in many instances the A2 leaflet has a size and shape different than the P2 leaflet. In such instances, the first leaflet clip 1200*a* can be sized and/or shaped to sufficiently engage and capture the A2 leaflet. Similarly, the second leaflet clip 1200*b* can be sized and/or shaped to sufficiently engaged and capture the P2 leaflet. In some embodiments, the leaflet clips 1200 can vary in width based on their configuration or position. For example, the leaflet clips 1200 can have a first width when disposed in a disengaged position, and a second width when disposed in an engaged configuration, where the second width is greater than the first width.

Moreover, in this manner, one or more native leaflets can be captured and selectively positioned outside of the flow path defined between the prosthetic heart valve 1000 orifice (e.g., through the valve disposed in the valve body 1100), thereby preventing obstruction or reduction of the EOA. Similarly, the leaflet clips 1200 and the valve body 1100 can collectively function to position one or more native leaflets to provide sealing between the prosthetic heart valve 1000 (e.g., an outer portion of the valve body 1100) and the native annulus of the atrioventricular valve of the heart.

In some embodiments, a force can be applied to the leaflet clips 1200. In this manner, the leaflet clips 1200 can be disposed in a first configuration based at least in part on the force. Further, in such embodiments, the leaflet clips 1200 can be transitioned into a second configuration based at least in part on reduction of the force. Similarly stated, the leaflet clips 1200 can be disposed in a first configuration for a time period and when the force (e.g., tension) is being applied to the leaflet clips 1200. In such embodiments, the leaflet clips 1200*s* can be transitioned from the first configuration to a second configuration after the time period and when the force is reduced or no longer applied (e.g., the tension is released). Further, in some embodiments, the leaflet clips 1200 can transition from the first configuration to the second configuration based on a force (e.g., generated by a user), as previously discussed above, and alternatively or additionally, the leaflet clips 1200 can transition from the first configuration to the second configuration based on a material from which the leaflet clips 1200 are formed (e.g., a material having shape memory properties).

The leaflet clips 1200 can be operably coupled to the control element 1300 (e.g., suture, tether, etc.) in any suitable manner. The control element 1300 can be configured to allow a user to transition the leaflet clips 1200 from a first configuration (e.g., during delivery, disengaged from native leaflet) to a second configuration (e.g., engaged with the native leaflet). For example, in some embodiments, the control element 1300 can apply a force to the leaflet clips 1200 such that the leaflet clips 1200 are disposed in the first configuration. Further to this example, in some embodiments, the first configuration can include the leaflet clips 1200 being disposed in a deformed state, e.g., in instances where the leaflet clips 1200 are formed of shape memory material. In such embodiments, the control element 1300 can reduce or remove the force to the leaflet clips 1200 such that the leaflet clips 1200 transition from the first configuration to the second configuration. The second configuration can include the leaflet clips 1200 being disposed in an undeformed state, e.g., in instances where the leaflet clips 1200 are formed of shape memory material. In other embodiments, the force applied by the control element 1300 can be a first force, and the leaflet clips 1200 can transition from the first configuration to the second configuration based at least in part on a second force (e.g., a spring, hinge or the like coupled to the valve body 1100 and operably coupled to the leaflet clips 1200). For example, the prosthetic valve 1000 can include leaflet clip attachment members (not shown) disposed between the leaflet clips 1200 and the valve body 1100. The leaflet clip attachment members can transition the leaflet clips 1200 from the first configuration to the second configuration. For example, the leaflet clip attachment members can include an energy storage member such as a spring-loaded hinge, a spring, or the like. Further to this example, instead of or in addition to shape memory properties of the leaflet clips 1200 causing the leaflet clips 1200 to transition from the first configuration to the second configuration, the energy storage member can promote transition of the leaflet clips 1200 from the first configuration to the second configuration.

In some embodiments, the leaflet clips 1200 can be removably coupled to the control element 1300. In use, the control element 1300 can be coupled to the leaflet clips 1200 during delivery of the prosthetic valve 1000 to a native annulus of an atrioventricular valve of a heart, and during manipulation of the leaflet clips 1200, and selectively decoupled (e.g., by an operator) from the leaflet clips 1200 thereafter.

Although control element 1300 is shown in FIG. 1 as being operably coupled to both leaflet clip 1200*a* and leaflet clip 1200*b*, in some embodiments, control element 1300 can include a first control element 1300*a* and a second control element 1300*b*. In such embodiments, the first control element 1300*a* and the second control element 1300*b* can be monolithically constructed, while in other embodiments, the first control element 1300*a* and the second control element 1300*b* can be formed separately, and in some cases, attached. In some embodiments, the first control element 1300*a* can be operably coupled to the first leaflet clip 1200*a* and not the second leaflet clip 1200*b*, and the second control element 1300*b* can be operably coupled to the second leaflet clip 1200*b* and not the first leaflet clip 1200*a*. In other embodiments, the first control element 1300*a* and the second control element 1300*b* can each be operably coupled to both the first leaflet clip 1200*a* and the second leaflet clip 1200*b*.

The first control element 1300*a* and the second control element 1300*b* can be coupled to one another in any suitable manner (e.g., a knot, a fastener, etc.) such that a user can operate both the first control element 1300*a* and the second control element 1300*b* substantially simultaneously, and as such, the user can manipulate both the first leaflet clip 1200*a* and the second leaflet clip 1200*b* substantially simultaneously. In use, in some embodiments, the first control element 1300*a* can be coupled to the second control element 1300*b* within the heart, while in other embodiments, the first control element 1300*a* can be coupled to the second control element 1300*b* outside the heart.

In some embodiments, the first control element 1300*a* and the second control element 1300*b* can be configured such that a user can independently operate the first control element 1300*a* and the second control element 1300*b*, and as such, the user can independently manipulate the first leaflet clip 1200*a* and the second leaflet clip 1200*b*. In this manner, a user can transition first leaflet clip 1200*a* via the first control element 1300*a* from a disengaged configuration (e.g., in which the prosthetic valve can be inserted into the heart) to an engaged configuration (e.g., in which the first leaflet clip 1200a is disposed to capture a native valve leaflet between the first leaflet clip 1200a and the valve body 1100). In a similar manner, a user can transition the second leaflet clip 1200b via the second control element 1300b from a disengaged configuration (e.g., in which the prosthetic valve can be inserted into the heart) to an engaged configuration (e.g., in which the second leaflet clip 1200b is disposed to capture a native valve leaflet between the second leaflet clip 1200b and the valve body 1100).

Moreover, the first leaflet clip 1200a and the second leaflet clip 1200b can include a first control portion (not shown) and a second control portion (not shown), respectively (referred to collectively as "control portions"). The control portions 1230 can be configured to be coupled to the control element 1300. In some embodiments, the control portions 1230 can include an aperture, a ring, a loop, a slot, or otherwise any suitable anchor point for the control element 1200 to attach to. In some embodiments, the control portions 1230 and the leaflet clips 1200 can be monolithically constructed, while in other embodiments, the control portions 1230 and the leaflet clips 1200 can be formed separately and then joined together (e.g., using a wire, a weld, or otherwise any suitable fastener or fastening method).

In some embodiments, the leaflet clips 1200 can be configured to not undesirably interfere with a portion of an atrioventricular valve of a heart. For example, the leaflet clips 1200 can be sized and shaped such that they do not undesirably interfere with a native annulus of the atrioventricular valve (e.g., when the leaflet clips 1200 are in an engaged configuration or in the process of transitioning into the engaged configuration). Further to this example, more specifically, the leaflet clips 1200 can have a first end and a second end having a length that is less than a length of the valve body 1100. As such, the leaflet clips 1200 can be spaced a non-zero distance from the native annulus when the leaflet clips 1200 are in the engaged configuration. In this manner, the leaflet clips 1200 can transition between various positions and configurations without undesirably interfering with the native annulus, while having a length sufficient to capture one or more native leaflets. Similarly, the leaflet clips 1200 can be spaced a non-zero distance from an internal surface of a ventricle (e.g., a ventricular wall) when the leaflet clips 1200 are in the disengaged configuration, engaged configuration, or any position there between. In this manner, the leaflet clips 1200 can transition between various positions and configurations without undesirably interfering with portions of the atrioventricular valve, such as, a ventricular wall.

Figure 2B:
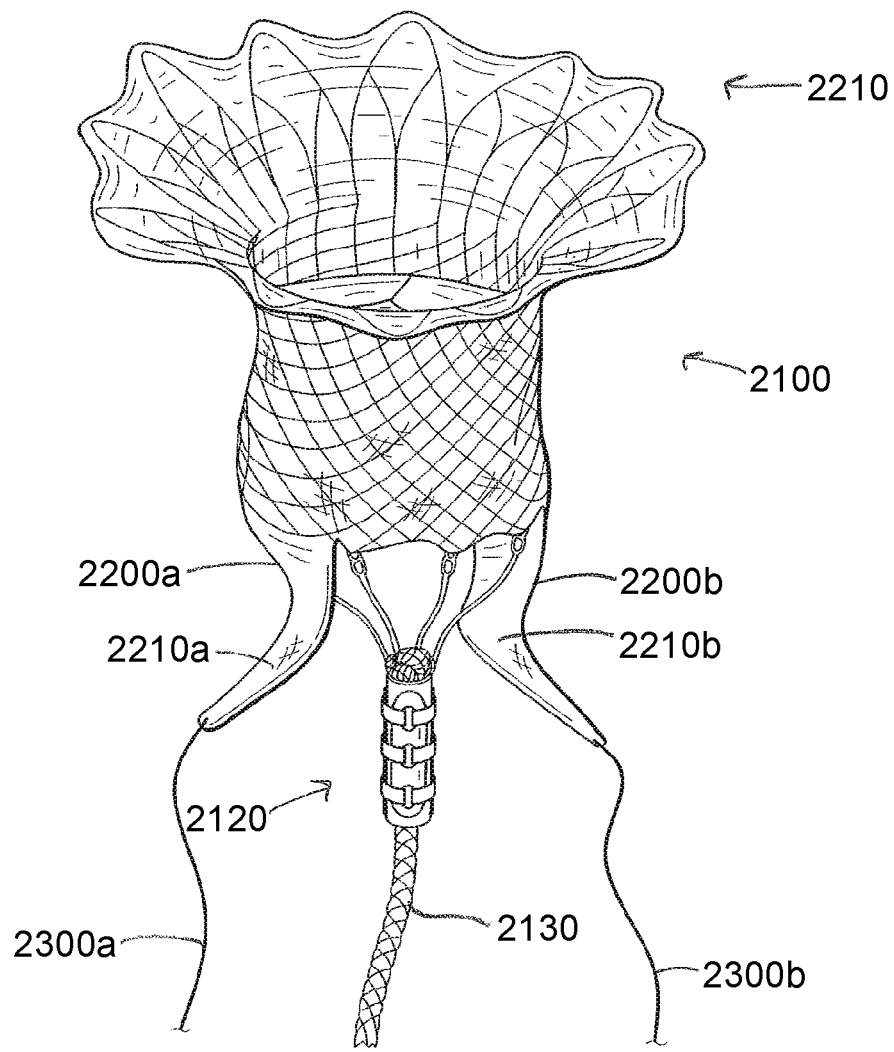

FIGS. 2a-2c show a prosthetic valve 2000 according to an embodiment in a first position (FIG. 2a), a second position (FIG. 2b), and a third position (FIG. 2c), respectively. The prosthetic valve 2000 includes a valve body 2100, a first leaflet clip 2200a and a second leaflet clip 2200b (referred to collectively as "leaflet clips 2200"), an anchoring tether 2130, and a first control element 2300a and a second control element 2300b (referred to collectively as "control elements 2300"). The valve body 2100 has a proximal end 2110 and a distal end 2120, and includes multiple self-expanding atrial anchoring elements distributed circumferentially about, and extending radially outwardly from, the proximal end 2110 of the valve body 2100. In this embodiment, the valve body 2100 and the leaflet clips 2200 are formed from a laser-cut tube of Nitinol. The anchoring tether 2130 is coupled to the distal end 2120 of the valve body 2100.

The leaflet clips 2200 are integrally formed with the valve body 2100. The first leaflet clip 2200a and the second leaflet clip 2200b include a first leaflet clip covering 2210a and a second leaflet clip covering 2210b, respectively (referred to collectively as "coverings 2210"). As described above, the coverings 2210 can be constructed from any suitable material, or any combination of materials.

The anchoring tether 2130 is attached to the distal end 2120 of the valve body 2100. Although not shown, the anchoring tether 2130 can have a length sufficient to extend from the distal end 2120 of the valve body 2100 through the ventricle of a heart and out the wall of the ventricle when the valve body 2100 is disposed in a native annulus of an atrioventricular valve of the heart. The anchoring tether 2130 can be configured to anchor the prosthetic valve 2000 to the heart at a location external to the heart.

As best shown in FIG. 2b, the control elements 2300 are operably and removably coupled to the leaflet clips 2200. In this manner, the control elements 2300 are configured to transfer a force to the leaflet clips 2200 such that the leaflet clips 2200 transition among various positions. Further, the control elements 2300 are configured to allow a user to transition leaflet clips 2200 among the various positions.

In use, the leaflet clips 2200 can be transitioned between several different positions. For ease of illustration, in FIGS. 2a-2c, first leaflet clip 2200a and the second leaflet clip 2200b are shown in like or matching positions. It should be noted that, in some embodiments, the first leaflet clip 2200a and the second leaflet clip 2200b can be transitioned at different times between different positions. For example, the first leaflet clip 2200a can be disposed in a first position when second leaflet clip 2200b is disposed in a second position. In this manner, a user can manipulate each leaflet clip independently such that the first leaflet clip 2200a can capture a native leaflet at a first time, and the second leaflet clip 2200b can capture a native leaflet at a second time after the first time. Such functionality allows for better, more repeatable capture and recapture of native leaflets.

In the first position (FIG. 2a), the leaflet clips 2200 are in disengaged positions (i.e., disengaged with respect to a native valve leaflet). Said another way, in the first position, the leaflet clips 2200 are in a "ready state" (i.e., ready to capture a native valve leaflet between the leaflet clips 2200 and the valve body 2100). Further, in the first position, the leaflet clips 2200 are disposed such that the valve body 2100 can be inserted into a heart. In this manner, in use, as the valve body 2100 is delivered to a native annulus of an atrioventricular valve of a heart, the leaflet clips 2200 can limit and/or provide for minimal undesirable contact and/or interference with portions of the heart (e.g., native chordae tendineae of the heart). Further, in the first position, the leaflet clips 2200 are in their deformed positions, i.e., not in their at least partially predefined, undeformed positions, e.g., as defined in part by their shape memory properties. Moreover, as shown, a force (tension) is applied by the control elements 2300 to the leaflet clips 2200. In this manner, the control elements 2300 are configured to maintain the leaflet clips 2200 in the first position.

To move the leaflet clips 2200 from the first position (FIG. 2a) to the second position (FIG. 3), tension applied to the leaflet clips 2200 by the control elements 2300 is partially released. As shown in FIG. 2b, in the second position, the leaflet clips 2200 are in intermediate states. Similarly stated, the leaflet clips 2200 are in partially engaged positions, i.e., in a position to contact a native valve leaflet of the heart.

To move the leaflet clips 2200 from the second position (FIG. 2b) to the third position (FIG. 2c), tension applied to the leaflet clips 2200 by the control elements 2300 is released further. In the third position (FIG. 2c), the leaflet clips 2200 are in fully engaged positions. In this manner, the leaflet clips 2200 are disposed to capture one or more native valve leaflets (not shown) between the leaflet clips 2200 and the valve body 2100 when the valve body 2100 is disposed in a native annulus of an atrioventricular valve of a heart (not shown). Thus, the leaflet clips 2200 are configured to retain one or more native valve leaflets when the leaflet clips 2200 are in the third position such that one or more native valve leaflets do not undesirably interfere with flow through the valve body 2100 (e.g., through a prosthetic valve disposed in the valve body 2100).

Although the leaflet clips 2200 are shown as rotating and/or bending about an axis when transitioning between positions (FIGS. 2a-2c), in other embodiments, the leaflet clips 2200 can be configured to transition between positions in any suitable manner to capture and/or bias one or more native valve leaflets. For example, the leaflet clips 2200 can be configured to slide and/or otherwise translate between positions (e.g., from the first position to the third position) to capture one or more native valve leaflets.

Although the transition of the leaflet clips 2200 from the first position (disengaged; deformed) to the second position (intermediate; partially engaged and deformed) and to the third position (engaged, undeformed) has been described above as resulting at least in part from a release or reduction of tension via the control elements 2300, in other embodiments, leaflet clips 2200 can be transitioned between positions in or by any suitable manner. For example, the leaflet clips 2200 can be configured to transition from a disengaged, undeformed position, to an engaged position, at least in part in response to receiving a force from control elements 2300. In this manner, a force can be applied to the leaflet clips 2200 to cause the leaflet clips 2200 to transition from their disengaged position to their engaged position (i.e., disposed to capture one or more native valve leaflets between the leaflet clips 2200 and the valve body 2100 when the valve body 2100 is disposed in a native annulus of an atrioventricular valve of a heart).

In use, the force applied to and released from the leaflet clips 2200 can be produced and released in any suitable manner, e.g., the force can be produced and reduced manually by a user. For example, a user can apply or release tension at a distal end portion (not shown) of the control elements 2300. Further to this example, the distal end portion of the control elements 2300 can be disposed outside the heart.

As described herein, the leaflet clips 2200 are configured to capture native leaflets of a heart valve. In doing so, the leaflet clips 2200 can be moved throughout the ventricle of a native heart valve. In some embodiments, the leaflet clips 2200 can be configured to limit or avoid undesirable interference with portions of the heart valve (e.g., interference with the native chordae tendineae of the heart, or a wall of the heart), and to promote sufficient capture and/or containment of one or more native leaflets. For example, the leaflet clips 2200 can have one or more axis or points of rotation. In this manner, in use, as the leaflet clips 2200 are transitioned through various positions within the heart, the leaflet clips 2200 can be maintained in profiles suitable for avoidance of undesirable interference with portions of the native heart valve, and suitable for sufficient capture of one or more native leaflets.

Figure 3:
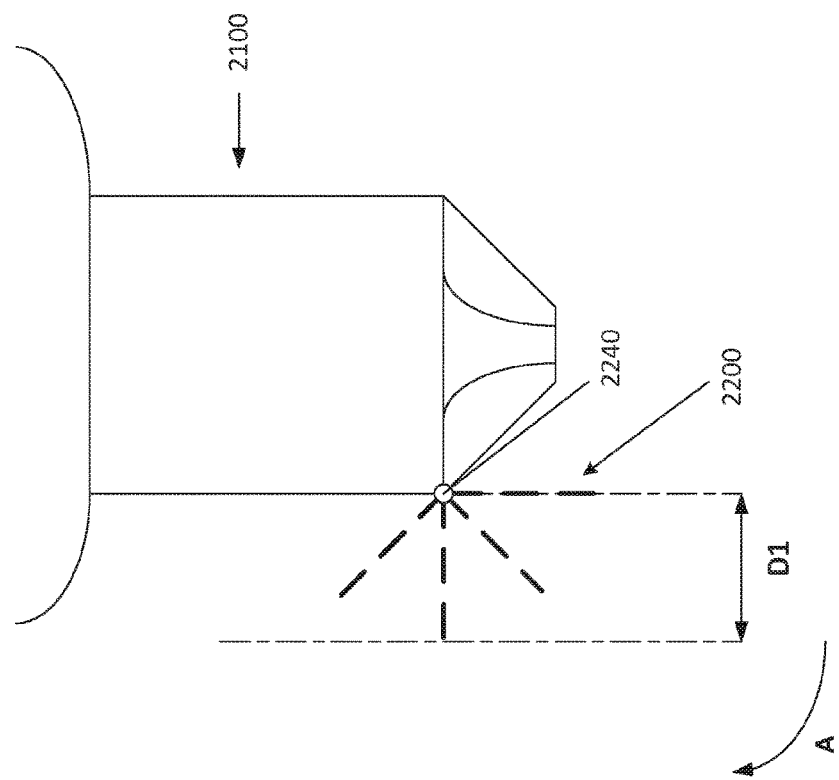
FIGS. 3 and 4 show prosthetic heart valve leaflet clips having a single point of rotation and two points of rotation, respectively, in various positions.
Figure 4:
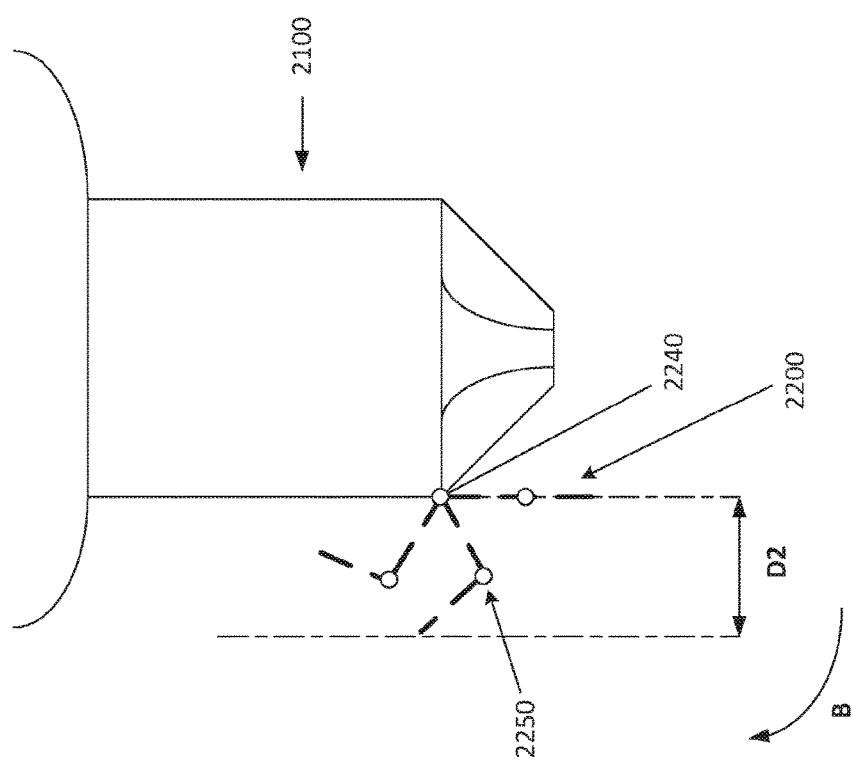

Further to this example, as shown in FIGS. 3 and 4, the leaflet clips 2200 can have a single point of rotation (FIG. 3) or two points of rotation (FIG. 4), respectively. As shown in FIG. 3, the leaflet clip 2200 can have a single point of rotation, i.e., rotation point 2240. In use, the leaflet clip 2200 can be transitioned between various positions and configurations, shown by arrow A, by being rotated about the rotation point 2240. Further, the leaflet clip 2200 can have distal end disposed at a maximum distance D1 measured from that distal end to an axis defined by an end of the valve body 2100 when the leaflet clip 2200 is being transitioned from a disengaged configuration to an engaged configuration. As another example, as shown in FIG. 4, the leaflet clip 2200 can have two points of rotation, i.e., a first point of rotation 2240 and a second point of rotation 2250. In use, the leaflet clip 2200 can be transitioned between various positions and configurations, shown by arrow B, by being rotated about the rotation point 2240 and the rotation point 2250. Further to this example, the leaflet clip 2200 can have a distal end disposed at a maximum distance D2 measured from that distal end to an axis defined by an end of the valve body 2100 when the leaflet clip 2200 is being transitioned from a disengaged configuration to an engaged configuration. As shown, distance D1 is greater than distance D2. Thus, the additional rotation point, i.e., rotation point 2250, can reduce or limit the leaflet clips 2200 profile, thereby promoting avoidance of undesirably interference with portions of the native heart valve. In addition, the additional rotation point can promote suitable capture of one or more native leaflets. Although the leaflet clip 2200 shown in FIG. 4 has only two rotation points, in some embodiments, the leaflet clip 2200 can have any suitable number rotation points (e.g., 3, 4, 5 or more).

Figure 5:
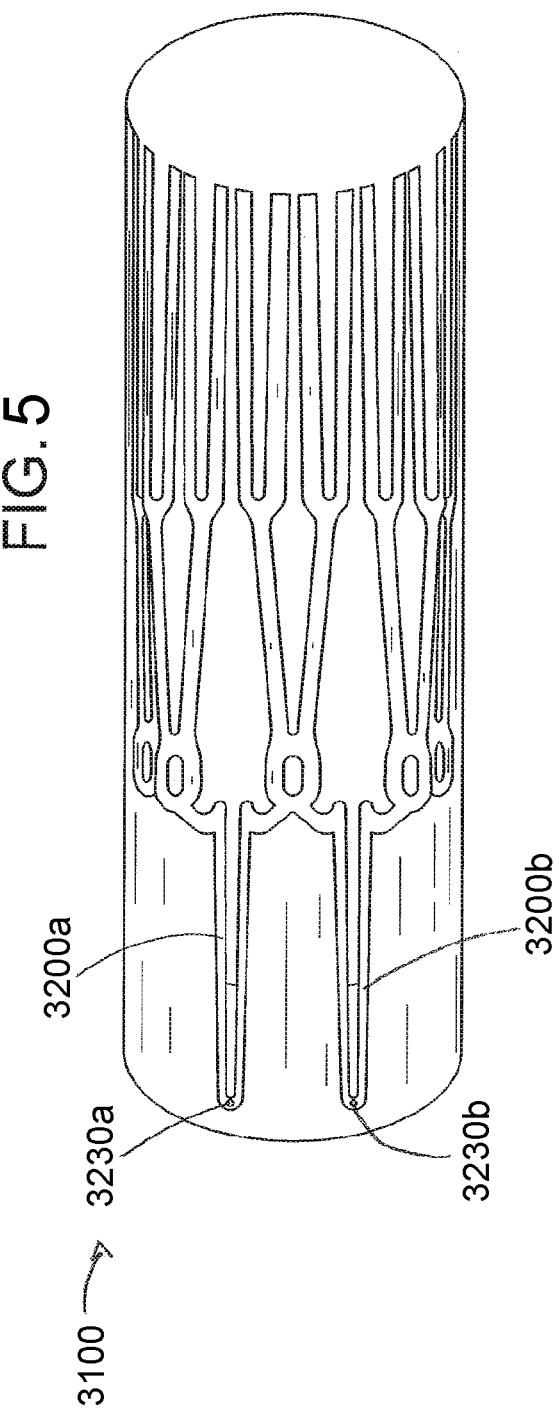
FIG. 5 shows a prosthetic heart valve body in a rolled configuration according to an embodiment.
Figure 6:
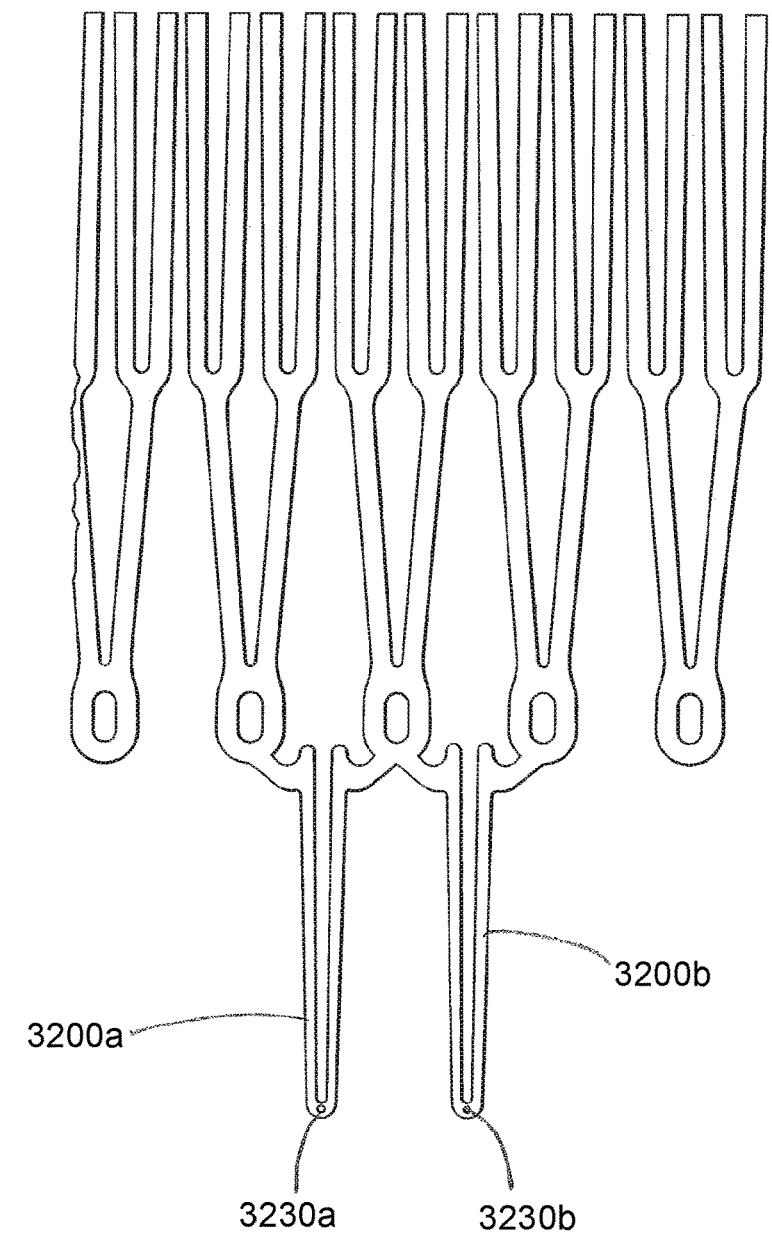
FIG. 6 shows the prosthetic heart valve body of FIG. 5 in a flattened configuration according to an embodiment.
Figure 7:
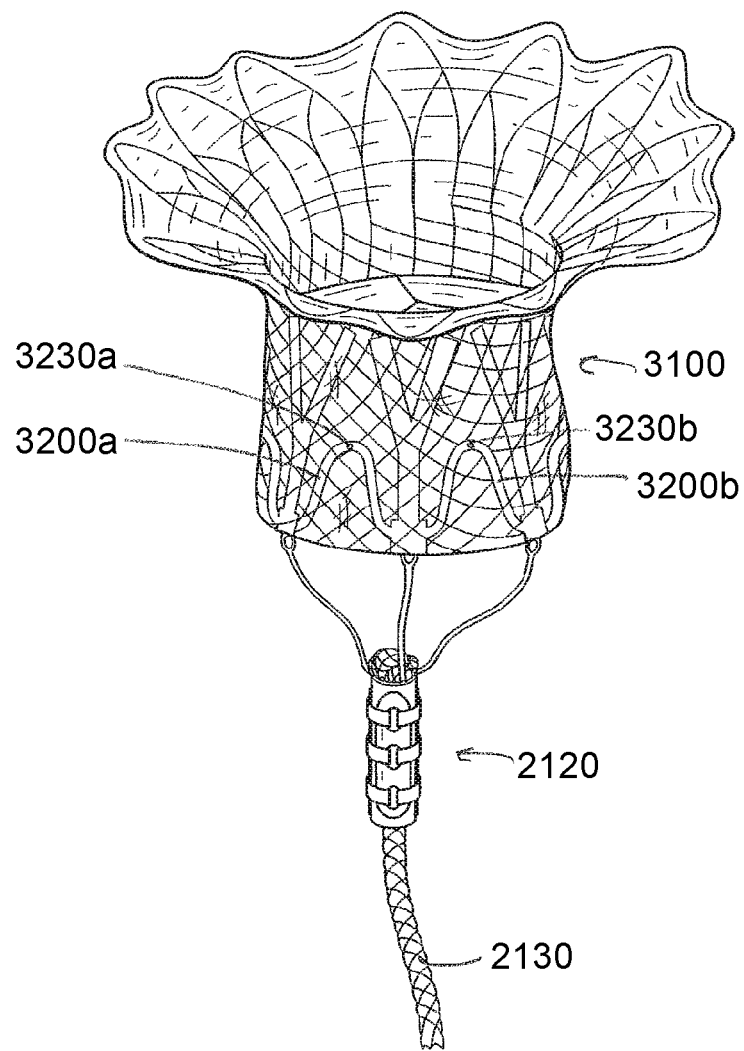
FIG. 7 shows a prosthetic heart valve system including the valve body of FIGS. 5 and 6, according to an embodiment.

FIGS. 5-7 show a valve body 3100 and leaflet clips 3200, of a prosthetic heart valve 3000, in an undeformed, initial state, i.e., as laser-cut, and in a rolled configuration (FIG. 5), a flat sheet of the same for ease of illustration (FIG. 6), and a side view with the leaflet clips 3200 in an engaged position (FIG. 7), according to an embodiment. As shown in FIG. 5, the leaflet clips 3200 and the valve body 3100 are formed and laser-cut from the same piece of Nitinol. As such, the leaflet clips 3200 are integral to the valve body 3100.

The prosthetic valve 3000 includes a first leaflet clip 3200a and a second leaflet clip 3200b (referred to collectively as "leaflet clips 3200"). The leaflet clips 3200 can be configured the same as or similar to the leaflet clips described in any other embodiments described herein (e.g., the leaflet clips 1200 and/or the leaflet clips 2200). The leaflet clips 3200 can be any suitable shape, size, or configuration to capture a native valve leaflet. The first leaflet clip 3200a and the second leaflet clip 3200b are configured to collectively capture a native valve leaflet (e.g., an A2 leaflet). The first leaflet clip 3200a includes a leaflet control portion 3230a configured to operably couple to a control element (not shown). Similarly, the second leaflet clip 3200b includes a leaflet control portion 3230b configured to operably couple to the control element (not shown). The leaflet control portion 3230a and the leaflet control portion 3230b are referred to collectively as "control portions 3230." The leaflet control portions 3230 each define an aperture. In some embodiments, the leaflet control portions 3230 can define any suitable number of apertures, and in any suitable size, shape or configuration.

Moreover, in some embodiments, control element (not shown) can include a tether configured to be routed through the apertures defined by the control portions 3230. In this manner, in use, the control element can cause the leaflet clips 3200 to transition between various positions (e.g., the same or similar positions discussed above with respect to prosthetic heart valve 2000).

Although the control portions 3230 each define an aperture, in other embodiments, the control portions 3230 can be any suitable shape, size, or configuration. For example, the control portions 3230 can include a protrusion, a fastener, a clasp, or the like, i.e., any suitable feature to allow for attachment of or control/manipulation by control element (e.g., a user of control element).

As best shown in FIG. 7, the first leaflet clip 3200a and second leaflet clip 3200b are each disposed on a single side portion of the valve body 3100, e.g., an A2 portion of the valve body 3100. In this manner, the first leaflet clip 3200a and second leaflet clip 3200b can be configured to capture a single native valve leaflet when prosthetic heart valve 3000 is disposed in a native atrioventricular valve of a heart. The leaflet clips 3200 can include coverings (not shown) the same as or similar to the coverings described above with respect to leaflet clips 1210 and/or leaflet clips 2210.

Although many of the leaflet clips discussed herein are integral to their respective valve bodies, in some embodiments, one or more leaflet clips can be formed separately from a valve body, and then joined together in any suitable manner (e.g., using any suitable fastener or fastening method, a screw, wire, an interference fit, laser welding, etc.). In addition, in some embodiments, one or more leaflet clips can include a pivot portion configured to provide an axis about which the clip can fold over and/or otherwise capture a native valve leaflet. Said another way, the pivot portion of the leaflet clip can delineate an axis across the leaflet clip such that a portion of the leaflet clip disposed on one side of the axis is configured to contact a proximal portion of the native leaflet, and a portion of the leaflet clip disposed on the opposite side of the axis is configured to contact a distal portion of the native leaflet. In some embodiments, a leaflet clip can include multiple points of rotation (e.g., two points of rotation).

Figure 8A:
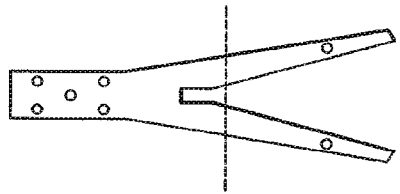
FIGS. 8a-10b show prosthetic heart valve leaflet clips in a first configuration (FIGS. 8a, 9a, 10a) and in a second configuration (FIGS. 8b, 9b, 10b) according to an embodiment.
Figure 8B:
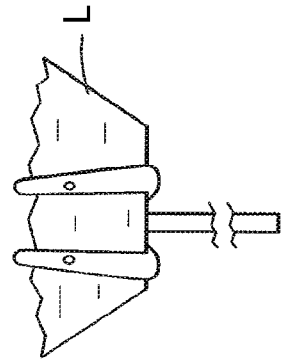
Figure 9B:
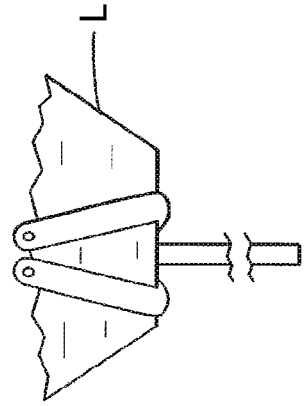
Figure 9A:
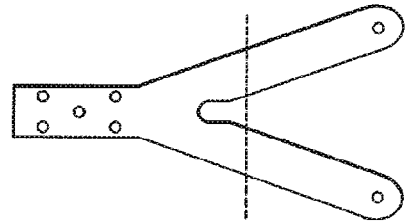
Figure 10A:
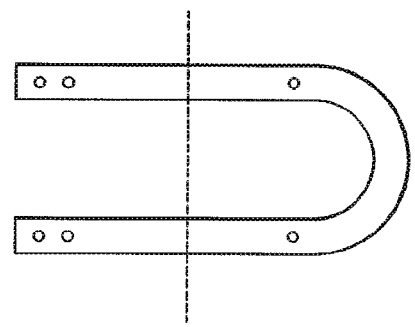

In some embodiments, the leaflet clips described herein can include a clip attachment portion configured to allow the leaflet clip to be coupled to a valve body. For example, as shown in FIGS. 8a-10b, a leaflet clip 4200 defines a clip attachment portion 4250, a pivot portion 4260, and a leaflet control portion 4230. The leaflet clip 4200 is configured to be coupled to the valve body 4100 at the clip attachment portion 4250. As shown in FIGS. 8a, 9a, and 10a, the leaflet attachment portion 4250 defines multiple apertures configured to allow for the leaflet clip 4200 to be coupled to the valve body 4100 in any suitable manner (e.g., any suitable fastener, a screw, a wire, a tether, laser weld, etc.). The number of apertures defined by the leaflet attachment portion 4250 in FIGS. 8a, 9a, and 10a are illustrative examples. In other embodiments, any suitable number of apertures can be defined and/or used.

Figure 10B:
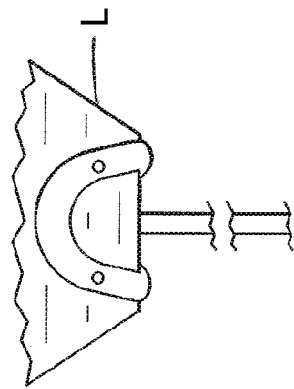

In use, the leaflet clip 4200 is configured to capture a native valve leaflet. FIGS. 8a, 9a, and 10a show leaflet clip 4200 in a first configuration ("ready state", disengaged). FIGS. 8b, 9b, and 10b show the leaflet clip 4200 in a second configuration (engaged), i.e., disposed to capture native leaflet L between either end of the leaflet clip 4200, the ends being defined in part by the pivot portion 4260.

Further shown in FIGS. 8a-10b are examples of various shapes, sizes, and configurations of the leaflet clip 4200. FIGS. 8a and 8b, for example, show the leaflet clip 4200 as having a fork-like shape, i.e., a shape having two prongs spaced apart in a suitable manner by a width configured to promote suitable capturing of a native valve leaflet. Similarly, FIGS. 9a and 9b, show the leaflet clip 4200 as having a similar two-prong structure, however, the prongs have a width larger than a width of the prongs illustrated in FIGS. 8a and 8b. As another example, FIGS. 10a and 10b show the leaflet clip 4200 as having a U-shape.

Figure 11:
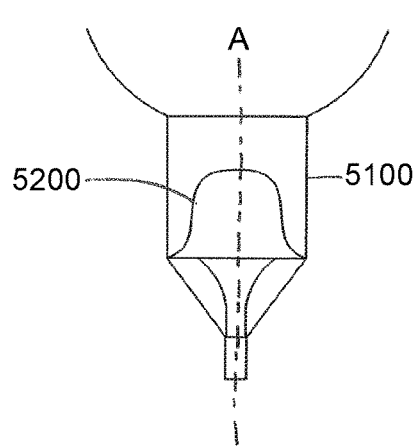
FIGS. 11-13 show various prosthetic heart valve leaflet clips according to an embodiment.
Figure 12:
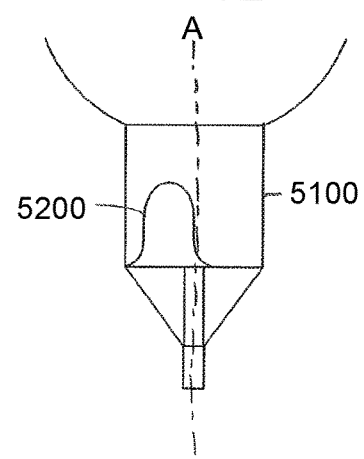

As described above, the leaflet clips can have any suitable configuration and can be disposed at any suitable location on the valve body. For example, as shown in FIG. 11, the leaflet clip 5200 can be symmetrical with respect to an axis, i.e., axis A, defined by the valve body 5100 of a prosthetic valve 5000. In some embodiments, as shown for example in FIG. 12, the leaflet clip 5200 can be offset, i.e., asymmetric with respect to axis A defined by the valve body 5100. In some embodiments, such as the asymmetric configuration shown in FIG. 12, the leaflet clip 5200 can promote desirable capturing of a native leaflet. Further to this example, in use, an asymmetric configuration, i.e., asymmetric with respect to axis A, can be configured to dispose the leaflet clip 5200 in a substantially symmetric fashion with respect to a centerline axis of a native leaflet (not shown) when the valve body 5100 is disposed in a native annulus of an atrioventricular valve of a heart. In this manner, the leaflet clip 5200 can be disposed at a radial position of the valve body 5100 based at least in part on a location of a target native valve leaflet so as to promote suitable capture and/or control of the native valve leaflet.

Figure 13:
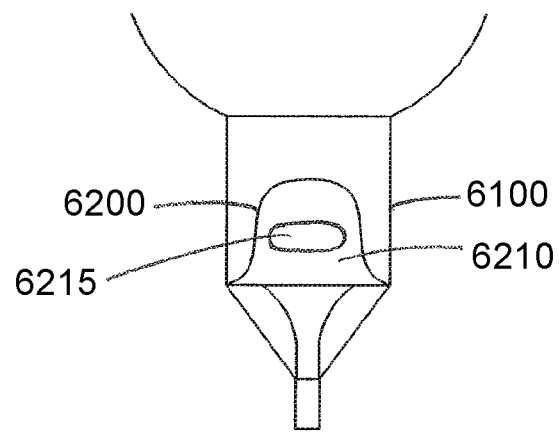

FIG. 13 shows a side view of a prosthetic heart valve 6000 having a valve body 6100 and a leaflet clip 6200 disposed in an engaged configuration, according to an embodiment. The leaflet clip 6200 includes a covering 6210 that defines a passageway 6215 configured to allow blood to flow therethough when the prosthetic heart valve 6000 is being delivered to a native heart valve. In this manner, the passageway 6215 can allow blood to flow there-through when the leaflet clip 6200 is disposed in a disengaged "ready state" position (not shown) during delivery, thereby limiting and/or reducing potential blood flow restriction, and enhancing movement and manipulation of the leaflet clip 6200 and the valve body 6100 during delivery thereof. Although the passageway 6215 of the leaflet clip 6200 is shown as oval-shaped aperture, in other embodiments, passageway 6215 can be any suitable shape, size, or configuration, and can include any suitable number of apertures, windows, passageways or varying porosities. For example, the passageway 6215 can define multiple distinct passageways (e.g., 2, 3, 4 or more). In other embodiments, the passageway 6215 can define multiple passageways operably coupled to one another (e.g., in fluid communication).

Figure 14:
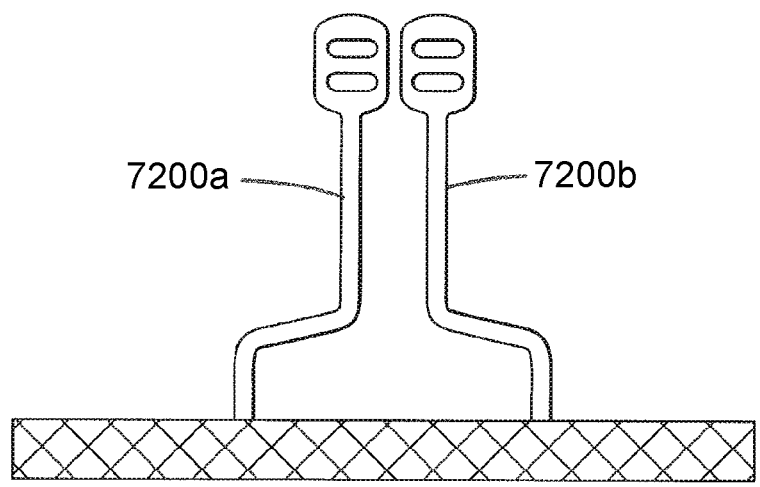
FIG. 14 shows a prosthetic heart valve leaflet clip in a flattened configuration according to an embodiment.

FIG. 14 shows a first leaflet clip 7200a and a second leaflet clip 7200b (referred to collectively as "clips 7200") having a curved shape, according to an embodiment. The curved shape of the leaflet clips 7200 can be configured to facilitate delivery and deployment of the valve body (not shown) and the leaflet clips 7200. More specifically, the leaflet clips 7200 can be configured to limit or avoid undesirable interference and/or contact between the leaflet clips 7200 and native chordae tendineae of a heart. Although shown as having an S-shape, in other embodiments, the leaflet clips 7200 can have any suitable shape to limit interference with the native chordae tendineae.

FIGS. 15-18 show a prosthetic heart valve 8000 in side view (FIG. 15), in front view (FIG. 16), in detailed view (FIG. 17), and in perspective view (FIG. 18), according to an embodiment. The prosthetic heart valve 8000 has a valve body 8100, a first leaflet clip 8200a and a second leaflet clip 8200b (referred to collectively as "clips 8200"). The leaflet clips 8200 are operably coupled to the valve body 8100. The valve body 8100 has a native leaflet retention portion 8140 (also referred to herein as "retention portion") configured to receive a native leaflet and/or the leaflet clips 8200 when the valve body 8100 is disposed within a native annulus of an atrioventricular valve of a heart. The valve body 8100 further includes a first sealing portion 8150a and a second sealing portion 8150b (referred to collectively as "sealing portions 8150"), both of which are configured to provide a fluid seal between the valve body 8100 and a native leaflet when the native leaflet is disposed between the leaflet clips 8200 and the valve body 8100.

The retention portion 8140 can be any suitable size and/or shape, and can be located at any suitable portion of the valve body 8100. For example, the retention portion 8140 can be sized and/or shaped to correspond to (e.g., by shape, size, surface design, texture, etc.) a portion of the leaflet clips 8100 and/or the native leaflets. In this manner, in use, the retention portion 8140 and the leaflet clips 8100 can cooperatively function to substantially maintain one or more native leaflets when the leaflet clips 8200 are disposed in an engaged configuration, i.e., when the leaflet clips 8200 are disposed to capture the one or more native leaflets between the leaflet clips 8200 and the retention portion 8140 of the valve body 8100 when the valve body 8100 is disposed in a native annulus of an atrioventricular valve of a heart.

Figure 15:
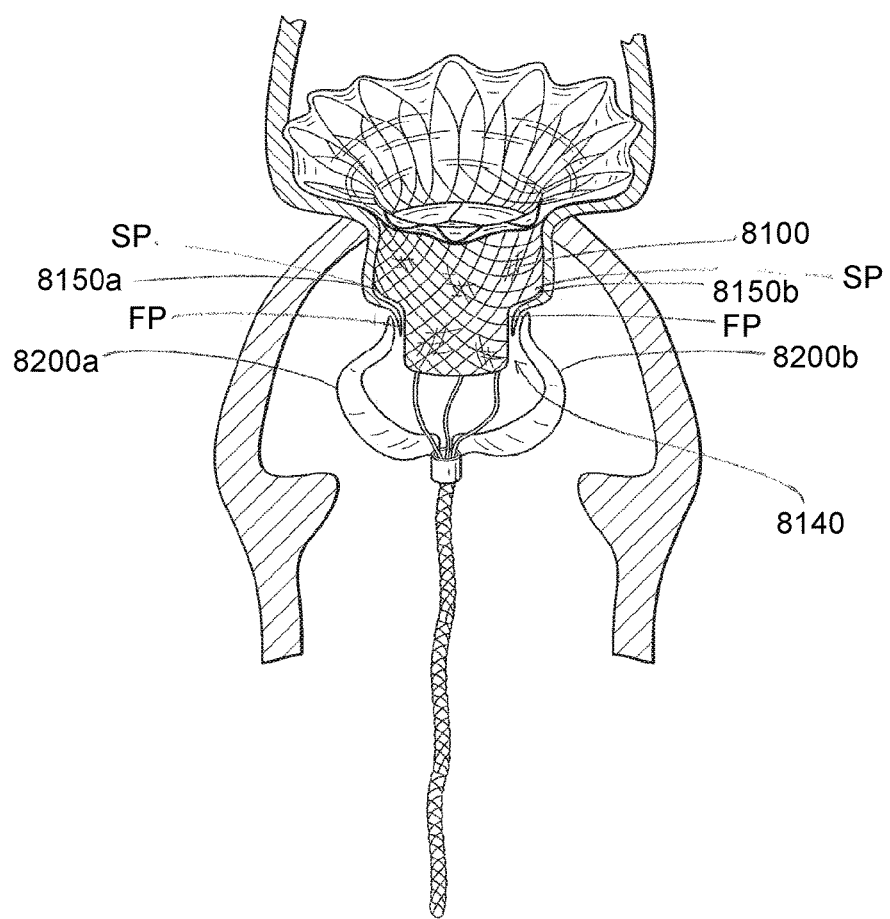
FIGS. 15-18 show a prosthetic heart valve in side view, in front view, in detailed view, and in perspective view, respectively, according to an embodiment.
Figure 16:
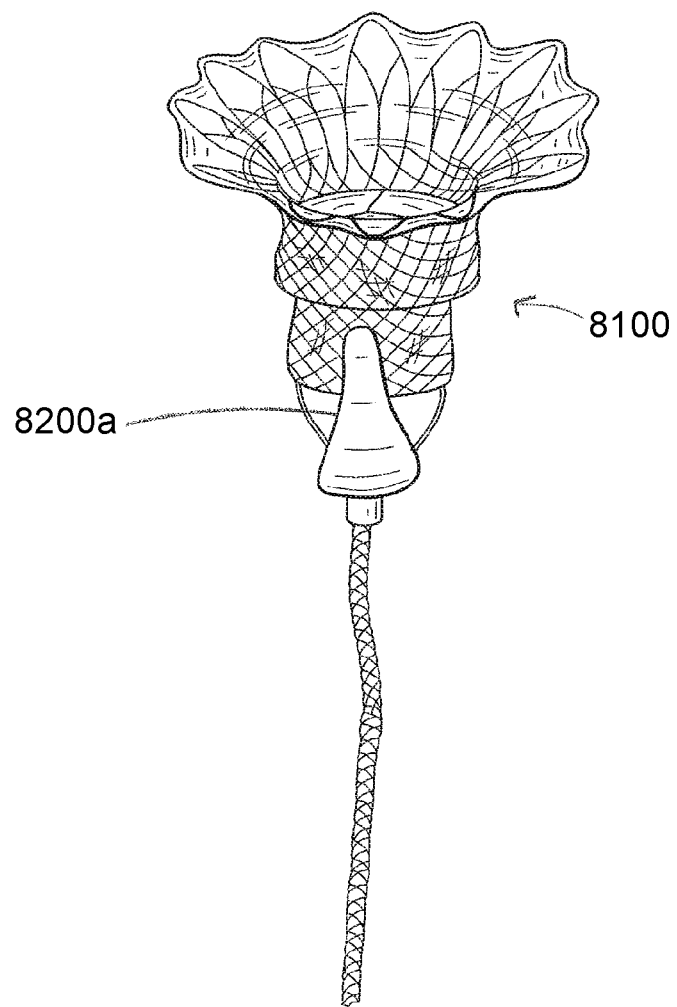
Figure 17:
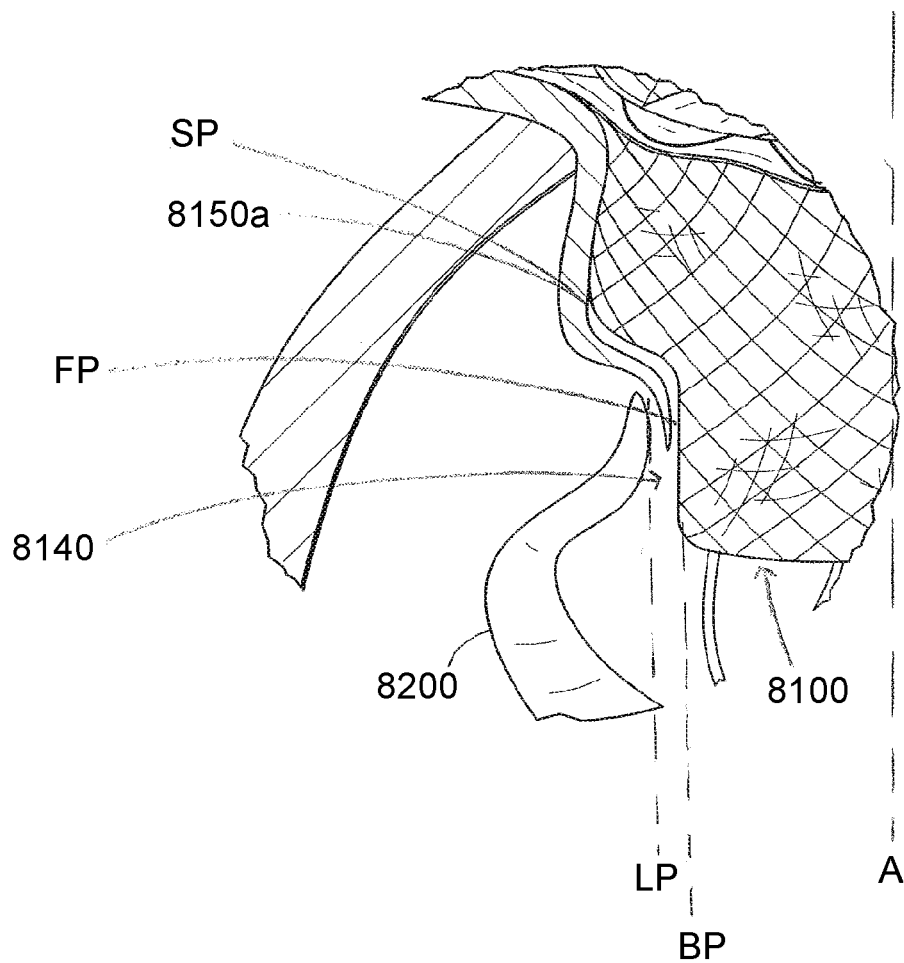

As best shown in FIGS. 15 and 17, the retention portion 8140 can have a diameter smaller than a diameter of a portion of the valve body 8100 proximal to the retention portion 8140. In this manner, the retention portion 8140 can be configured to receive the leaflet clips 8200 such that a diameter of the leaflet clips 8200 (i.e., from an exterior surface of the first leaflet clip 8200a to an exterior surface of the second leaflet clip 8200b) is not larger than the diameter of the portion of the valve body 8100 proximal to the retention portion 8140. Said another way, as shown in FIG. 17, the leaflet clips 8200 define a plane LP, and the portion of the valve body 8100 proximal to the retention portion 8140 defines a plane BP. As shown best in FIG. 17, a distance D1 between the plane LP and a centerline axis A of valve body 8100 is less than a distance D2 between the plane BP and the centerline axis A. Such a configuration allows for and promotes the sealing by the sealing portions 8150, thereby promoting desirable containment of the native leaflet between the valve body 8100 and the leaflet clips 8200. In this manner, the sealing portions 8150 and the leaflet clips 8200 are collectively configured to limit blood flow outside of the prosthetic heart valve 8000 and between the atrium and ventricle of the heart. Further, in use, multiple points of contact, i.e., a first point of contact (FP) between the leaflet clips 8200, a native leaflet, and the valve body 8100, and second point of contact (SP) by the sealing portions 8150 and the valve body 8100, promotes sealing between the atrium and ventricle of the heart.

Moreover, contact at the sealing portions 8150 between the valve body 8100 and a native leaflet promotes desirable seating of the prosthetic heart valve 8000 within the native annulus of the atrioventricular valve. More specifically, in use, a force applied by the leaflet clips 8200 to the native leaflet and the valve body 8100 at the sealing portions 8150 provides a containment force, which promotes sufficient seating of the prosthetic heart valve 8000 within the native annulus of the atrioventricular valve.

Figure 18:
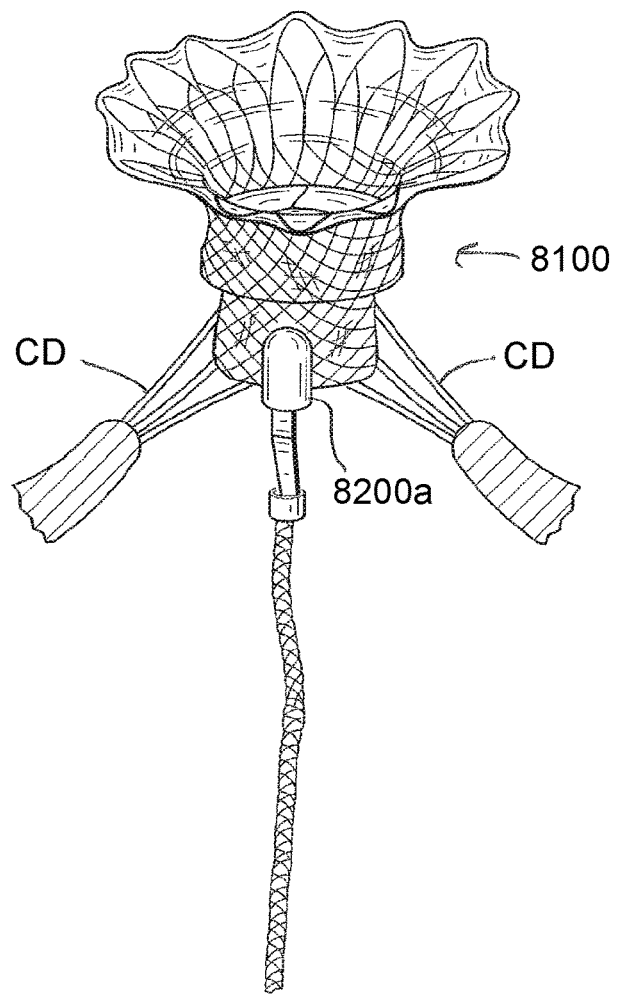

In some embodiments, as best shown in FIG. 18, the leaflet clips 8200 are disposed between, and not in interference with, the chordae tendineae CT within a ventricle of a heart when the valve body 8100 is disposed within the native annulus of the atrioventricular valve. In this manner, the leaflet clips 8200 can transition between various configurations (e.g., between an engaged and disengaged configuration) without undesirable interference with the native chordae tendineae.

Figure 19:
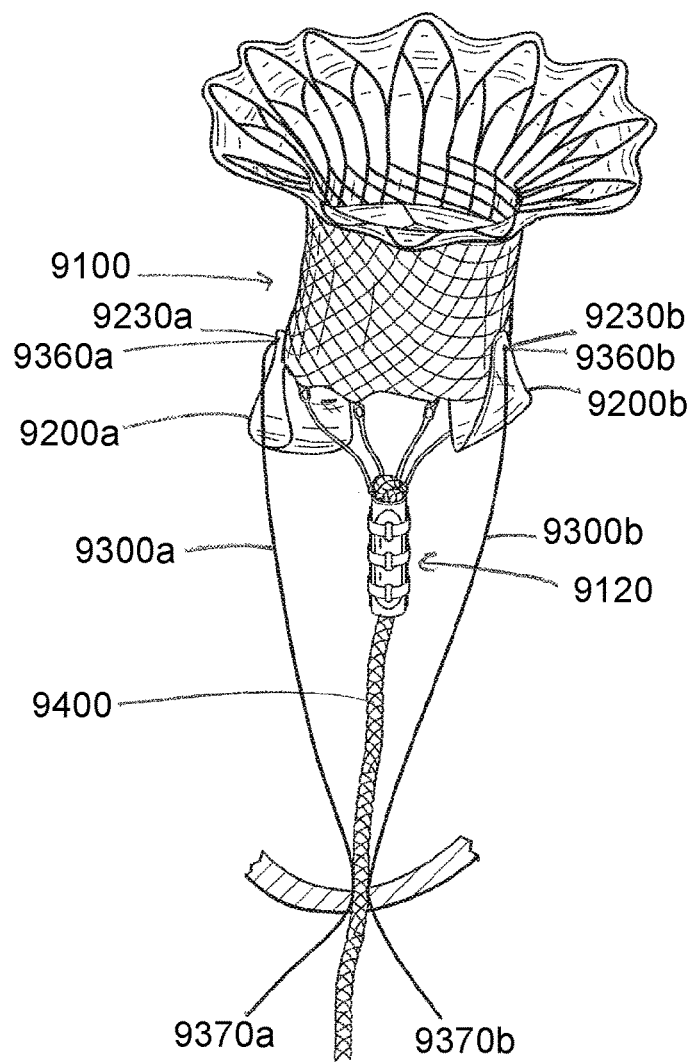
FIG. 19 shows a prosthetic heart valve according to an embodiment.

Referring now to FIG. 19, a prosthetic heart valve system 9000 is shown that includes a prosthetic valve body 9100, an anchoring tether 9400 operably coupled to the valve body 9100, a first leaflet clip 9200a and a second leaflet clip 9200b (referred to collectively as "clips 9200") coupled to the valve body 9100, and a first control element 9300a and a second control element 9300b (referred to collectively as "control elements 9300") operably coupled to the first leaflet clip 9200a and the second leaflet clip 9200b, respectively. The leaflet clips 9200 are movably coupled to the prosthetic valve body 9100 and are configured to be transitioned between a first configuration in which the prosthetic valve 9000 can be inserted into a heart, and a second configuration in which the leaflet clips 9200 are disposed to capture native valve leaflets between the leaflet clips 9200 and the valve body 9100 when the valve body 9100 is disposed in a native annulus of an atrioventricular valve of a heart.

The control elements 9300 are operably coupled to the leaflet clips 9200. In some embodiments, the control elements 9300 are removably coupled to the leaflet clips 9200. The first control element 9300a has a proximal end 9360a and a distal end 9370a. The proximal end 9360a is configured to be operably coupled to a control portion 9230a of the first leaflet clip 9200a. Similarly, the second control element 9300b has a proximal end 9360b and a distal end 9370b. The proximal end 9360b is configured to be operably coupled to a control portion 9230b of the second leaflet clip 9200b. The proximal ends 9360a, 9360b of the control elements 9300 are referred to collectively as "proximal ends 9360" and the distal ends 9370a, 9370b of the control elements 9300 are referred to collectively as "distal ends 9370." In some embodiments, the proximal ends 9360 are configured to be removably coupled to the control portions 9230, of the leaflet clips 9200. The control elements 9300 each have a length sufficient to extend from the leaflet clips 9200, through a ventricle of the heart, and out a wall of the ventricle (e.g., through myocardium) when the valve body 9100 is disposed in the native annulus of the atrioventricular valve of the heart. Said another way, the distal ends 9370 of the control elements 9300 are disposed outside the heart when the proximal ends 9360 are coupled to the leaflet clips 9200 and the valve body 9100 is disposed in the native annulus of the atrioventricular valve.

As described herein, the control elements 9300 are configured to allow a user to transition the leaflet clips 9200 through various configurations. For example, the control elements 9300 can allow a user to transition the leaflet clips 9200 from their first configuration (disengaged) to their second configuration (engaged) when the valve body 9100 is disposed in the native annulus of the atrioventricular valve. More specifically, in use, the user can manipulate the distal ends 9370 of the control elements 9300 to manipulate the leaflet clips 9200 in any suitable manner. For example, the user can move the distal ends 9370 of the control elements 9300 distally to transition the leaflet clips 9200 distally and dispose the leaflet clips 9200 in a disengaged "ready state." Further to this example, the user can move the distal ends 9370 of the control elements 9300 proximally (or allow the distal ends 9370 of the control elements 9300 to move proximally) to transition the leaflet clips 9200 proximally and allow the leaflet clips 9200 to capture a native valve leaflet between the leaflet clips 9200 and the valve body 9100.

Moreover, the user can manipulate the leaflet clips 9200 between various positions and/or configurations (e.g., engaged, partially engaged, disengaged) via the control elements 9300 any suitable number of times. For example, the user can reposition the leaflet clips 9200 after the leaflet clips 9200 have been transitioned to the engaged position, thereby allowing the user to either capture a native leaflet after a failed attempt at capturing the leaflet, or to re-capture the native leaflet.

The anchoring tether 9400 can be the same as or similar to any anchoring tether described in International Patent Application No. PCT/US14/49218, entitled "Epicardial Anchor Devices and Methods," and International Patent Application No. PCT/US12/50740, entitled "Improved Delivery Systems and Methods for Transcatheter Prosthetic Valves," the disclosures of which are incorporated herein by reference in their entirety. The anchoring tether 9400 is operably coupled to a distal end 9120 of the valve body 9100. The anchoring tether 9400 can be used to anchor or secure the prosthetic valve body 9100 when the valve body 9100 is disposed in a native annulus of an atrioventricular valve of a heart. Further, the anchoring tether 9400 can be used to position or reposition the prosthetic valve body 9100 within the heart. The anchoring tether 9400 has a length sufficient to extend from the distal end 9120 of the valve body 9100 through the ventricle of the heart and out the wall of the ventricle when the valve body 9100 is disposed in a native annulus of the atrioventricular valve of the heart.

In use, in some embodiments, the valve body 9100 can be delivered to, deployed, and/or disposed within a native annulus of an atrioventricular valve of a heart when the leaflet clips 9200 are in a disengaged configuration. Similarly stated, the leaflet clips 9200 can remain in the disengaged position until the valve body 9100 is properly seated within the native heart, and/or disposed in a position suitable for manipulation of the leaflet clips 9200. After the valve body 9100 is disposed in the native annulus of the atrioventricular valve, which can be verified using fluoroscopy, or any other imaging technique, the leaflet clips 9200 can be deployed in any suitable manner.

In some embodiments, the valve body 9100 can be repositioned to allow for suitable deployment of the leaflet clips 9200 (e.g., to allow movement of the leaflet clips 9200 within the ventricle of the heart without undesirable interference by a wall of the heart). Similarly stated, the valve body 9100 can be offset from an axis (now shown) defined by a tensioned anchoring tether 9400 before deployment of the one or more of the leaflet clips 9200. For example, the valve body 9100 can be canted away from a posterior wall of the heart to allow adequate space for movement of one of the leaflet clips 9200. In use, once the valve body 9100 is disposed in a proper position for a user to transition one or more of the leaflet clips 9100 from a disengaged position to an engaged position, the user can manipulate one of the control elements 9300 to thereby manipulate one of the leaflet clips 9200. Once one of the leaflet clips 9200 is transitioned into the engaged position such that it properly captures a native leaflet, the valve body 9100 can be repositioned to allow for adequate space for movement of another one of the leaflet clips 9200.

Moreover, in use, the valve body 9100 can be repositioned (e.g., offset from the axis defined by the anchoring tether 9400) in any suitable manner. For example, the anchoring tether 9400 can be manipulated outside the heart by a user, thereby resulting in movement or canting of the valve body 9100. In some embodiments, an elongate member (not shown; can be similar to elongate member 12350 or any other elongate member described herein) defining a lumen configured to receive the anchoring tether 9400 can be used to reposition the valve body 9100 to allow for proper deployment of the leaflet clips 9200. For example, in use, after the valve body 9100 is seated within the native annulus of the atrioventricular valve, the elongate member (not shown) can be introduced into the heart and moved proximally towards the distal end 9120 of the valve body 9100. In this manner, a user can manipulate a distal end of the elongate member (not shown) to reposition the valve body 9100, thereby allowing for adequate space for deployment of the leaflet clips 9200. In some embodiments, the elongate member (not shown) can be operably coupled to the distal end 9120 of the valve body 9100 to promote adequate control of the valve body 9100 by the elongate member (or by a user of the elongate member). In some embodiments, a base member (not shown), defining a tether passageway through which a portion of the anchoring tether 9400 extending from the valve 9100 and outside the heart can be received there-through, can be used to assess a position of and/or reposition the valve body 9100 when the valve body 9100 is disposed in the native annulus of an atrioventricular valve. The base member (not shown) can be the same as or similar to any of the base members described in International Patent Application PCT/US14/49218, entitled "Epicardial Anchor Devices and Methods," the disclosure of which is incorporated herein by reference in its entirety.

Referring now to FIGS. 20a and 20b, a prosthetic heart valve system 10000 is shown that includes a prosthetic valve body 10100, leaflet clips 10200, control elements 10300, and an anchoring tether 10400. The components of the prosthetic heart valve system 10000 (e.g., the valve body 10100, the leaflet clips 10200, and the control elements 10300) can be substantially similar to and/or the same as the components of the prosthetic heart valve system 9000 described above with reference to FIG. 19. Thus, the valve body 10100, the leaflet clips 10200, and the control elements 10300 are not described in further detail herein and should be considered the same as the valve body 9100, the leaflet clips 9200, and the control elements 9300 unless expressly stated otherwise. As described herein, the anchoring tether 10400 can be used to anchor or secure the prosthetic valve body 10100 in the same or similar manner as described above for previous embodiments. As shown in FIG. 20b, the anchoring tether 10400 defines a lumen 10410 through which the control elements 10300 can be disposed. The lumen 10410 has a proximal end 10412 and a distal end 10414, and can be any suitable size and shape configured to receive the control elements 10300. In some embodiments, additional lumens 10410 (not shown) can be included in the anchoring tether 10400. For example, the anchoring tether 10400 can define a first lumen 10410a configured to receive a first control element 10300a, and a second lumen 10410b configured to receive a second control element 10300b.

In use, the control elements 10300 can be disposed in the lumen 10410 of the anchoring tether 10400. More specifically, the control elements 10300 can be routed into the proximal end 10412 of the anchoring tether 10400 and out of the distal end 10414 of the anchoring tether 10400 when the valve body 10100 is disposed within a native annulus of an atrioventricular valve of a heart. Such a configuration consolidates the control elements 10300 and the anchoring tether 10400 thereby reducing or limiting the footprint and friction of the control elements 10300 and the anchoring tether 10400 within the ventricle of the heart. In this manner, undesirable interference or contact between the control elements 10300 and the anchoring tether 10400, and native chordae tendineae of the heart can be reduced or limited.

Moreover, in use, the anchoring tether 10400 and the control elements 10300 are partially disposed outside the heart such that they can be secured, manipulated, or otherwise used by a user. More specifically, as shown in FIG. 20a, the anchoring tether 10400 and the control elements 10300 extend through a puncture site PS of a wall V of a heart. Thus, disposing the control elements 10300 within the anchoring tether 10400 can reduce or limit the size of the puncture site PS, thereby reducing a patient's recovery time associated with the puncture site PS.

FIGS. 21a and 21b show an embodiment of a prosthetic heart valve system 11000 that includes an elongate member 11350 having a first end 11352 configured to be disposed in a ventricle of the heart during deployment of the valve body 11100, and a second end 11354 configured to extend outside the heart. The prosthetic heart valve system 11000 includes a prosthetic valve body 11100, an anchoring tether 11400, leaflet clips 11200, and control elements 11300, which can be configured the same as or similar to the prosthetic valve body 9100, the leaflet clips 9200, the control elements 9300, and the anchoring tether 9400, respectively, described above with reference to FIG. 19. Thus, the valve body 11100, the leaflet clips 11200, the control elements 11300, and the anchoring tether 11400 are not described in further detail herein and should be considered the same as the valve body 9100, the leaflet clips 9200, the control elements 9300, and the anchoring tether 9400 unless expressly stated otherwise.

The elongate member 11350 defines an anchoring tether lumen 11356, a first control element lumen 11358a and a second control element lumen 11358b (referred to collectively as "control element lumens 11358"), and a first leaflet clip attachment portion 11380a and a second leaflet clip attachment portion 11380b (referred to collectively as "leaflet clip attachment portions 11380"). The tether lumen 11356 can be any suitable shape or size configured to receive at least a portion of the anchoring tether 11400. The control element lumen 11358 can be any suitable shape or size configured to receive at least a portion of the control elements 11300. The leaflet clip attachment portions 11380 can be any suitable size or shape configured to receive, and be operably and removably coupled to a control portion 11230a of the first leaflet clip 11200a and a control portion 11230b of the second leaflet clip 11200b (referred to collectively as "control portions 11230").

In use, the anchoring tether 11400 is disposed in the anchoring tether lumen 11356 and extends out the second end 11354 of the elongate member 11350. Similarly, the control elements 11300 are disposed in the control element lumens 11358 and extend out the second end 11354 of the elongate member 11350. Further, the leaflet clips 11200 can be held in a disengaged "ready state" position (first configuration) via the leaflet clips attachment portion 11360 of the elongate member 11350 and the control elements 11300. More specifically, in the first configuration, as shown in FIG. 21a, the control portions 11230 of the leaflet clips 11200 are removably coupled to the elongate member 11356 and the control elements 11300. Further, the control elements 11300 extend from the control portions 11230 to the second end 11354 of the elongate member 11356 and outside the heart.

To transition the leaflet clips 11200 from the disengaged configuration (first position) to the engaged configuration (second position; not shown), the control elements 11300 can be decoupled from the leaflet clips 11200, thereby releasing the leaflet clips 11200 and allowing the leaflet clips 1200 to transition to the engaged configuration. The control elements 11300 can be decoupled from the leaflet clips 11200 in any suitable manner. For example, a portion of control element 11300 can be moved distally (e.g., pulled by a user), resulting in separation of the control elements from the leaflet clips 11200. In this manner, the leaflet clips 11200 can be transitioned from the first configuration to the second configuration, for example, due to shape memory properties of the leaflet clips 11200, when the control elements 11300 are decoupled from the leaflet clips 11200. In some embodiments, the leaflet clips 11200 can be transitioned from the first configuration to the second configuration in response to movement of the elongate member 11350. For example, a user can move the elongate member 11350 distally such that the leaflet clips 11200 are separated from, or otherwise no longer disposed within, the leaflet clip attachment portion 11360. In this manner, the leaflet clips 11200 can be released from the leaflet clip attachment portion 11360, such that the leaflet clips 11200 are no longer contained or otherwise restricted in the first configuration by the elongate member 11350. In some embodiments, after the leaflet clips 11200 are decoupled from the elongate member 11350, the leaflet clips can transition, without manipulation by the control elements 11300, from the disengaged configuration to the engaged configuration. In other embodiments, after the leaflet clips 11200 are decoupled from the elongate member 11350, the leaflet clips can be manipulated between configurations by the control elements 11300. In the second configuration, the leaflet clips 11200 are disposed to capture one or more native valve leaflets between the leaflet clips 11200 and the valve body 11100 when the valve body 11100 is disposed in a native annulus of an atrioventricular valve.

Although the elongate member 11350 defines control element lumens 11358, in other embodiments, the elongate member 11350 can instead, or in addition, define control element channels (not shown) along the outside of the elongate member 11350. In this manner, the control element channels can function the same and/or similar to the control element lumens 11358 described herein.

Referring now to FIGS. 22a-23b, a prosthetic heart valve system 12000 is shown that includes a prosthetic valve body 12100, a first leaflet clip 12200a including a control portion 12230a and a second leaflet clip 12200b including a control portion 12230b (referred to collectively as "leaflet clips 12200"), a first control element 12300a and a second control element 12300b (referred to collectively as "control elements 12300"), anchoring tether 12400, and an elongate member 12350. The components of the prosthetic heart valve system 12000 (e.g., the valve body 12100, the leaflet clips 12200, and the control elements 12300) can be substantially similar to and/or the same as the components of the prosthetic heart valve system 11000 described above with reference to FIGS. 21a and 21b. Thus the valve body 12100, the leaflet clips 12200, and the control elements 12300 are not described in further detail herein and should be considered the same as the valve body 11100, the leaflet clips 11200, and the control elements 11300 unless expressly stated otherwise. As described herein the anchoring tether 12400 can be used to anchor or secure the prosthetic heart valve body 12100 in the same or similar manner as described above for previous embodiments.

The elongate member 12350 defines a first control element lumen 12358a, a second control element lumen 12358b, a third control element lumen 12358c, and a fourth control element lumen 12358d (referred to collectively as "control element lumens 12358," all through which the control elements 12300 can be disposed, and a tether lumen 12356 configured to receive the anchoring tether 12400. The control element lumens 12358 have proximal ends 12412 and distal ends 12414, and can be any suitable size and shape configured to receive at least a portion of the control elements 12300. In some embodiments, additional lumens (not shown) can be included in the elongate member 12350, for example, to accommodate additional control elements.

In use, the control elements 12300 can be disposed in the control element lumens 12358. More specifically, the first control element 12300*a* can be routed proximally through the first control element lumen 12358*a* from its distal end 12414*a* (not shown) to its proximal end 12412*a* (not shown), operably coupled to the control portion 12230*a* of the first leaflet clip 12200*a* (e.g., looped through an aperture defined by the control portion 12230*a*), then routed distally through the second control element lumen 12358*b* from its proximal end 12412*b* to its distal end 12414*b* and extending outside the heart. In this manner, a user can manipulate the first leaflet clip 12200*a*, and subsequently remove the first control element from the leaflet clip 12200*a* and the patient's body. Similarly, the second control element 12300*b* can be routed proximally through the third control element lumen 12358*c* from its distal end 12414*c* to its proximal end 12412*c*, operably coupled to the control portion 12230*b* of the second leaflet clip 12200*b* (e.g., looped through an aperture defined by the control portion 12230*b*), then routed distally through the fourth control element lumen 12358*d* from its proximal end 12412*d* to its distal end 12414*d* and extending outside the heart. In this manner, a user can independently manipulate the second leaflet clip 12200*a*, and subsequently remove the first control element from the leaflet clip 12200*a* and the patient's body.

Figure 22A:
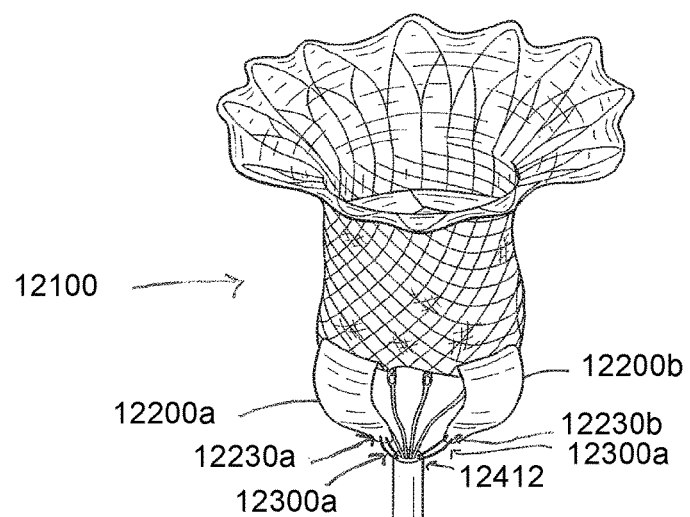
FIGS. 22a-23b show a prosthetic heart valve in a first configuration, a section top view of the same, the prosthetic heart valve in a second configuration, and a sectional top view of the same, respectively, according to an embodiment.
Figure 22B:
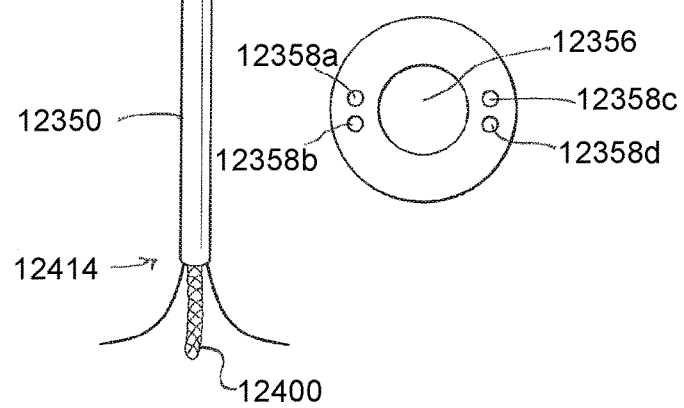
Figure 23A:
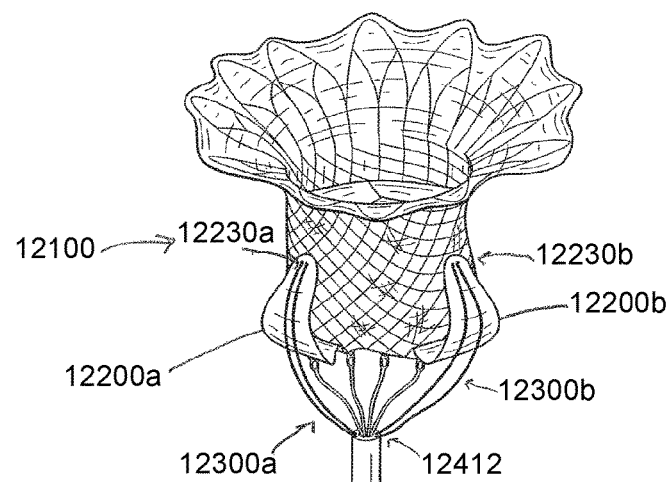
Figure 23B:
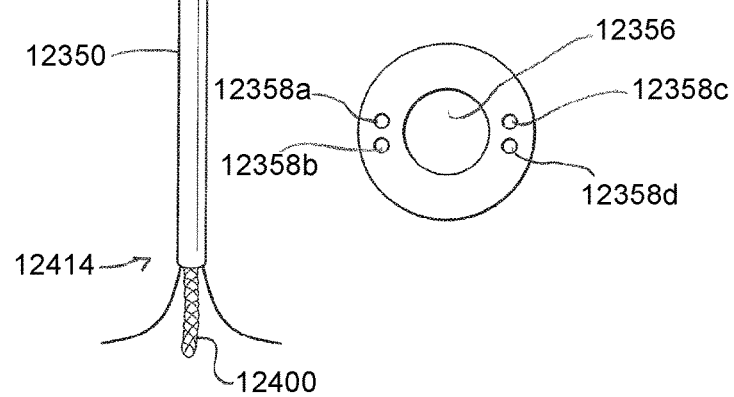

Moreover, in use, the control elements 12300 can be moved distally outside the heart such that the leaflet clips 12200 are transitioned into a disengaged "ready state," shown best in FIG. 22*a*. Further, the control elements 12300 can be moved proximally (e.g., released) from outside the heart such that the leaflet clips 12200 are transitioned into an engaged configuration, shown best in FIG. 23*a*. After the leaflet clips 12200 are transitioned into the engaged configuration, the positioning of the leaflet clips can be verified using fluoroscopy, or any other imaging technique. If any of the leaflet clips 12200 are not properly positioned (e.g., one or more leaflet clips 12200 have not adequately captured a native valve leaflet), one or more control elements 12300 can be moved distally outside the heart to transition the leaflet clip(s) 12200 back to the disengaged configuration to allow repositioning of the valve body 12100 or additional attempts at capturing the native valve leaflets.

After the leaflet clips 12200 have captured the native leaflets and their positioning verified, the control elements 12300 can be removed from the ventricle of the heart by pulling a first end of the control elements 12300, and releasing a second end of the control elements 12300. For example, the control elements 12300 (e.g., sutures) can include four free ends disposed outside the heart. To decouple the control elements 12300 from the leaflet clips 12200, two free ends from the four free ends can be moved distally outside the heart. In this manner, the remaining two free ends will translate proximally through two of the control element lumens 12358, and then distally through the two remaining control element lumens 12358, thereby allowing for decoupling of the control elements 12300 from the leaflet clips 12200 and removal of the control elements 12300 from the ventricle of the native heart valve.

In other embodiments, the prosthetic heart valve system 12000 can include additional control elements (not shown). For example, the prosthetic heart valve system 1200 can include the first control element 12300*a*, the second control element 12300*b*, a third control element, and a fourth control element. In such embodiments, the control elements can include four distinct elements (e.g., four distinct sutures). Further, the first leaflet clip 12200*a* can include a first control portion 12230*a* and a second control portion. Similarly, the second leaflet clip 12200*b* can include a first control portion 12230*b* and a second control portion. The first control portion 12230*a* and the second control portion of the first leaflet clip 12200*a* can be configured to be operably and removably coupled to the first control element 12300*a* and the third control element, respectively. Similarly, the first control portion 12230*b* and the second control portion of the second leaflet clip 12200*b* can be configured to be operably and removably coupled to the second control element 12300*b* and the fourth control element, respectively. In use, the control elements described in this embodiment can be routed individually from the leaflet clips 12200 through the control element lumens 11358, and outside the heart.

Referring now to FIGS. 24-26*d*, a prosthetic heart valve system 13000 is shown that includes a prosthetic valve body 13100, leaflet clips 13200, control elements 13300, an elongate member 13350, and an anchoring tether 13400. The components of the prosthetic heart valve system 13000 (e.g., the valve body 13100, the leaflet clips 13200, the elongate member 13350, and the control elements 13300) can be substantially similar to and/or the same as the components of the prosthetic heart valve system 12000 described above with reference to FIGS. 23*a* and 23*b*. Thus, the valve body 13100, the leaflet clips 13200, the elongate member 13350, and the control elements 13300 are not described in further detail herein and should be considered the same as the valve body 12100, the leaflet clips 13200, and the control elements 12300 unless expressly stated otherwise. As described herein the anchoring tether 13400 can be used to anchor or secure the prosthetic valve body 13100 in the same or similar manner as described above for previous embodiments.

Figure 24:
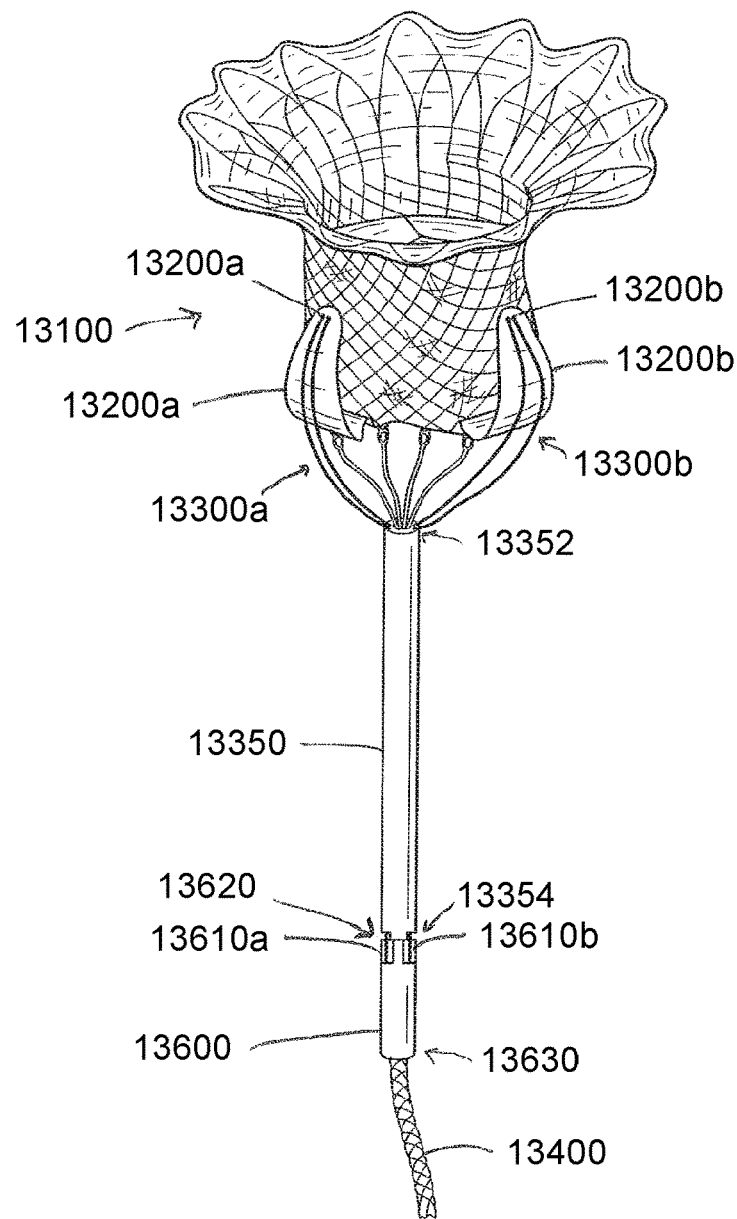
FIG. 24 shows a prosthetic heart valve according to an embodiment.

The elongate member 13350 has a proximal end 13352 configured to be disposed in a ventricle of the heart during deployment of the valve body 13100, and a distal end 13354 configured to extend outside the heart and be operably coupled to a tubular body 13600. The elongate member 13350 can be coupled to the tubular body 13600 in any suitable manner (e.g., using any suitable fastener or fastening method, a screw, wire, an interference fit, laser welding, etc.). For example, as shown in FIG. 24, the elongate member 13350 can receive a proximal end 13620 of the tubular body 13600. As best shown in FIGS. 25*a* and 25*b*, the elongate member 13350 defines a first control element lumen 13358*a*, a second control element lumen 13358*b*, a third control element lumen 13358*c*, and a fourth control element lumen 13358*d* (referred to collectively as "control element lumens 13358") all through which the control elements 13300 can be disposed. The elongate member 13350 further defines a tether lumen 13356 there-through configured to receive the anchoring tether 13400. The control element lumens 13358 can be any suitable size and shape configured to receive at least a portion of the control elements 13300. In some embodiments, additional lumens (not shown) can be included in the elongate member 13350.

Figure 26A:
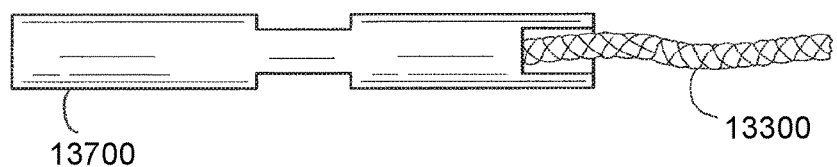
FIGS. 26a-d show a mandrel coupled to a control element, a tubular member in top and side views, and a tubular member with a mandrel disposed therein, of the prosthetic heart valve of FIG. 24, according to an embodiment.
Figure 26B:
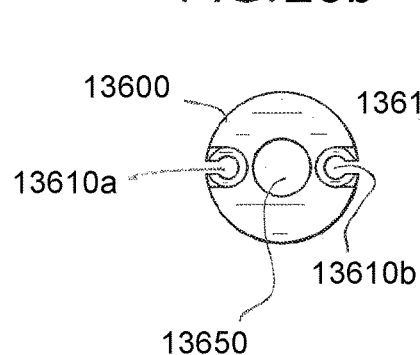
Figure 26C:
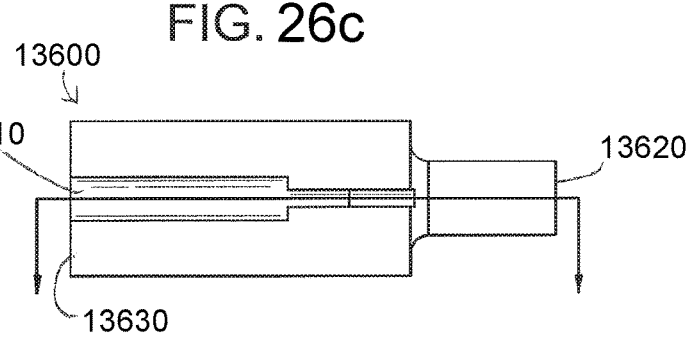
Figure 26D:
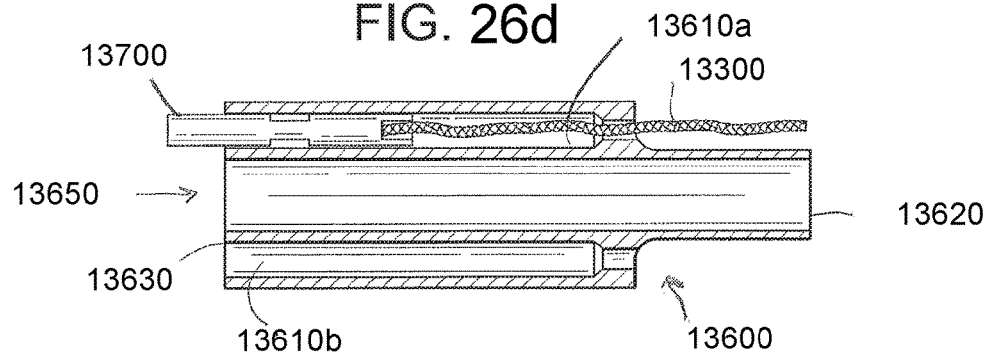

As best shown in FIG. 26*a*, each of the control elements 13300 are coupled to a mandrel 13700. The tubular body 13600 has a proximal end 13620 and a distal end 13630, and defines a first mandrel slot 13610*a* at a first radial location, and a second mandrel slot 13610*b* and a second radial location, and a lumen 13650 extending from the proximal end 13620 to the distal end 13630. The first and second slots 13610*a*, 13610*b* are referred to collectively as "mandrel slots 13610" and are configured to receive the mandrels 13700 in any suitable manner (e.g., a keyed joint) to removably couple the control elements 13300 to the tubular body 13600 (FIG. 26*d*). Moreover, a retaining element (not shown) can be disposed on the tubular body 13600 to retain the mandrels 13700 in the mandrel slots 13610 until the control elements 13300 are ready to be used to deploy the leaflet clips 13200.

In some embodiments, some or all of the components described herein (e.g., the elongate member 13350, the tubular body 13600, etc.) can be provided separately and joined together in preparation for delivery and deployment of the prosthetic valve 13000 (referred to as "loading the valve"). For example, to load the valve, the elongate member 13350 can be slidably disposed about the anchoring tether 13400. Similarly stated, the anchoring tether 13400 can be disposed in the tether lumen 13356 of the elongate member 13350. The proximal end 13620 of the tubular member 13600 can be coupled to the distal end 13354 of the elongate member 13350 such that the anchoring tether 13400 extends from the proximal end 13352 of the elongate member 13350, through the tether lumen 13356 of the elongate member 13350, and continuing through the tether lumen 13650 of the tubular member 13600 from its proximal end 13620 to its distal end 13610. A first end of each control element 13300 can be coupled to each mandrel 13700 and a second end of each control element 13300 can be coupled to any suitable location within the elongate member 13350. For example, as best shown in FIG. 25*a*, one end of the control element 13300 can be disposed in and coupled to the control element lumen 13358*a* of the elongate member 13350, while the other end of the control element 13300 can be coupled to the mandrel 13700. Further to this example, the mandrel 13700 can be routed distally through the control portion 13200*a* of the leaflet clip 13200*a*, and then proximally through the control element lumen 13358*b* from the proximal end 13352 of the elongate member 13350 to the distal end 13354 of the elongate member 13350, and then into the mandrel slot 13610*a*. In this manner, each mandrel 13700 can be operably coupled to a leaflet clip 13200, and can be disposed in the mandrel slots 13610 of the tubular member 13600 until the control elements 13300 are ready to be used to deploy the leaflet clips 13200.

In use, each mandrel 13700 can be released from their respective mandrel slots 13610 in any suitable manner (e.g., both mandrels 13700 can be released substantially simultaneously, or at distinct times). In this manner, the leaflet clips 13200 can be manipulated together or separately. Once released, each mandrel 13700 can be routed through a control element lumen 13358 from the distal end 13354 to the proximal end 13352 of the elongate member 13350. For example, the elongate member 13350 can be pulled distally such that each mandrel 13700 translates through a control element lumen 13358 and out from the proximal end 13352 of the elongate member 13350. As the mandrels 13700 translate proximally towards the proximal end 13352 of the elongate member 13350, the leaflet clips 13200 can transition positions between a disengaged position and an engaged position, thereby capturing one or more native leaflets. After the leaflet clips 13200 are disposed in a suitable position (e.g., after leaflet capture), the control elements 13200, elongate member 13350, tubular member 13600, and mandrels 13700 can be decoupled from the valve body 13100 and removed from a patient's heart. During removal, in some embodiments, the mandrels 13700 can be routed through the control portions 13200 of the leaflet clips 13200. In other embodiments, the mandrels 13700 can be decoupled from the control elements 13300 (e.g., cut away).

Figure 27:
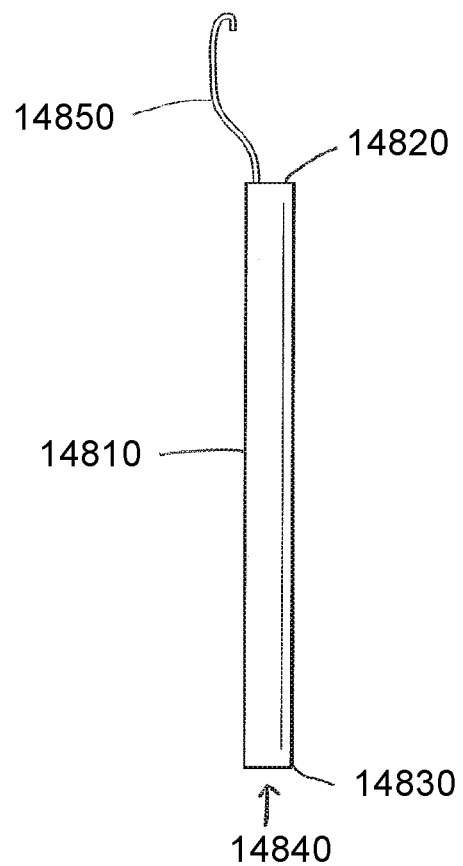
FIG. 27 shows a leaflet clip retrieval member according to an embodiment

Referring now to FIG. 27, a leaflet clip retrieval member 14800 (also referred to as "retrieval member 14800") is shown that includes an elongate member 14810 having a proximal end 14820, a distal end 14830, and defining a tether lumen 14840 there-through. The retrieval member 14800 also includes a leaflet contact portion 14850 (also referred to as "contact portion 14850") coupled to, or disposed at, the proximal end 14820 of the elongate member 14810. In some embodiments, the elongate member 14810 and the contact portion 14850 can be monolithically constructed. In other embodiments, the elongate member 14810 and the contact portion 14850 can be formed separately and then joined together (e.g., using any suitable fastener or fastening method, such as a screw, a wire, an interference fit, laser welding, etc.). In some embodiments, a portion of the contact portion 14850 can be disposed in the elongate member 14810. For example, the elongate member 14810 can define a contact portion lumen (not shown) configured to receive at least a portion of the contact portion 14850. The contact portion lumen (not shown) can be distinct from the tether lumen 14840.

The retrieval member 14800 is configured to manipulate one or more leaflet clips (e.g., any of the leaflet clips described in any of the embodiments herein). Further, the retrieval member 14800 is configured to be inserted through a puncture site (not shown) in a wall of a heart (not shown), translate proximally towards a prosthetic heart valve (e.g., any of the prosthetic heart valves described in any of the embodiments herein) such that the contact portion 14850 can be coupled to a leaflet clip to manipulate a leaflet clip. In this manner, the retrieval member 14800 can be configured to manipulate a leaflet clips from an engaged configuration to a disengaged configuration. In use, during retrieval of a prosthetic heart valve from within a native annulus of an atrioventricular valve of a heart, the retrieval member 14800 can manipulate the leaflet clips such that the leaflet clips are in a favorable position for removal from the heart (e.g., without a native leaflet disposed between the leaflet clip and the prosthetic valve body). The contact portion 14850 of the retrieval member 14800 can be any suitable size, shape or configuration suitable to attach to and manipulate a leaflet clip. For example, the contact portion 14850 can be hook-shaped and configured to be operably coupled to a leaflet clip (e.g., a control portion of a leaflet clip). As another example, the contact portion 14850 can be configured to pierce a covering of a leaflet clip, and thereby grab the leaflet clip for subsequent manipulation thereof.

The tether lumen 14840 can be any suitable size, shape or configuration suitable to receive an anchoring tether (e.g., any of the anchoring tethers described in any of the embodiments herein). In use, the retrieval member 14800 can be moved proximally towards a prosthetic valve body disposed in a native annulus of an atrioventricular valve. More specifically, the retrieval member 14800 can be moved along an anchoring tether (not shown) disposed within the tether lumen 14840 of the elongate member 14810. In this manner, the anchoring tether can serve as a guide for the retrieval member 14800. During removal of the prosthetic valve, a user can translate the retrieval member 14800 proximally along the anchoring tether, thereby allowing the contact portion 14850 to contact and manipulate a leaflet clip (e.g., disengage the leaflet clip), and then translate the retrieval member 14800 distally such that the retrieval member 14800 can be removed from the heart.

Figure 28:
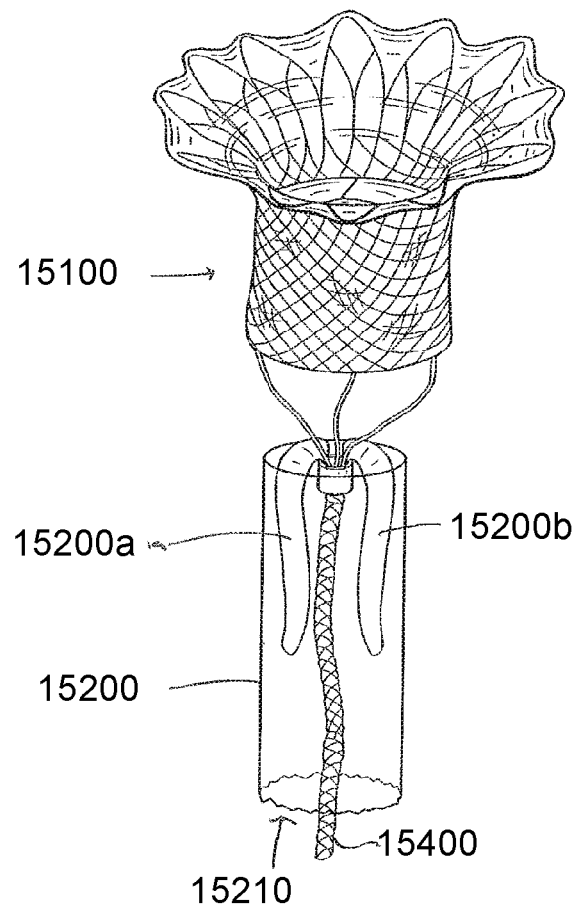
FIGS. 28 and 29 show a prosthetic heart valve in a first configuration and a second configuration, respectively, according to an embodiment.
Figure 29:
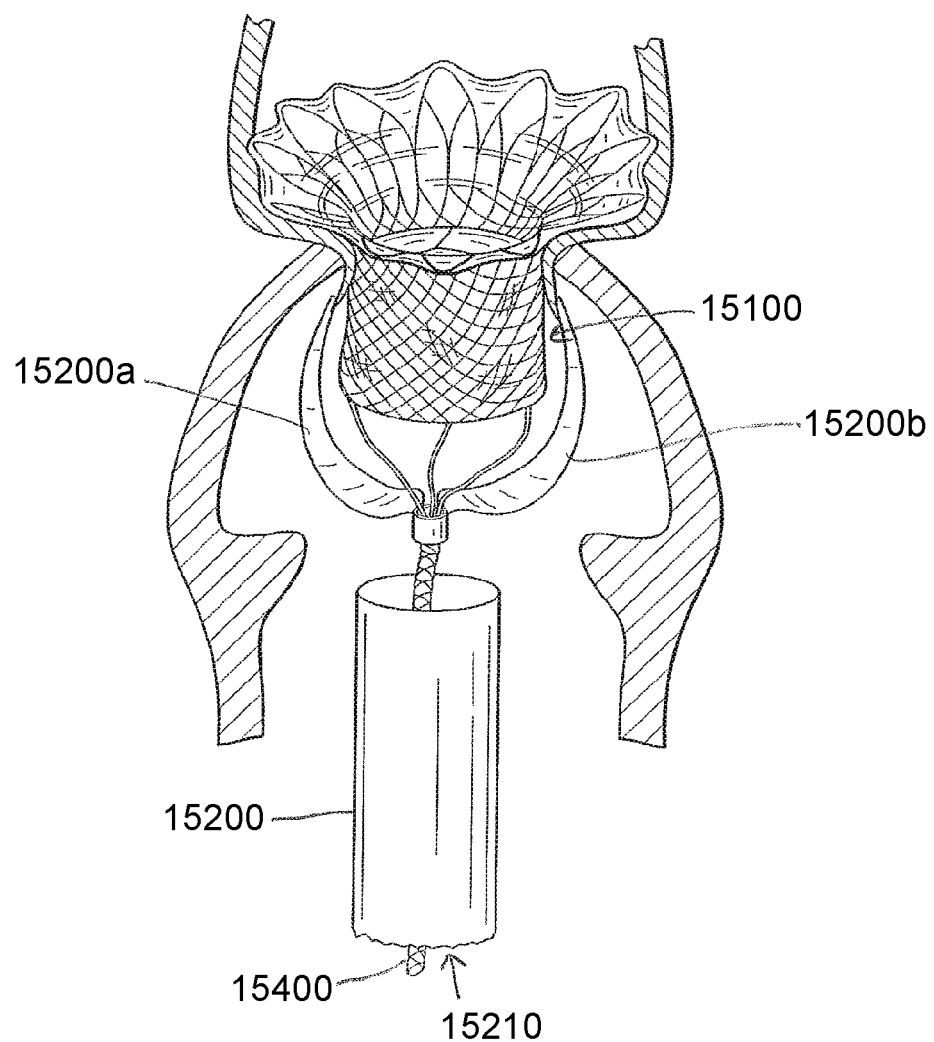

Referring now to FIGS. 28 and 29, a prosthetic heart valve system 15000 is shown that includes a prosthetic valve body 15100, an anchoring tether 15400 operably coupled to the valve body 15100, a first leaflet clip 15200a and a second leaflet clip 15200b (referred to collectively as "clips 15200") coupled to the valve body 15100, a control element 15300 operably coupled to the first leaflet clip 15200a and the second leaflet clip 15200b. The leaflet clips 15200 are movably coupled to the prosthetic valve body 15100 and are configured to be transitioned between a first configuration in which the prosthetic valve 15000 can be inserted into a heart, and a second configuration in which the leaflet clips 15200 are disposed to capture native valve leaflets between the leaflet clips 15200 and the valve body 15100 when the valve body 15100 is disposed in a native annulus of an atrioventricular valve of a heart.

The control element 15300 is operably and removably coupled to the leaflet clips 15200, and configured to be slidably disposed about the anchoring tether 15400. The control element 15200 defines a lumen 15210 there-through configured to receive the anchoring tether 15400 and the leaflet clips 15200. As described herein the control element 15300 is configured to allow a user to transition the leaflet clips 15200 through various positions. For example, the control element 15300 can allow a user to transition the leaflet clips 15200 from their first configuration (disengaged), as shown in FIG. 28, to their second configuration (engaged), as shown in FIG. 29, when the valve body 15100 is disposed in the native annulus of the atrioventricular valve. More specifically, in use, the user can manipulate the control element 15300 to manipulate the leaflet clips 15200 in any suitable manner. For example, the user can move the control element 15300 distally to transition the leaflet clips 15200 from their disengaged configuration to their engaged configuration, thereby allowing the leaflet clips 15200 to capture a native valve leaflet between the leaflet clips 15200 and the valve body 15100. More specifically, the leaflet clips 15200 can be in a deformed, disengaged configuration when disposed within the lumen 15210 of the control element 15200, for example, during delivery of the prosthetic heart valve 15000. To capture the native leaflets, the control element 15200 can be moved distally, or otherwise separated from the leaflet clips 15200, thereby allowing the leaflet clips 15200 return to their undeformed, engaged configuration, and allowing the leaflet clips 15200 to capture a native valve leaflet between the leaflet clips 15200 and the valve body 15100. In some embodiments, the prosthetic heart valve 15000 can include additional control elements (e.g., control elements 9300, or any other suitable control element described herein).

Figure 30:
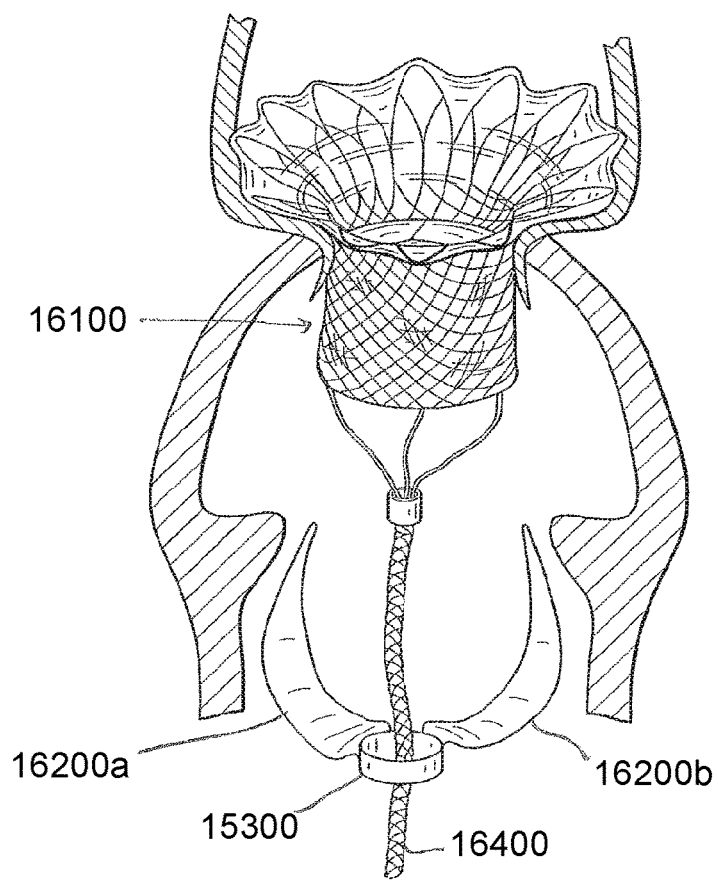
FIGS. 30 and 31 show a prosthetic heart valve in a first configuration and a second configuration, respectively, according to an embodiment.
Figure 31:
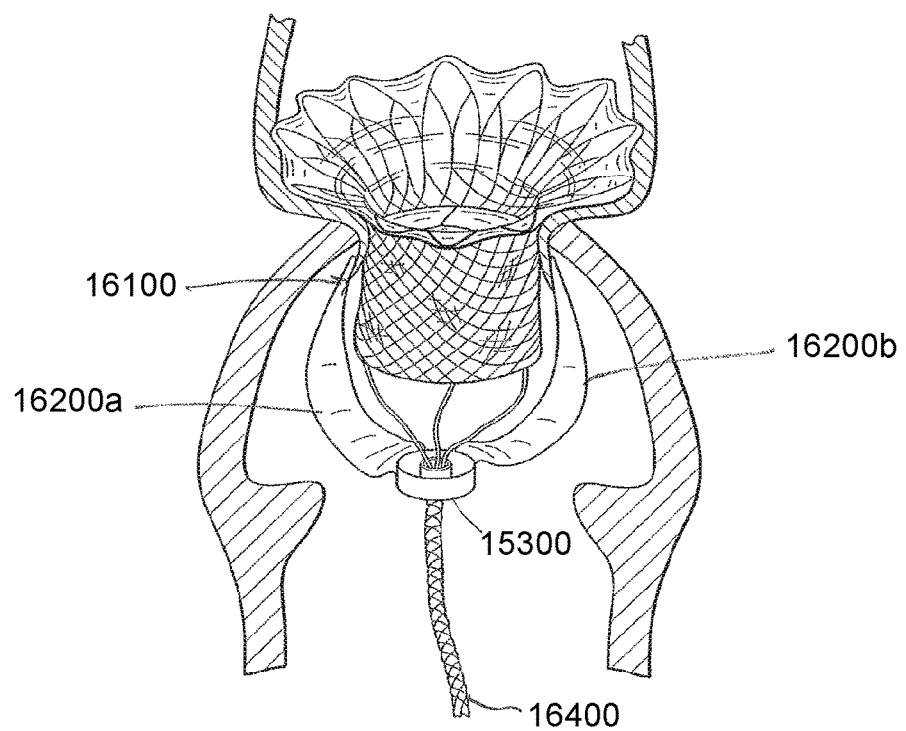

Referring now to FIGS. 30 and 31, a prosthetic heart valve system 16000 is shown that includes a prosthetic valve body 16100, an anchoring tether 16400 operably coupled to the valve body 16100, a control element 16300 operably coupled to the anchoring tether 16400, and a first leaflet clip 16200a and a second leaflet clip 16200b (referred to collectively as "clips 16200") coupled to the control element 16300. The leaflet clips 16200 are movably coupled to the control element 16300 and are configured to be transitioned between a first configuration (FIG. 30) in which the leaflet clips are not in contact with native leaflet clips, and a second configuration (FIG. 31) in which the leaflet clips 16200 are disposed to capture native valve leaflets between the leaflet clips 16200 and the valve body 16100 when the valve body 16100 is disposed in a native annulus of an atrioventricular valve of a heart.

The control element 16300 is operably the leaflet clips 16200, and configured to be slidably disposed about the anchoring tether 16400. The control element 16300 defines a lumen 16210 there-through configured to receive the anchoring tether 16400. As described herein the control element 16300 is configured to allow a user to transition the leaflet clips 16200 through various positions. For example, the control element 16300 can allow a user to transition the leaflet clips 16200 from their first configuration (disengaged), as shown in FIG. 30, to their second configuration (engaged), as shown in FIG. 31, when the valve body 16100 is disposed in the native annulus of the atrioventricular valve. More specifically, in use, the user can manipulate the control element 16300 to manipulate the leaflet clips 16200 in any suitable manner. For example, the user can move the control element 16300 distally to transition the leaflet clips 16200 from their disengaged configuration to their engaged configuration, thereby allowing the leaflet clips 16200 to capture a native valve leaflet (not shown) between the leaflet clips 16200 and the valve body 16100. In use, the leaflet clips 16200 can be in an undeformed, disengaged configuration when disposed within the atrium of a heart valve, for example, during delivery of the prosthetic heart valve 16000. To capture the native leaflets, the control element 16200 can be moved distally to allow the leaflet clips 16200 to engage one or more native leaflets (not shown) such that the leaflet clips 16200 can capture a native valve leaflet between the leaflet clips 16200 and the valve body 16100. In some embodiments, the control element 16300 and the leaflet clips 16200 can be delivered to the native valve substantially simultaneously with delivery of the prosthetic valve body 16100 to the native annulus of the valve. In other embodiments, the control element 16300 and the leaflet clips can be delivered to the native valve subsequent to delivery and/or seating of the prosthetic valve body 16100 within the native annulus of the valve.

Figure 32A:
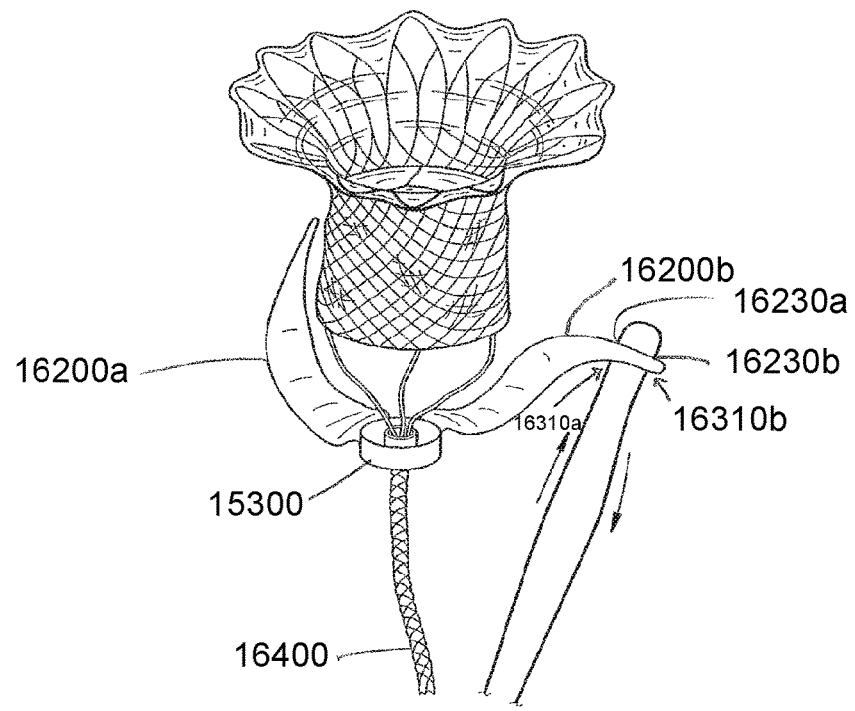
FIGS. 32a and 32b shows the prosthetic heart valve of FIGS. 30 and 31, and a detailed view of the same, respectively, according to another embodiment.

In some embodiments, the prosthetic heart valve 16000 can include additional control elements (e.g., control elements 9300, or any other suitable control element described herein). For example, referring now to FIGS. 32a and 32b, in addition to control element 16300 (referred to in this example as first control element 16300a), the prosthetic valve 16000 can include a second control element 16300b operably coupled to the second leaflet clip 16200b, and configured to manipulate the second leaflet clip 16200b in any suitable manner (e.g., between engaged, disengaged, deformed, and undeformed configurations). In some embodiments, the second control element 16300b can be removably coupled to the second leaflet clip 16200b. In some embodiments, the prosthetic valve 16000 can include a third control element (not shown) operably coupled to the first leaflet clip 16200a, and configured to manipulate the first leaflet clip 16200a in any suitable manner (e.g., between engaged, disengaged, deformed, and undeformed configurations).

Figure 32B:
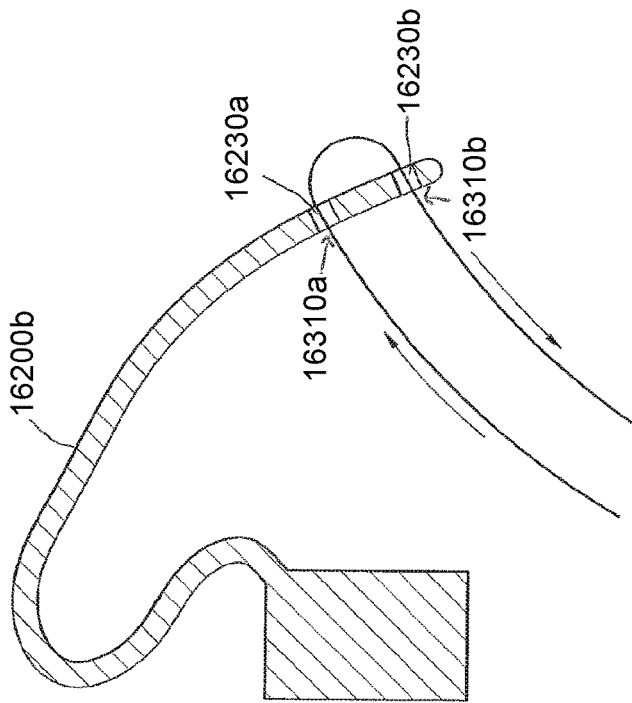

Referring now also to FIG. 32b, the second leaflet clip 16200b is shown coupled to the second control element 16300b. The second leaflet clip 16200b defines a first control portion lumen 16230a and a second control portion lumen 16230b (referred to collectively as "control portion lumens 16230"). The control portion lumens 16230 are configured to receive a portion of the second control element 16300b. In use, a first portion 16310a of the second control element 16300b can be routed through the first control portion lumen

16230*a*, and a second portion 16310*b* of the second control element 16300*b* can be routed through the second control portion lumen 16230*b*. In this manner, in use, the first portion 16310*a* and the second portion 16310*b* can be collectively manipulated to manipulate the second leaflet clip 16200*b* between various positions and/or configurations. Further, to decouple the second control element 16300*b* from the second leaflet clip 16200*b*, the first portion 16310*a* of the second control element 16300*b* can be moved through the first control portion lumen 16230*a* and the second control portion lumen 16230 a distance sufficient to remove the second element 16300*b* from both the lumen 16230*a* and the lumen 16230*b*.

Figure 33A:
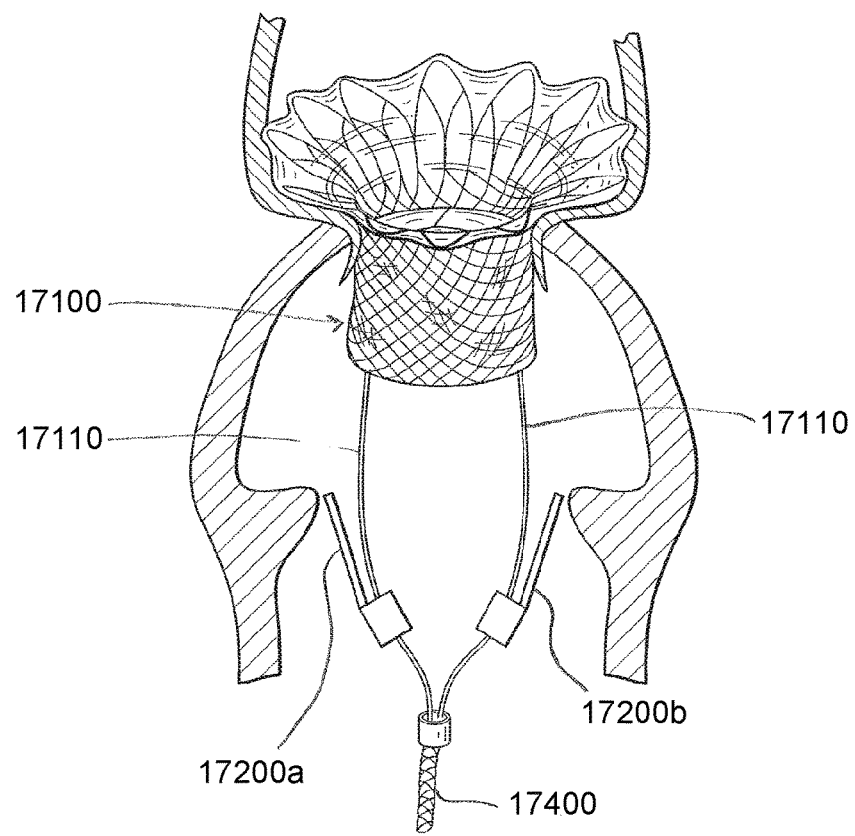
FIGS. 33a-34 show a prosthetic heart valve in a first configuration, a second configuration, and in a detailed view, respectively, according to an embodiment.
Figure 33B:
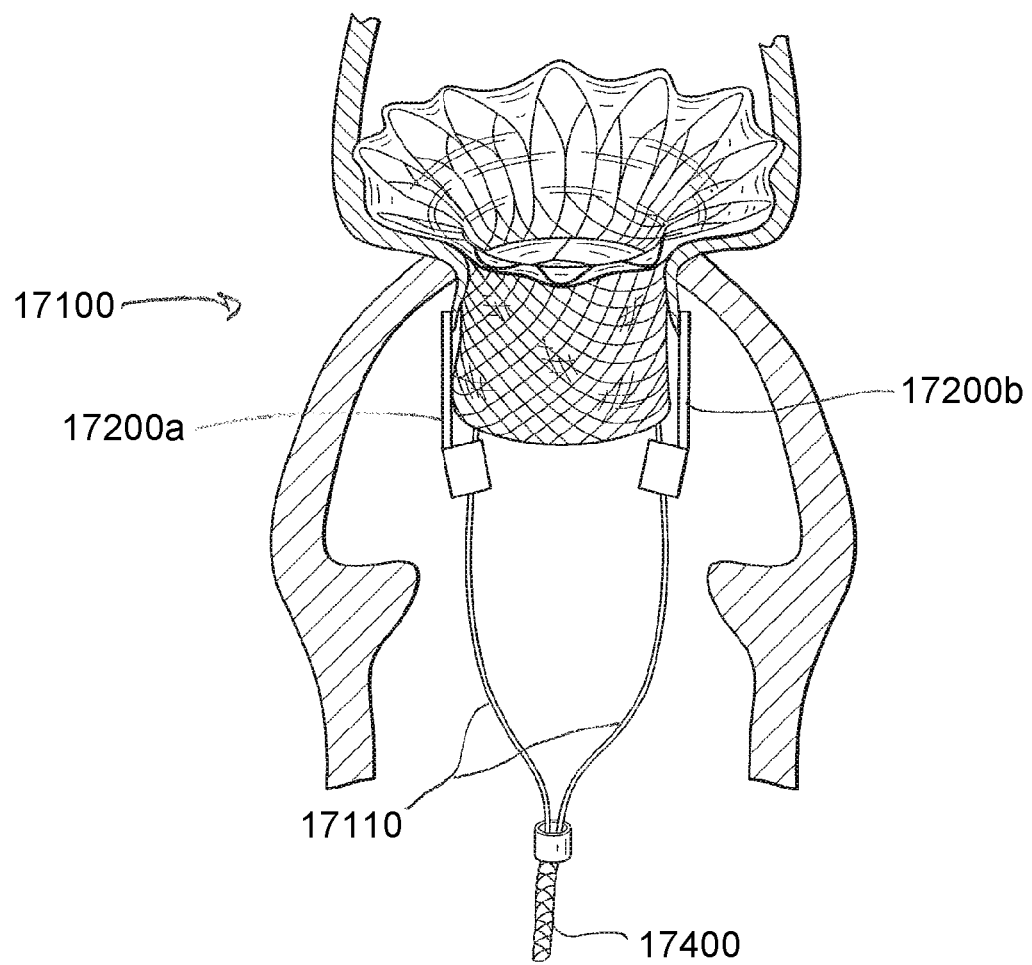
Figure 34:
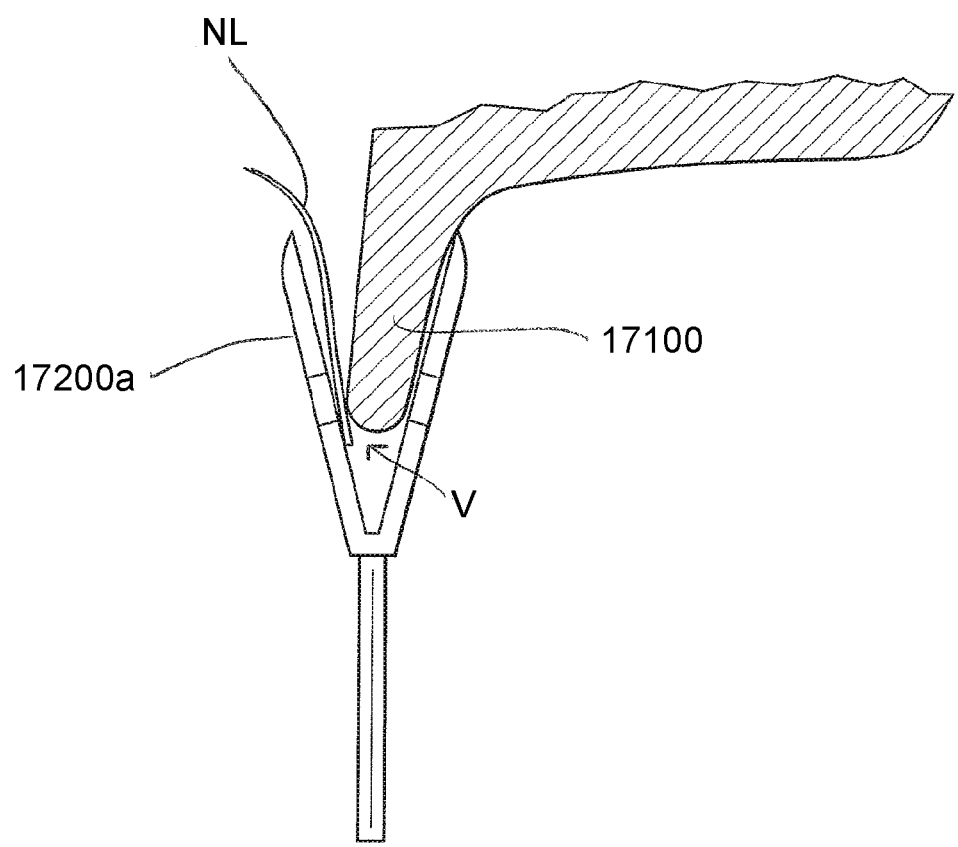

Referring now to FIGS. 33*a*-34, a prosthetic heart valve system 17000 is shown that includes a prosthetic valve body 17100 having a leaflet clip delivery portion 17110, an anchoring tether 17400 operably coupled to the valve body 17100, a control element (not shown) optionally operably coupled to the anchoring tether 17400, and a first leaflet clip 17200*a* and a second leaflet clip 17200*b* (referred to collectively as "clips 17200") operably coupled to the control element (not shown) and movably and slideably coupled to the leaflet clip delivery portion 17110. The leaflet clips 17200 are configured to be transitioned between a first configuration (FIG. 33*a*) in which the leaflet clips 17200 are not in contact with native leaflet clips, and a second configuration (FIG. 33*b*) in which the leaflet clips 17200 are disposed to capture native valve leaflets between the leaflet clips 17200 and the valve body 17100 when the valve body 17100 is disposed in a native annulus of an atrioventricular valve of a heart.

The leaflet clips 17200 are configured to transition between a disengaged configuration (FIG. 33*a*) and an engaged configuration (FIG. 33*b*). In use, the leaflet clips 17200 can be translated between configurations via the leaflet clip delivery portion 17110. In this manner, the leaflet clips 17200 can transition distally from the disengaged configuration (FIG. 33*a*) to the engaged configuration (FIG. 33*b*), thereby allowing the leaflet clips 17200 to capture a native valve leaflet NL between the leaflet clips 17200 and the valve body 17100.

Referring now to FIG. 34, the leaflet clip 17200*a* is shown, accordingly to another embodiment. The leaflet clip 17200*a* has a fork-like or claw-like shape configured to capture a native leaflet in a volume V defined therein. For example, the leaflet clip 17200*a* can be configured to receive a portion of a native leaflet NL and a portion of the valve body 17100. In this manner, the leaflet clip 17200 can secure the native leaflet NL between the leaflet clip 17200 and the valve body 17100. In use, as described herein, the leaflet clip 17200*a* can be disposed in the engaged configuration such that the native leaflet NL and a portion of the valve body 17100 are disposed in volume V. In some embodiments, an interior portion of the leaflet clip 17200*a* can have any suitable configuration (e.g., any suitable surface design) suitable to receive and/or retain a native leaflet when the leaflet clip 17200*a* is disposed in an engaged configuration.

In an alternative embodiment, leaflet clips can be manipulated independently during the delivery of a prosthetic mitral valve and before the delivery device used to deliver the prosthetic mitral valve (also referred to herein as "prosthetic valve") is removed from the heart. In this manner, the leaflet clips can be manipulated (e.g., actuated) in conjunction with orientation (e.g., axial or radial positioning) of the prosthetic valve. In some instances, for example, a user may want to reposition the prosthetic valve after the prosthetic valve has been delivered and deployed, and the leaflet clips have been actuated to capture the native leaflets. In such instances, it can be desirable to uncouple the leaflet clips from the native leaflets (i.e., separate the leaflet clips from the native valve leaflets) to facilitate repositioning of the prosthetic valve. In this embodiment, a user can deploy or position the prosthetic valve and actuate the leaflet clips to capture the native leaflets, then manipulate the leaflet clips to decouple the leaflet clips from the native leaflets, reposition the valve using the delivery device, and then re-actuate the leaflet clips to capture the native leaflets, all while the delivery device remains at least partially within the heart. In this manner, in some instances, it is unnecessary to insert and deliver to the heart a second device (e.g., a repositioning device) after removal of the delivery device from the heart.

Referring now to FIGS. 35A-35D, a schematic illustration of a prosthetic heart valve system 18000 is shown that includes a prosthetic valve body 18100, a first leaflet clip 18200*a* and a second leaflet clip 18200*b* (referred to collectively as "leaflet clips 18200"), a first control element 18300*a* and a second control element 18300*b* (referred to collectively as "control elements 18300"), a first control element manipulator 18310*a* (also referred to herein as "first manipulator") a second control element manipulator 18310*b* (also referred to herein as "second manipulator") (referred to collectively as "manipulators 18310"), a first connecting member 18316*a* and a second connecting member 18316*b* (referred to collectively as "connecting members 18316"), and a delivery device 18350. The components of the prosthetic heart valve system 18000 (e.g., the valve body 18100, the leaflet clips 18200, the control elements 18300) can be substantially similar to and/or the same as the components of the prosthetic heart valve system 12000 described above with reference to FIGS. 22A-23B. Thus, some of the components of the prosthetic heart valve system 18000 are not described in further detail herein and should be considered similar to the prosthetic heart valve system 12000 unless expressly stated otherwise. Further, an anchoring tether (not shown) can be used to anchor or secure the prosthetic heart valve body 18100 in the same or similar manner as described above for previous embodiments.

Figure 35C:
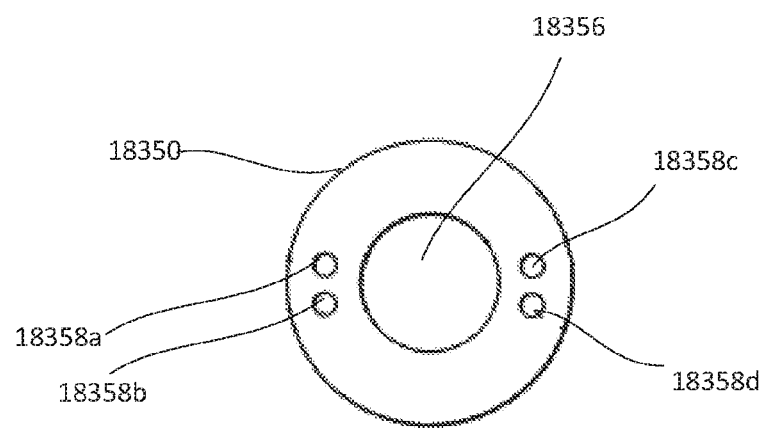
FIG. 35C shows a top view of a delivery device of the prosthetic heart valve system shown in FIG. 35A.

As shown in FIG. 35C, the delivery device 18350 defines a first control element lumen 18358*a*, a second control element lumen 18358*b*, a third control element lumen 18358*c*, and a fourth control element lumen 18358*d* (referred to collectively as "control element lumens 18358," all through which the control elements 18300 can be disposed), and a tether lumen 18356 configured to receive an anchoring tether (not shown) and the prosthetic valve body 18100 during delivery of the valve body 18100 to the heart. The control element lumens 18358 have distal ends 18412 (labeled 18412*a*, 18412*b*, 18412*c*, 18412*d* in FIG. 35A) and proximal ends 18414 (labeled 18414*a*, 18414*b*, 18414*c*, 18414*d* in FIG. 35A), and can be any suitable size and shape configured to receive at least a portion of the control elements 18300. In alternative embodiments, additional lumens can be defined by the delivery device 18350, for example, to accommodate additional control elements.

In use, the control elements 18300 can be slidably disposed in the control element lumens 18358. More specifically, the first control element 18300*a* can be routed proximally through the first control element lumen 18358*a* from its distal end 18412*a* to its proximal end 18414*a*, be operably coupled to the first leaflet clip 18200*a* (e.g., looped through an aperture (not shown) defined by the first leaflet clip 18200*a*), then routed distally through the second control element lumen 18358*b* from its proximal end 18414*b* to its distal end 18412*b*, and extend outside the delivery device

18350 where it is formed into a loop 18313*a*. For example, the two free ends of the control element 18300*a* can be coupled to the connecting member 18313*a* to form a loop portion extending from the connecting member 18313*a*. In some embodiments, the first connecting member 18316*a* is slidably coupled to the first control element 18300*a*, and the second connecting member 18316*b* is slidably coupled to the second control element 18300*b*, as described in more detail herein with respect to removal of the delivery device 18350 from the heart. In some embodiments, the two free ends of the control element 18300*a* can be tied to form a loop outside the distal end 18412*a* of the delivery device 18350. Similarly, the second control element 18300*b* can be routed proximally through the third control element lumen 18358*c* from its distal end 18414*c* to its proximal end 18412*c*, be operably coupled to the second leaflet clip 18200*b* (e.g., loop through an aperture defined by the second leaflet clip 18200*b*), then routed distally through the fourth control element lumen 18358*d* from its proximal end 18412*d* to its distal end 18414*d*, and extend outside the delivery device 18350 where it is formed into a loop 18313*b*.

As shown in FIG. 35A, the first manipulator 18310*a* can be removably coupled to the loop 18313*a* of the first control element 18300*a* and the second manipulator 18310*b* can be removably coupled to the loop 18313*b*. For example, in this embodiment, a proximal end portion of the manipulators 18310*a* 18310*b* includes a hook portion 18315*a*, 18315*b*, respectively, configured to receive or grasp the loops 18313*a* and 18313*b*, respectively, of a corresponding control element 18300*a*, 18300*b*. FIG. 35B is an enlarged view of the manipulator 18310*a* illustrating the hook portion 18315*a* (although not shown, manipulator 18310*b* can include a similar hook portion). In this manner, with the manipulators 18310*a* and 18310*b* coupled to the loops 18313*a* and 18313*b*, a user can manipulate the first leaflet clip 18200*a* by pulling and/or releasing the first manipulator 18310*a* and can manipulate the second leaflet clip 18200*b* by pulling and/or releasing the second manipulator 18310*b*. For example, once the valve body 18100 is positioned (e.g., radially oriented) at a desired location, tension applied to the first manipulator 18310*a* can be released thereby allowing the first leaflet clip 18200*a* to transition to its engaged configuration in which the leaflet clip 18200*a* sandwiches a native leaflet (not shown) between the first leaflet clip 18200*a* and the valve body 18100. Similarly, tension applied to the second manipulator 18310*b* can be released thereby allowing the second leaflet clip 18200*b* to return to its biased position such that the leaflet clip 18200*b* can sandwich a native leaflet (not shown) between the second leaflet clip 18200*b* and the valve body 18100.

Further, as shown in FIG. 35A, a proximal end portion of each manipulator 18310*a*, 18310*b* is coupled to or includes an actuator that can be grasped or otherwise handled by a user. In this embodiment, a proximal end portion of each manipulator 18310*a*, 18310*b* includes an actuator knob 18320*a*, 18320*b*. Each actuator knob 18320*a*, 18320*b* can include a retaining element 18322*a*, 18322*b* (e.g., a set screw) that can retain or couple a portion of the manipulator 18310*a*, 18310*b*, to the respective actuator knob 18320*a*, 18320*b*. Each actuator knob 18320*a*, 18320*b* can further include a sealing member 18324*a*, 18324*b* configured to seal or close-off a volume or space defined within the respective actuator knobs 18320*a*, 18320*b*.

In this embodiment, the manipulators 18310 can be used to actuate (and release and re-actuate) the leaflet clips 18200 before removal of the delivery device 18350 from the heart. In this manner, in use, the valve body 18100 can be positioned and repositioned (with use of the delivery device 18350) after one or more actuations or re-actuations of the leaflet clips 18200, and prior to removal of the delivery device. For example, in some instances, the valve 18100 can be delivered via the delivery device 18350 and at least partially deployed within the native annulus of the heart after at least a portion of the valve 18100 exits the delivery device 18350. The leaflet clips 18200 can then be actuated independently (e.g., released to their biased positions) in response to a user manipulating or releasing tension on the manipulators 18310 by actuating the actuator knobs 18320. To reposition the valve 18100, a user can manipulate the knobs 18320 of the manipulators 18310 to disengage the leaflet clips 18200 from the native leaflets and a portion of the valve body 18100. For example, the user can rotate the actuator knobs 18320, which can in turn pull the manipulators 18310. Upon such disengagement, a portion of the valve 18100 can be pulled back into the delivery device 18350 and repositioned or reoriented by manipulation of the delivery device 18350. After repositioning the valve 18100, the user can re-actuate independently the leaflet clips 18200 as discussed above. As such, this embodiment facilitates delivery and positioning of the valve 18100 and capturing of the native leaflets, by allowing repeated actuation of the leaflet clips 18200 and repeated positioning and deployment of the valve 18100 in any suitable order as may be desired.

Upon proper positioning of the valve 18100 and actuation of the leaflet clips 18200, the delivery device 18350 can be removed from the heart. Because the leaflet clips 18200 are actuated or engaged with the native leaflets prior to removal of the delivery device 18350, the leaflet clips 18200 can facilitate securement of the position and orientation of the valve 18100 as the delivery device 18350 is removed, thereby limiting or preventing undesirable movement of the valve 18100 during removal of the delivery device 18350 from the heart. Similarly stated, the leaflet clips 18200, when engaged with the native leaflets, can support the valve 18100 and limit undesirable movement thereof in response to removal of the delivery device 18350.

Figure 35D:
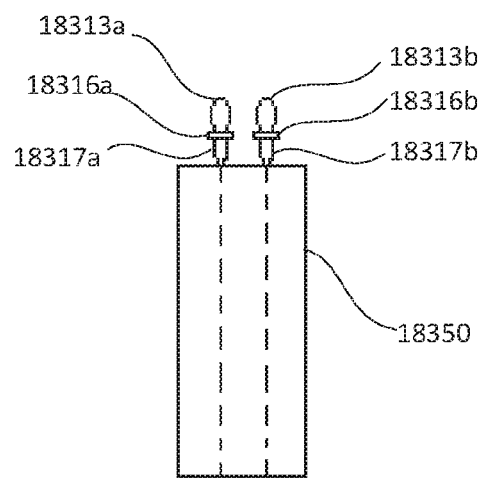
FIG. 35D shows a side view of a portion of the prosthetic heart valve system shown in FIG. 35A.

To remove the first control element 18300*a* from the heart, the first connecting member 18316*a* can be slid distally along the first control element 18300*a* to expose a portion 18317*a* of the first control element 18300*a* between the connecting member 18316*a* and the distal end of the delivery device 18350, as shown in FIG. 35D. The exposed portion 18317*a* of the first control element 18300*a* can be cut, and then the first manipulator 18310*a* can be pulled distally such that an end of the first control element 18300*a* proximal to the cut is routed through the control element lumens 18358*a*, 18358*b*, the first leaflet clip 18200*a*, and out of the distal end 18412*a* of the delivery device 18350. In this manner, the first control element 18300*a* can be decoupled from the first leaflet clip 18200*a*, and pulled through the delivery device 18350 and out of the heart.

Similarly, to remove the second control element 18300*b* from the heart, the second connecting member 18316*b* can be slid distally along the second control element 18300*b* to expose a portion 18317*b* of the second control element 18300*b* between the connecting member 18316*b* and the distal end of the delivery device 18350, as shown in FIG. 35D. The exposed portion 18317*b* of the second control element 18300*b* can be cut, and then the first manipulator 18310*b* can be pulled distally such that an end of the second control element 18300*b* proximal to the cut is routed through the control element lumens 18358*c*, 18358*d*, the second leaflet clip 18200*a*, and out of the distal end 18412*d* of the delivery device 18350. In this manner, the second control element 18300*b* can be decoupled from the first leaflet clip 18200*b*, pulled through the delivery device 18350 and out of the heart.

Figure 36:
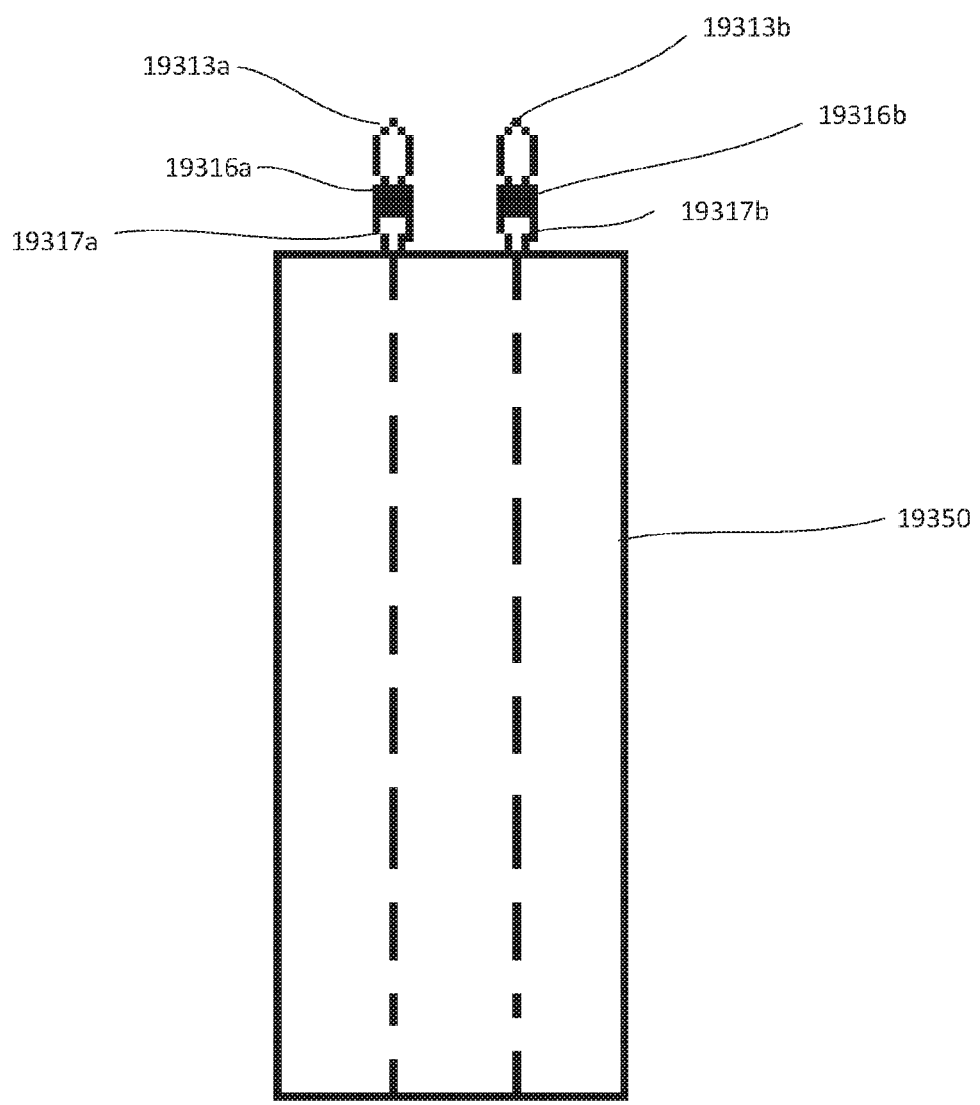
FIG. 36 shows a side view of a portion of a prosthetic heart valve system, according to an embodiment.

In alternative embodiments, the connecting members can be knots formed with the control elements or separate devices removably attachable to the control elements. FIG. 36 shows a schematic illustration in side view of a portion of a prosthetic heart valve system 19000, including a delivery device 19350, a first control element 19300*a* and a second control element 19300*b* (referred to collectively as "control elements 19300"), a first connecting member 19316*a* and a second connecting member 19316*b* (referred to collectively as "connecting members 19316"). The components of the prosthetic heart valve system 19000 (e.g., the valve body (not shown), the leaflet clips (not shown), the control elements (not shown)) can be substantially similar to and/or the same as the components of the prosthetic heart valve system 18000 described above with reference to FIGS. 35A-35D. Thus, some of the components of the prosthetic heart valve system 19000 are not shown or described in further detail herein and should be considered similar to the prosthetic heart valve system 18000 unless expressly stated otherwise. Further, an anchoring tether (not shown) can be used to anchor or secure the prosthetic heart valve body (not shown) in the same or similar manner as described above for previous embodiments.

In use, the control elements 19300 can be manipulated similar to or the same as control elements described above for previous embodiments. In this embodiment, the connecting members 19316 are arranged to in part form the loops 19313, and are positioned between the loops 19313 and exposed portions 19317 of the control elements 19300, as shown in FIG. 36.

In some embodiments in which the connecting members 19316 are knots, to remove the control elements 19300 (including the connecting members 19316), the exposed portions 19317 of the control elements 19300 can be cut and routed or pulled through the delivery device 19350, separated from the leaflet clips (not shown), and removed from the heart, similar to as described with respect to the prosthetic heart valve system 18000.

In some embodiments in which the connecting members 19316 are a separate device coupled to the control elements 19300, to remove the control elements 19300 (and the connecting members 19316), the exposed portions 19317 of the control elements 19300 can be released from the connecting members 19316, and the control elements 19300 can be routed or pulled through the delivery device 19350, separated from the leaflet clips (not shown), and removed from the heart, similar to as described with respect to the prosthetic heart valve system 18000.

Figure 37:
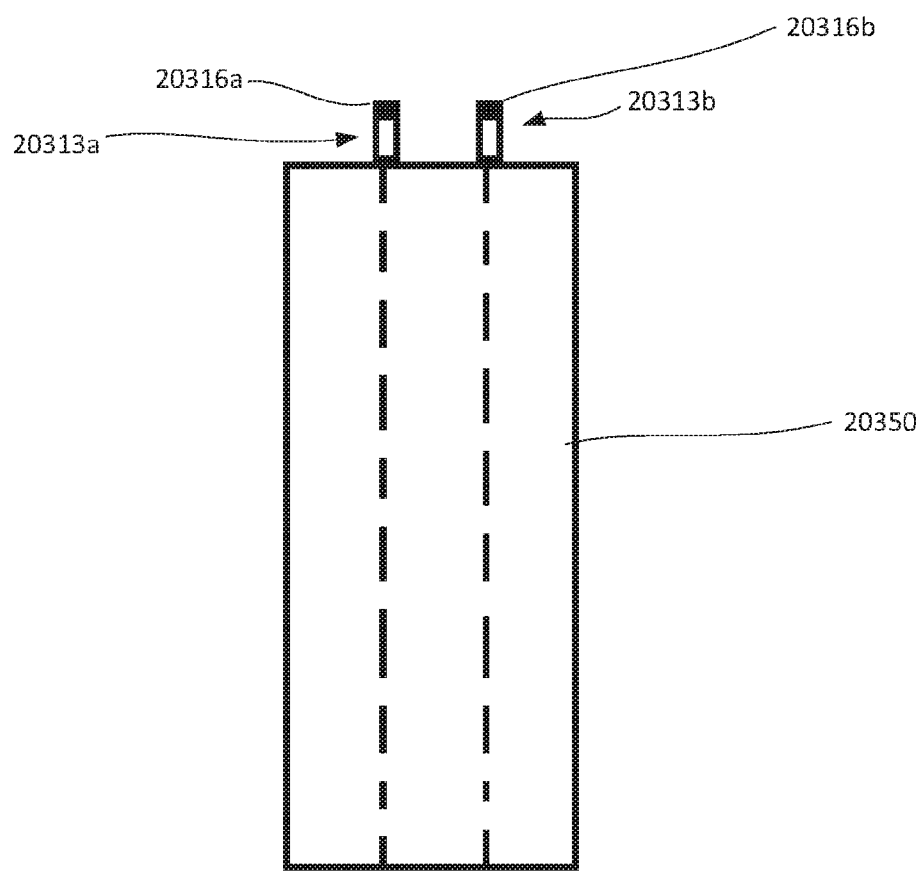
FIG. 37 shows a side view of a portion of a prosthetic heart valve system, according to an embodiment.

In an alternative embodiment, the connecting members can be disposed distal to the loops of the control elements. For example, as shown schematically in FIG. 37, a portion of a prosthetic heart valve system 20000 includes a delivery device 20350, a first control element 20300*a* and a second control element 20300*b* (referred to collectively as "control elements 20300"), a first connecting member 20316*a* and a second connecting member 20316*b* (referred to collectively as "connecting members 20316") disposed distal to loops 20313 (a first loop 20313*a* and a second loop 20313*b*) of the control elements 20300. The components of the prosthetic heart valve system 20000 (e.g., the valve body (not shown), the leaflet clips (not shown), the control elements (not shown)) can be substantially similar to and/or the same as the components of the prosthetic heart valve system 18000 described above with reference to FIGS. 35A-35D. Thus, some of the components of the prosthetic heart valve system 20000 are not shown or described in further detail herein and should be considered similar to the prosthetic heart valve system 18000 unless expressly stated otherwise. Further, an anchoring tether (not shown) can be used to anchor or secure the prosthetic heart valve body (not shown) in the same or similar manner as described above for previous embodiments.

In use, the control elements 20300 can be manipulated similar to or the same as control elements described above for previous embodiments. In this embodiment, however, the connecting members 20316 are coupled and disposed distal to the loops 20313. In this manner, to the remove the control elements 20300 (and the connecting members) from the heart, the connecting members 20316 can each be separated from one end of each control element 20300, and pulled distally similar to as described above with respect to prosthetic heart valve system 18000 and prosthetic heart valve system 19000. Alternatively, in some instances, a portion of the loops 20313 can be cut and routed through the delivery device 20350, separated from the leaflet clips (not shown), and removed from the heart, similar to as described with respect to the prosthetic heart valve system 18000 and the prosthetic heart valve system 19000.

While various embodiments have been particularly shown and described, various changes in form and details may be made. While embodiments have been described above, it should be understood that they have been presented by way of example only, and not limitation. Although various embodiments have been described as having particular features and/or combinations of components, other embodiments are possible having any combination or sub-combination of any features and/or components from any of the embodiments described herein. Moreover, any suitable combination of components described herein can be physically and/or operably coupled together to form prosthetic heart valve with leaflet clips configured, for example, to capture native valve leaflets and provide an improved seal between the prosthetic heart valve and the native valve annulus.

The specific configurations of the various components can also be varied. For example, the size and specific shape of the various components can be different from the embodiments shown, while still providing the functions as described herein. More specifically, the size and shape of the various components can be specifically selected depending on native valve annulus size and/or native valve leaflet size or position.

Where methods and/or events described above indicate certain events and/or procedures occurring in certain order, the ordering of certain events and/or procedures may be modified. Additionally, certain events and/or procedures may be performed concurrently in a parallel process when possible, as well as performed sequentially as described above.

What is claimed is:
1. A system comprising:
a collapsible and expandable prosthetic heart valve body having a proximal end and a distal end;
first and second leaflet clips, each of the first and second leaflet clips being coupled to the prosthetic heart valve body and configured to be transitioned between a first condition in which the body can be inserted into a native annulus of an atrioventricular valve of a heart, and a second condition, in which the leaflet clip is adapted to capture a native valve leaflet such that the native valve leaflet is engaged between the leaflet clip and the body when the body is disposed in the native annulus of the atrioventricular valve of the heart;

first and second control elements, the first control element being operably coupled to the first leaflet clip and the second control element being operably coupled to the second leaflet clip, each of the first and second control elements having a length sufficient to extend through the ventricle of the heart and out a wall of the ventricle when the body is disposed in the native annulus of the atrioventricular valve of the heart, the first control element being configured to allow a user to transition the first leaflet clip from the first condition to the second condition and the second control element being configured to allow the user to transition the second leaflet clip from the first condition to the second condition; and an elongate member having a proximal end and a distal end, the distal end configured to be disposed in the ventricle of the heart during deployment of the prosthetic heart valve body and the proximal end configured to extend outside the heart, the elongate member defining a first control element lumen extending from the proximal end to the distal end, and a second control element lumen extending from the proximal end to the distal end, the second control element lumen being separate from the first control element lumen, wherein the first control element is disposable in the first control element lumen and extendable out the proximal end of the elongate member, and the second control element is disposable in the second control element lumen and extendable out the proximal end of the elongate member.

2. The system of claim 1, further comprising:

an anchoring tether attached to the distal end of the body and having a length sufficient to extend from the distal end of the body through the ventricle of the heart and out the wall of the ventricle when the body is disposed in the native annulus of the atrioventricular valve of the heart, the elongate member further defining a tether lumen, the anchoring tether disposed in the tether lumen and extending out the proximal end of the elongate member.

3. The system of claim 1, wherein the first control element is disposed in the first control element lumen and the second control element is disposed in the second control element lumen.

4. The system of claim 1, wherein the proximal end of the valve body is flared radially outward when expanded and configured to engage tissue of an atrium when the body is disposed in the native annulus of the atrioventricular valve of the heart.

5. The system of claim 1, wherein each of the first control element and the second control element is a suture.

6. The system of claim 1, wherein the elongate member further defines a third control element lumen and a fourth control element lumen.

7. The system of claim 6, wherein the first control element has first and second free ends and the first control element is routed from a proximal end of the first control element lumen to a distal end of the first control element lumen, operably coupled to the first leaflet clip and then routed from a distal end of the third control element lumen to a proximal end of the third control element lumen such that the first free end of the first control element is disposed outside of the first control element lumen and the second free end of the first control element is disposed outside of the third control element lumen.

8. The system of claim 7, wherein the second control element has first and second free ends and the second control element is routed from a proximal end of the second control element lumen to a distal end of the second control element lumen, operably coupled to the second leaflet clip and then routed from a distal end of the fourth control element lumen to a proximal end of the fourth control element lumen such that the first free end of the second control element is disposed outside of the second control element lumen and the second free end of the second control element is disposed outside of the fourth control element lumen.

9. The system of claim 8, wherein the first and second free ends of the first control element are tied together to form a first loop and the first and second free ends of the second control element are tied together to form a second loop.

10. The system of claim 9, further comprising a first manipulator having a hook configured to removably couple the first manipulator to the first loop and a second manipulator having a hook configured to removably couple the second manipulator to the second loop, wherein releasing tension on the first manipulator allows the first leaflet clip to transition from the first condition to the second condition, and releasing tension on the second manipulator allows the second leaflet clip to move from the first condition to the second condition.

11. The system of claim 10, wherein the first manipulator further includes a handle coupled to a rotatable actuator knob configured to adjust tension on the first leaflet clip, and wherein the second manipulator further includes a handle coupled to a rotatable actuator knob configured to adjust tension on the second leaflet clip.

12. The system of claim 10, further comprising a first connecting member coupling the first control element to the first manipulator and a second connecting member coupling the second control element to the second manipulator, wherein the first connecting member is slidably coupled to the first control element and a second connecting member is slidably coupled to the second control element.

13. The system of claim 10, further comprising a first knot coupling the first control element to the first manipulator and a second knot coupling the second control element to the second manipulator.

14. A system for delivering a prosthetic heart valve to a native valve annulus of a heart, the valve including a self-expanding wire frame body having a proximal end and a distal end, and a leaflet clip, the system comprising:

an elongate member having a first end and a second end, the first end configured to be disposed in a ventricle of a heart during deployment of the prosthetic heart valve and the second end configured to extend outside the heart, the elongate member defining a tether lumen extending from the first end to the second end of the elongate member and at least one control element lumen extending from the first end to the second end of the elongate member, the at least one control element lumen being separate from the tether lumen; and a first control element having a first end and a second end, the first control element being disposed in the at least one control element lumen and operably coupled to the leaflet clip, the first control element having a length sufficient to extend from the leaflet clip through the at least one control element lumen and out a wall of the ventricle when the body is disposed in the native valve annulus of the heart, wherein the first control element is configured to allow a user to transition the leaflet clip between a first condition in which the body can be inserted into a native annulus and a second condition in which the leaflet clip is adapted to capture a native valve leaflet such that the native valve leaflet is engaged between the leaflet clip and the body when the body is disposed in the native annulus of the heart.

15. The system of claim 14, further comprising:
a tubular body coupled to the first end of the first control element and configured to mate with the elongate member.

16. The system of claim 15, wherein the second end of the first control element is coupled to a mandrel, the mandrel configured to be disposed in a slot defined by the tubular body.

17. The system of claim 14, wherein the valve further includes an anchoring tether attached to the distal end of the body, the anchoring tether disposed in the tether lumen and extending out the second end of the elongate member.

18. The system of claim 14, wherein the tether lumen is located along a longitudinal axis of the elongate member.

19. The system of claim 18, wherein the at least one control element lumen is radially spaced from the tether lumen.

* * * * *